(12) United States Patent
Kozbial

(10) Patent No.: US 11,952,563 B2
(45) Date of Patent: *Apr. 9, 2024

(54) DENDRITIC CELL GENERATING APPARATUS AND METHOD

(71) Applicant: FLASKWORKS, LLC, Boston, MA (US)

(72) Inventor: Andrew Kozbial, East Boston, MA (US)

(73) Assignee: FLASKWORKS, LLC, Boston, MA (US)

( * ) Notice: Subject to any disclaimer, the term of this patent is extended or adjusted under 35 U.S.C. 154(b) by 55 days.

This patent is subject to a terminal disclaimer.

(21) Appl. No.: 17/736,467

(22) Filed: May 4, 2022

(65) Prior Publication Data

US 2022/0340850 A1  Oct. 27, 2022

Related U.S. Application Data

(63) Continuation of application No. 16/841,197, filed on Apr. 6, 2020, now Pat. No. 11,339,363, which is a
(Continued)

(51) Int. Cl.
*C12M 1/00* (2006.01)
*C12M 1/12* (2006.01)
(Continued)

(52) U.S. Cl.
CPC ............ *C12M 23/34* (2013.01); *C12M 23/20* (2013.01); *C12M 23/22* (2013.01); *C12M 23/38* (2013.01);
(Continued)

(58) Field of Classification Search
CPC ...... C12M 25/14; C12M 29/10; C12M 29/26; C12M 41/00; C12M 41/48; C12M 23/16;
(Continued)

(56) References Cited

U.S. PATENT DOCUMENTS 3,848,569 A   11/1974  Folsom
3,907,687 A   9/1975   Hoeltzenbein
(Continued)

FOREIGN PATENT DOCUMENTS

AU   2012/205259 A1   8/2012
CA       2905786 A1   10/2014
(Continued)

OTHER PUBLICATIONS

Carrier, 2002, Perfusion improved tissue architecture of engineered cardiac muscle, Tissue Eng, 8(2): 175-188.
(Continued)

*Primary Examiner* — Michael L Hobbs
(74) *Attorney, Agent, or Firm* — Brown Rudnick LLP; Adam M. Schoen

(57) ABSTRACT

A cell culture cartridge is provided comprising a plurality of zones geometrically configured to provide for symmetrical fluid flow with each of the plurality of zones to avoid dead areas in flow within each of the plurality of zones. In certain embodiments, at least eight inlets are provided, with an inlet positioned at each corner of the cell culture cartridge. In certain embodiments, a shared outlet is positioned on a top surface of the cell culture cartridge.

20 Claims, 50 Drawing Sheets

Related U.S. Application Data continuation of application No. 16/192,062, filed on Nov. 15, 2018, now Pat. No. 10,647,954.

(51) Int. Cl.
  *C12M 1/34* (2006.01)
  *C12M 1/36* (2006.01)
  *C12N 5/0784* (2010.01)

(52) U.S. Cl.
  CPC ............ *C12M 25/14* (2013.01); *C12M 29/10* (2013.01); *C12M 41/00* (2013.01); *C12M 41/48* (2013.01); *C12N 5/0639* (2013.01); *C12N 2506/115* (2013.01)

(58) Field of Classification Search
  CPC ...... C12M 23/42; C12M 23/04; C12M 23/02; C12M 27/20; C12N 5/0639; C12N 5/0068; C12N 2506/11; C12N 2521/00; C12N 2533/52; C12N 2533/54; C12N 2502/11; C12N 2535/00
  See application file for complete search history.

(56) References Cited

U.S. PATENT DOCUMENTS

| | | | |
|---|---|---|---|
| 4,939,151 A | 7/1990 | Bacehowski et al. | |
| 5,536,662 A | 7/1996 | Humphries et al. | |
| 5,656,155 A | 8/1997 | Norcross et al. | |
| 6,410,309 B1 * | 6/2002 | Barbera-Guillem | C12M 23/22 435/297.5 |
| 6,607,910 B1 | 8/2003 | Dimitrijevich et al. | |
| 10,647,954 B1 * | 5/2020 | Kozbial | C12M 23/42 |
| 11,339,363 B2 * | 5/2022 | Kozbial | C12M 23/22 |
| 2002/0041868 A1 | 4/2002 | Nicolette et al. | |
| 2002/0055166 A1 * | 5/2002 | Cannon | C12M 41/00 435/303.1 |
| 2002/0110905 A1 | 8/2002 | Barbera-Guillem et al. | |
| 2003/0036192 A1 | 2/2003 | Singh | |
| 2005/0003533 A1 | 1/2005 | Kalinski | |
| 2005/0014129 A1 | 1/2005 | Cliffel et al. | |
| 2005/0186669 A1 | 8/2005 | Ho et al. | |
| 2006/0019385 A1 | 1/2006 | Smith et al. | |
| 2006/0115893 A1 * | 6/2006 | Kobayashi | C12M 23/04 435/305.3 |
| 2007/0161051 A1 | 7/2007 | Tsinberg et al. | |
| 2008/0032398 A1 | 2/2008 | Cannon et al. | |
| 2008/0227176 A1 | 9/2008 | Wilson | |
| 2008/0233607 A1 | 9/2008 | Yu et al. | |
| 2009/0155908 A1 | 6/2009 | Halberstadt et al. | |
| 2009/0162853 A1 | 6/2009 | Clark et al. | |
| 2011/0104730 A1 | 5/2011 | Larsen et al. | |
| 2012/0077243 A1 * | 3/2012 | Niazi | C12M 23/26 435/297.1 |
| 2012/0224450 A1 | 9/2012 | Priestman | |
| 2012/0277652 A1 | 11/2012 | Zhao | |
| 2013/0095566 A1 | 4/2013 | Oltvai et al. | |
| 2013/0309771 A1 | 11/2013 | Gevaert et al. | |
| 2014/0065660 A1 | 3/2014 | Kim et al. | |
| 2014/0193374 A1 | 7/2014 | Zhao et al. | |
| 2014/0295541 A1 | 10/2014 | Nakanishi et al. | |
| 2015/0158907 A1 | 6/2015 | Zhou et al. | |
| 2015/0204767 A1 | 7/2015 | Taniguchi | |
| 2016/0145563 A1 | 5/2016 | Berteau et al. | |
| 2016/0178490 A1 | 6/2016 | Civel et al. | |
| 2016/0215246 A1 | 7/2016 | Goh et al. | |
| 2016/0272934 A1 | 9/2016 | Chander et al. | |
| 2017/0042770 A1 | 2/2017 | Warner et al. | |
| 2017/0051238 A1 | 2/2017 | Tanaka et al. | |
| 2018/0171296 A1 | 6/2018 | Murthy et al. | |
| 2018/0251723 A1 | 9/2018 | Murthy | |
| 2020/0157484 A1 | 5/2020 | Kozbial | |
| 2020/0231918 A1 | 7/2020 | Kozbial | |
| 2020/0308523 A1 | 10/2020 | Murthy | |
| 2020/0385678 A1 | 12/2020 | Murthy et al. | |

FOREIGN PATENT DOCUMENTS

| | | |
|---|---|---|
| CN | 105907641 B | 6/2018 |
| EP | 1392814 B1 | 6/2007 |
| EP | 2 623 587 A1 | 8/2013 |
| JP | 2010/200693 A | 9/2010 |
| WO | 2003/010292 A2 | 2/2003 |
| WO | 2005/113742 A1 | 12/2005 |
| WO | 2009/104296 A1 | 8/2009 |
| WO | 2016/100923 A1 | 6/2016 |
| WO | 2017/004169 A1 | 1/2017 |
| WO | 2017/079674 A1 | 5/2017 |
| WO | 2018/005521 A2 | 1/2018 |
| WO | 2018/041423 A1 | 3/2018 |

OTHER PUBLICATIONS

Fiedler, 1998, Dielectrophorectic Sorting of Particles and Cells in a Microsystem, Analytical Chemistry 70:1909-15.

Fulwyler, 1965, Electronic Separation of Biological Cells by Volume, Science 150(3698):910-11.

Kashaninejad, 2016, Organ-Tumor-on-a-Chip for Chemosensitivity Assay, Micromachines, 7 (130):1-24.

Korin, 2008, Periodic 'Flow-Stop' Perfusion Microchannel Bioreactors for Mammalian and Human Embryonic Stem Cell Long-Term Culture, Biomedical Microdevices, 11(1): 87-94.

Kozbial, 2018, Automated generation of immature dendritic cells in a single-use system, Journal of Immunological Methods, 457:53-65.

Kozbial, 2018, Scale-up of a perfusion-based dendritic cell generation process, Cell & Gene Therapy Insights, 4:1117-1130.

Li, 1997, Transport, Manipulation, and Reaction of Biological Cells On-Chip Using Electrokinetic Effects, Analytical Chemistry 69(8):1564-1568.

Rosenblatt, 2011, Vaccination with dendritic cell/tumor fusion cells results in cellular and humeral antitumor immune responses in patients with multiple myeloma, Blood, 117(2):393-402.

Rothbauer, 2018, Recent advances in microfluidic technologies for cell-to-cell interaction studies, Lab on a chip, 18:249-270.

Rowjewski, 2013, GMP-Compliant Isolation and Expansion of Bone Marrow-Derived MSCs in the Closed, Automated Device Quantum Cell Expansion System, Cell Transplantation, 22(11):1981-2000.

Li, 2017, A microfluidic design to provide a stable and uniform in vitro microenvironment for cell culture inspired by the redundancy characteristic of leaf areoles, Lab on a Chip 17(22):3921-3933.

Zhang, 2015, Generation of Gradients on a Microfluidic Device: Toward a High-Throughput Investigation of Spermatozoa Chemotaxis, PLOS ONE 10(11):e0142555.

\* cited by examiner

DENDRITIC CELL GENERATING APPARATUS AND METHOD

CROSS-REFERENCE TO RELATED APPLICATIONS

The present application is a continuation of U.S. application Ser. No. 16/841,197, filed Apr. 6, 2020 (now issued as U.S. Pat. No. 11,339,363), which is a continuation of U.S. application Ser. No. 16/192,062, filed Nov. 15, 2018 (now issued as U.S. Pat. No. 10,647,954), the contents of each of which are incorporated herein by reference.

GOVERNMENT SUPPORT

The invention was made with government support under Grant Number 1819306 awarded by the National Science Foundation. The government has certain rights in the invention.

FIELD OF THE INVENTION

The invention generally relates to cell culture chambers and methods of use thereof.

BACKGROUND

Cell-based cancer immunotherapy is a method of treating cancer that uses immune active cells, including dendritic cells (DCs). Because DCs cannot be harvested in sufficient numbers otherwise, they are typically generated by the differentiation of monocytes extracted from peripheral blood. However, generating clinically relevant numbers of monocyte-derived dendritic cells for therapeutic use can be challenging. Conventional generation techniques, such as standard well plate and T-flask culture, involve a cumbersome process with many manual steps that expose the cell culture to the outside environment and require a highly trained technician.

The conventional generation techniques have numerous safety and contamination concerns, such as patient sample mix-up and misidentification, exposure to unknown contaminants inside the laminar flow hood (e.g., particulates and bacteria/fungus resistant to standard sterilization techniques such as 70% ethanol), and accidental exposure of culture to a septic environment. Furthermore, scale-up of manual DC generation techniques is generally not feasible aside from adding more culture vessels to the workflow. Automated systems that continuously perfuse fresh medium into a culture vessel while simultaneously removing depleted medium are an alternative to conventional, manual generation techniques.

Though automated systems generally have fewer safety and contamination concerns than conventional techniques, the automated systems suffer from scale-up and other issues. For example, many commercially available automated systems are not scalable for research or clinical-level production of DCs. Also, automated systems suffer from non-uniform flow, or dead spots in flow, within the cell culture vessel. Dead spots in flow (dead areas) are areas in the cell culture vessel that do not maintain uniform flow when fresh medium is provided and depleted medium is removed, thereby affecting generation of the DCs.

SUMMARY

The invention provides an automated cell culture cartridge and system for generation of dendritic cells that has uniform, symmetrical flow within the cell culture cartridge. Aspects of the invention are accomplished by designing the cell cartridge chamber to have a plurality of zones, each being geometrically configured to provide for symmetrical fluid flow and to avoid dead areas in flow within the cell culture chamber. The geometrical design provides for uniform flow and avoids dead areas, or dead spots, in flow. In that manner, the invention provides an optimal and more efficient approach to automated generation of dendritic cells (DCs).

In certain embodiments, the cell culture chamber comprises a plurality of corners. An inlet is positioned at each corner of the plurality of corners, and an outlet is positioned on a top surface of the cell culture chamber. Placement of inlets to the cell culture chamber allows for symmetrical fluid flow channels in the cell culture chamber. In some instances, the cell culture chamber comprises an octagonal shape with eight corners, each comprising an inlet. The outlet is positioned at a center of the top surface of the cell culture chamber.

The cell culture chamber also include various technical features that allow for the automation of the manual processes, dramatically reducing user intervention in the process and thereby significantly reducing the risk of contamination. Cell culture chambers allow for culture medium and cytokines to be perfused into the chamber, allowing for maintenance of more consistent levels. The achievement of consistent nutrient and cytokine levels is critical to ensure efficient cell culture and processing, and therefore predictable and effective scale up. Furthermore, a vertical flow path is provided upon fluid exiting the chamber, which ensures that the DCs, antigen-specific T-cells, and other cells involved in the culturing process remain in the chamber during perfusion.

Furthermore, the invention includes additional features directed to achieving uniform flow. As an example, the cell culture cartridge further comprises one or more pillars extending between the bottom surface and the top surface. As another example, the bottom surface comprises one or more notches at a perimeter of the bottom surface. Some embodiments of the invention further comprise one or more stopcocks operably coupled to the cell culture chamber.

Cell culture chambers of the invention may be fabricated to include a bottom surface that is made of a material to which cells adhere. In some embodiments, cells do not adhere to the bottom surface material. In some embodiments, the material of the bottom surface is treated with an air or oxygen plasma in glow discharge or corona discharge. In some embodiments, the material of the bottom surface is modified with proteins or poly-amino acids such as fibronectin, laminin, and collagen. In some embodiments, the material of the bottom surface is modified with proteins or poly-amino acids such as fibronectin, laminin, and collagen. The cell culture chamber is made from any suitable material. In certain instances, one or more materials selected from the group consisting of polystyrene and acrylate. In some embodiments of the invention, the cell culture cartridge is transparent. In some embodiments, a height of the cell culture cartridge is smaller than the largest of length or width dimensions by a factor of 10× or more.

The cell culture cartridge and system may further comprise one or more stopcocks. The one or more stopcocks may be operably coupled to the cell culture chamber. When attached to a filter, stopcocks on the cartridge allow for air exchange when the cartridge is being seeded with cell solution or harvested. When attached to luer activated transfer valves, stopcocks allow for sterile transfer of differentiation medium to fill the inlet bottle and remove the waste from the outlet bottle. This setup allows for the tubing and cartridge system to remain sterile from setup to harvest without having to break the sterile seal of the system.

Furthermore, the invention provides a completely enclosed, sterile immature DC (iDC) generation system for producing iDCs on a clinical scale, effectively eliminating the need for numerous well plates (or T-flasks/bags), ensuring a sterile and particulate free culture system, and reducing technician time in maintaining cell culture. The present invention is an automated cell culture system for aseptically generating therapeutically relevant numbers of iDCs in single cell culture cartridge. The system is also capable of further processing of iDCs to mature them via addition of maturation reagents and stimulation via addition of one or more antigens to the cell culture chamber. The cell culture system comprises a cell culture cartridge comprising a plurality of zones geometrically configured to provide for symmetrical fluid flow channels in a cell culture chamber and to avoid dead areas in flow in the cell culture chamber. The cell culture system further comprises one or more pumps operably associated with the cell culture chamber. In some embodiments, a peristaltic pump provides continuous perfusion of fresh medium into the culture vessel at a specified flow rate per inlet, such as 8 µL/min, along with removal of depleted medium into a waste reservoir. Transfer of fresh medium, removal of depleted medium, cell seeding, and iDC harvesting are performed aseptically.

In some embodiments, the cell culture system further comprises at least one fluidic connector configured to fluidically couple the cell culture chamber to a second vessel, which can be a second cell culture chamber. For example, cell culture chambers are configured to fluidically connect to one another, to enable concentration of cells into a smaller volume, if such concentration is desired for the maturation and antigen stimulation (also known as pulsing) steps. When the system is utilized to stimulate T cells with DCs, those T-cells can be automatically transferred between chambers to allow for further culturing and expansion of the T-cells in a new cell culture chamber. In some embodiments, transfer is effectuated by introducing a gas flow into the first cell culture chamber to transfer a supernatant including the first cell product through a fluidic connector and into a second cell culture chamber.

In certain aspects, the cell culture chambers of the example embodiment provide for the expansion and stimulation of T-cells using antigen-presented cells from the same patient to provide a therapeutic T-cell product that can mobilize a patient's own immune system in a manner that selectively targets a patient's tumor. These cell culture systems and methods greatly reduce the number of manual steps compared to conventional protocols. In this way, the risks of contamination are greatly decreased and the robustness and reproducibility of the manufacturing technique are greatly increased, both key considerations for safe and reliable manufacturing of therapeutic products, such as personalized T cell therapies capable of precise targeting.

In other aspects, the cell culture chamber further includes one or more fluid reservoirs that are operably coupled to the one or more pumps. The fluid reservoirs are configured to supply medium, which includes nutrients and cytokines, to the chamber.

In some embodiments, the invention further comprises one or more sensors operably coupled to the cell culture cartridge. The one or more sensors may measure any suitable parameters. In an example, the one or more sensors measure one or more parameters selected from the group consisting of pH, dissolved oxygen, total biomass, cell diameter, glucose concentration, lactate concentration, and cell metabolite concentration.

The cell culture chamber may further comprise a central processing unit (CPU). The CPU may be communicatively coupled to the one or more sensors and configured to adjust an operating state of the one or more pumps as a function of the one or more parameters measured. In an embodiment in which a flow generating mechanism is employed rather than pumps, such as an electrohydrodynamic mechanism, the central processing unit may change an operating state of the flow generating mechanism to adjust a rate of flow of the first cell product as a function of the one or more parameters.

In an embodiment, the central processing unit executes instructions to cause the system to receive a first input data comprising a size of the cell culture chamber. A second input data is then received, the second input data comprising a first concentration of a first cell type and a second concentration of a second cell type in one or more fluids that will be introduced into the cell culture chamber. Based on the first and second inputs, a perfusion rate of a perfusion fluid that will be introduced into the cell culture chamber is calculated. The calculated perfusion rate maximizes a probability of the first cell type and the second cell type contacting each other within the cell culture chamber. The first cell type is a peripheral blood mononuclear cell and the second cell type is a dendritic cell.

In an embodiment, the system further comprises one or more pumps operably coupled to one or more perfusion fluid reservoirs and operably coupled to the central processing unit, wherein the central processing unit controls the perfusion rate of the perfusion fluid by controlling the one or more pumps.

In certain embodiments, the invention provides a method of culturing dendritic cells. The method comprises providing a cell culture cartridge. The cell culture cartridge comprises a plurality of zones geometrically configured to provide for symmetrical fluid flow with each of the plurality of zones to avoid dead areas in flow within each of the plurality of zones. In some embodiments, the cell culture cartridge comprising a cell culture chamber comprising a plurality of corners, an inlet positioned at each corner of the plurality of corners, and an outlet positioned on a top surface of the cell culture chamber. Fluid flows symmetrically through the cell culture chamber.

Monocyte cells are seeded in the cell culture cartridge. The monocytes are seeded into the cell culture chamber to generate dendritic cells by providing continuous perfusion of medium into the cell culture cartridge via the inlets and removing depleted medium into a waste reservoir via the outlet. In some embodiments, the method further comprises harvesting the dendritic cells, and harvesting the cells comprises cooling the cartridge.

In an embodiment, the method further comprises transferring immature dendritic cells to a second cartridge, wherein the second cartridge is smaller than the cell culture cartridge. The immature dendritic cells undergo maturation and antigen pulsing in the second cartridge. In an embodiment, maturation and antigen pulsing may be carried out in the cell cartridge without use of the second cartridge.

In some embodiments, methods of the invention further comprise maturation of the dendritic cells and pulsing the cells with antigens.

In certain embodiments, in order to help maintain a desired environment in and around the cell culture chamber, the chamber is sized and configured to fit within an incubator. In some embodiments, the one or more pumps are located within the incubator. In other embodiments, the one or more pumps are located outside of the incubator and operably coupled to the cell culture chamber within the incubator.

In certain aspects, at least part of the system comprises disposable components, some or all of which can be housed within a non-disposable frame. In other aspects, all components of the system are disposable. Furthermore, in some embodiments, the system includes a sample tracking component for tracking and documenting patient material.

The systems and methods are designed such that any number of additional cartridges, or cell culture chambers, can be provided. In some embodiments, the system includes two or more cell culture cartridges for generating T-cells.

In certain embodiments, systems of the invention have the capability to automatically calculate and set a desired perfusion rate of perfusion fluid given various inputs, such as the size of the cell culture chamber and the concentrations of two or more cell types including dendritic cells and peripheral blood mononuclear cells. In an example arrangement, a cell culture system is provided that includes one or more cell culture chambers and a central processing unit comprising memory containing instructions executable by the central processing unit to cause the system to receive as a first input data comprising a size of the cell culture chamber, receive as a second input data comprising a first concentration of a first cell type and a second concentration of a second cell type in one or more fluids that will be introduced into the cell culture chamber, and calculate, based on the first and second inputs, a perfusion rate of a perfusion fluid that will be introduced into the cell culture chamber that maximizes a probability of the first cell type and the second cell type contacting each other within the cell culture chamber. In certain aspects, the first cell type is a peripheral blood mononuclear cell and the second cell type is a dendritic cell.

DETAILED DESCRIPTION

Figure 1:
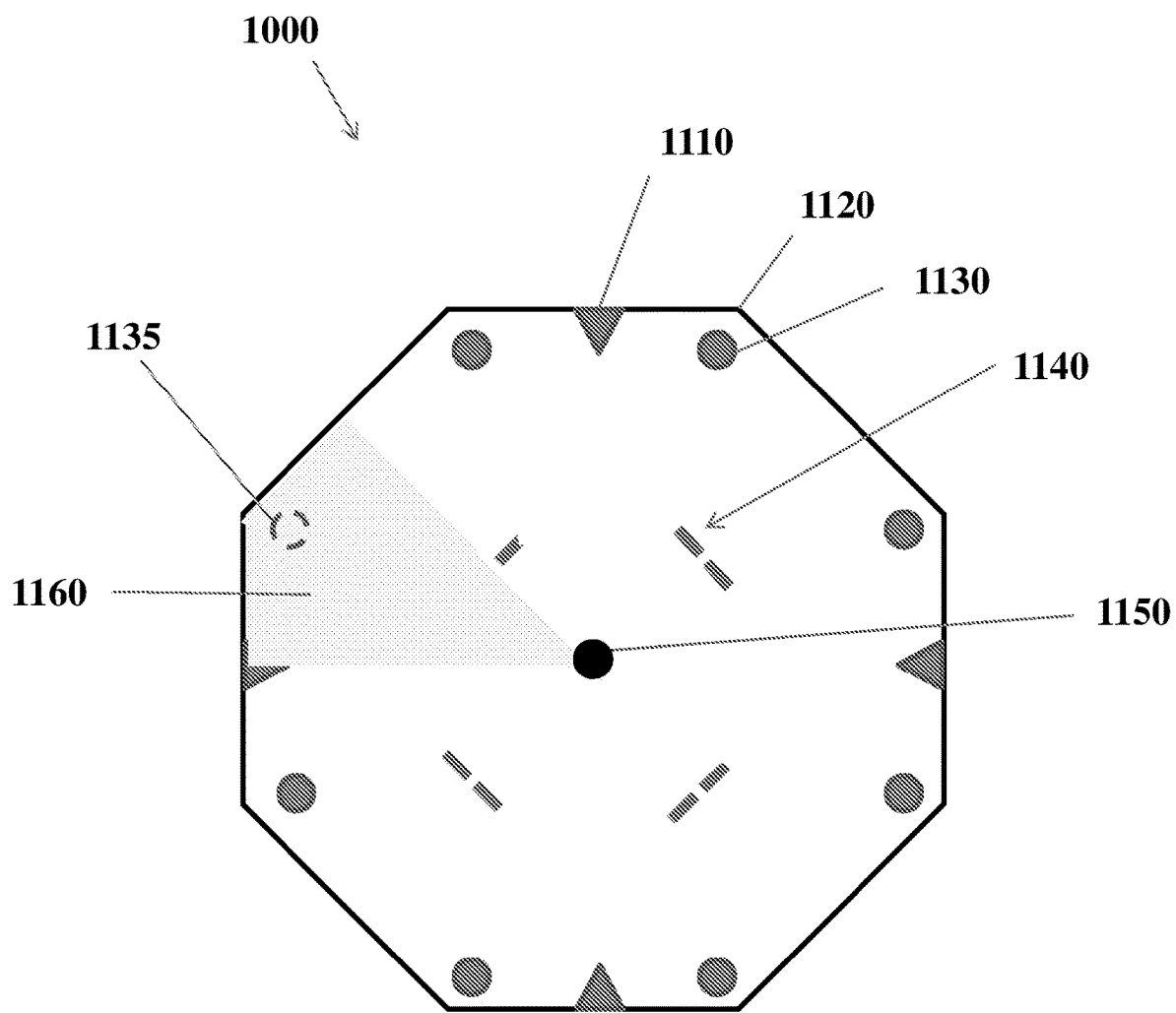
FIG. 1 shows an embodiment of a cell culture chamber of a cell culture cartridge according to the invention.

Dendritic cells (DCs) are antigen-presenting cells resident in both circulating blood and other parts of the body. DCs are critical components of the immune system. Presentation of antigens by these cells is what drives the mobilization of the immune system against infections of all kinds, as well as the development and sustainment of immunological memory. Vaccines specifically designed to target DCs have recently been developed for a broad range of diseases, including cancer, and major efforts are currently underway to develop personalized DC vaccines for infectious disease, cancer, and transplant rejection. In these disease categories, cell-based therapies using T cells expanded in vitro represent another frontier where major progress has recently been made. DCs are the most potent antigen presenting cells (APCs) and the only APC capable of inducing naïve T cells. DCs play a crucial role in the in vivo expansion of T cells and can be used to expand T cells in vitro. From a mechanistic standpoint, DCs are an indispensable part of studying human responses that are important for protective immunity against cancer and infectious diseases as well as prevention of autoimmunity and transplant rejection.

Despite the vital role of DCs in both clinical and basic research contexts, the method for obtaining these cells from individuals remains an under-developed and inefficient process. Because DCs are present in very low concentrations (<1%) in blood, these cells must be generated from monocytes, involving a laborious process of static culture and stimulation with cytokines (IL-4 and GM-CSF) contained in culture medium. In particular, numerous manual steps are required to go from a sample of patient-derived whole blood, leukopharesis product, or peripheral blood mononuclear cells (PBMCs) to sufficient numbers of DCs that can be utilized for vaccine development, T cell therapy, or mechanistic studies. Scaling, even to the level of tens of samples for a study involving one or two conditions or separate blood draws, is burdensome due to the resource requirement in terms of personnel hours and number of manual steps. Considering the existing and projected use of these cells at a much larger scale, such as in autologous DC-based cell therapies and vaccines, the conventional approach to DC generation poses an unusually large burden, most significantly in terms of efficiency and reliability of the manufacturing process but also cost of supplies and labor.

The invention provides an automated cell culture cartridge and system for generation of dendritic cells that has uniform, symmetrical flow within the cell culture cartridge. A cell culture cartridge is provided which comprises a cell culture chamber formed between a top surface of the cell culture cartridge and a bottom surface of the cell culture cartridge. The cell culture chamber comprises a plurality of zones geometrically configured to provide for symmetrical fluid flow channels in a cell culture chamber and to avoid dead spots or dead areas in the cell culture chamber. Dead spots in flow (dead areas) are areas in the cell culture vessel that do not maintain uniform flow when fresh medium is provided and depleted medium is removed and thereby affect generation of the DCs. By providing the plurality of zones in the cell culture cartridge, the invention provides symmetrical flow channels without dead spots or areas for fluid flow. In addition, the cell culture chambers of an example embodiment provide features that allow for uniform flow of the fresh medium and removal of depleted medium.

FIG. 1 shows a top view of a cell culture chamber 1000. The cell culture chamber 1000 is formed between a top surface and a bottom surface of a cell culture cartridge. A plurality of fluid flow inlets 1130 are provided in the chamber. The embodiment shown in FIG. 1 comprises eight inlets, with one of the inlets shown by phantom lines 1135. The inlets 1130 are arranged at each corner 1120 of the cell culture cartridge. The inlets 1130 may be located on a top surface of the cell culture cartridge. One outlet 1150 is located at a center of the cell culture chamber, on a top surface of the cell culture cartridge. The chamber 1000 comprises a plurality of zones 1160 geometrically configured to provide for symmetrical fluid flow channels in the cell culture chamber 1000. Notches 1110 are arranged on the outer perimeter of the cell culture chamber and help to avoid dead areas, or dead spots, where there is non-uniform fluid flow, in the cell culture chamber. Pillars 1140 extend from the bottom surface to the top surface, so that the top surface does not sag or bow and create increased pressure in the chamber. The embodiment shown in FIG. 1 is an exemplary non-limiting embodiment of the invention. Other non-limiting embodiments may comprise a different number of inlets. In some examples of non-limiting embodiments, a cartridge according to the invention may comprise 2 inlets, 5 inlets, 10 inlets, 13 inlets, 14 inlets, 20 inlets, 30 inlets, and 100 inlets. Non-limiting embodiments may further comprise a different number of corners. In some examples of non-limiting embodiments, a cartridge according to the invention may comprise 5 corners, 10 corners, 17 corners, 25 corners, 50 corners, and 100 corners.

In the invention, symmetry of fluid flow is achieved in the cell culture cartridge. For example, the cartridge is comprised of individual zones, and each individual zone is the space between two fluid inlets. As shown in FIG. 1, each zone has a base of a triangle that tapers in the middle, with each zone being symmetrical to the other zones. In some instances, a number of fluid inlets in the cartridge may be greater or less than 8 fluid inlets. In a preferred embodiment, the cartridge is divided into 8 individual regions or zones with an inlet and shared outlet (center). This ensures that the entire cartridge is perfused with fresh differentiation medium and dead areas, or dead spots in flow, do not form. Furthermore, 4 triangle notches 1110 are located around the perimeter to avoid dead areas, or dead spots in flow which would occur in those areas. The cartridge comprises 8 pillars to support the top surface of the cell culture cartridge, which may be constructed of poly(methyl methacrylate) (PMMA or acrylate). Without the pillars, the PMMA top surface would sag and pressure would build up within the cartridge since the medium would be supporting the cartridge top.

The cartridge may be constructed out of any suitable material. In some instances, the cartridge is constructed from polystyrene, acrylate, or a combination thereof. As an example, the base or bottom surface comprises polystyrene and the top surface and side surfaces are acrylate. As another example, for high volume manufacturing, the cartridge may be made entirely of polystyrene.

In one example embodiment, the bottom surface comprises polystyrene and/or acrylate. One benefit of using polystyrene for the bottom surface where culturing will occur is a useful role that this material plays in the process of generating dendritic cells from PBMCs. Specifically, polystyrene surfaces can be used to enrich monocytes from a heterogeneous suspension of PBMCs. This is a first step in the culture process utilized to generate DCs by differentiation of monocytes via culture in medium containing, for example, IL4 and GM-CSF. The use of the same polystyrene surface for dendritic cell production all the way through one cycle of T-cell stimulation is tremendously valuable from a bioprocess standpoint as it eliminates a large number of transfer steps that would otherwise be necessary, thereby allowing for a closed system for DC-stimulated therapeutic T-cell manufacturing.

Furthermore, any suitable material treatment may be performed on the cartridge. In some embodiments, the bottom polystyrene surface may be modified to facilitate cell adhesion. For example, the bottom polystyrene surface may undergo treatment with an air or oxygen plasma, also known as glow discharge or corona discharge. For example, the bottom polystyrene surface may undergo modification with proteins or poly-amino acids that are known to facilitate cell adhesion, including but not limited to fibronectin, laminin, and collagen.

The bottom surface can have a surface area comparable to conventional well plates, such as 6- and 24-well plates (9.5 $cm^2$ and 1.9 $cm^2$, respectively) or T flasks (25 $cm^2$ to 225 $cm^2$). It is also to be understood that the surface area can be smaller or even much larger than conventional well plates (e.g., having surface areas comparable to standard cell culture dishes and flasks), such as having a surface area between about 2.0 $cm^2$ and about 500 $cm^2$, for example, about 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 45.0, 50.0, 55.0, 60.0, 65.0, 70.0, 75.0, 100.0, 125.0, 150.0, 175.0, 200.0, 400.0, 500.0 $cm^2$, and any surface area in between.

The surfaces of the cell culture cartridge can be joined together using any methods known in the art, such as mechanical fastening, adhesive and solvent bonding, and welding. However, given that the cellular immunotherapeutic product produced using systems and methods of embodiments of the invention will be administered to a human patient, regulatory issues may prevent the use of certain, or all, adhesives in assembling the cell culture chambers. Accordingly, in certain embodiments, the surfaces are joined without using adhesive. In one embodiment, all surfaces of the cell culture chamber, such as the bottom, side, and top walls, comprise the first material (e.g., polystyrene) and are joined together using ultrasonic welding. It is to be understood that the aforementioned configurations are only examples and that other configurations for joining the surfaces are also contemplated embodiments of the present invention.

The height of the one or more cell culture chambers can vary. For example, and not limitation, an example range of cell culture chamber heights includes heights of anywhere from 0.5 mm to 100 mm, such as 0.5, 1.0, 2.0, 3.0, 4.0, 5.0, 6.0, 7.0, 8.0, 9.0, 10.0, 15.0, 20.0, 25.0, 30.0, 35.0, 40.0, 45.0, 50.0, 55.0, 60.0, 65.0, 70.0, 75.0, 80.0, 85.0, 90.0, 95.0, 100.0 mm, or more, or any height therebetween. In certain embodiments, the heights of the chamber can be comparable to liquid heights in cultures that are typically performed in 6- and 24-well plates, such as between 2 and 6 mm, with a volume capacity of about 0.8 mL to 6 mL. In other embodiments, the cell culture chambers will be of large size, such as between 10 mm and 50 mm, with a culture surface of about 50 $cm^2$.

Figure 2:
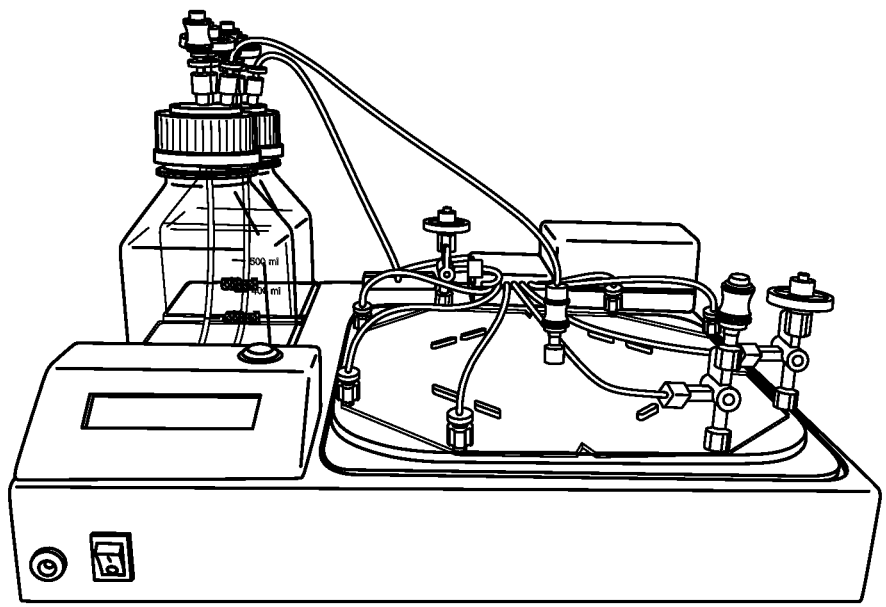
FIG. 2 shows a front view of a cell culture cartridge and system.
Figure 3:
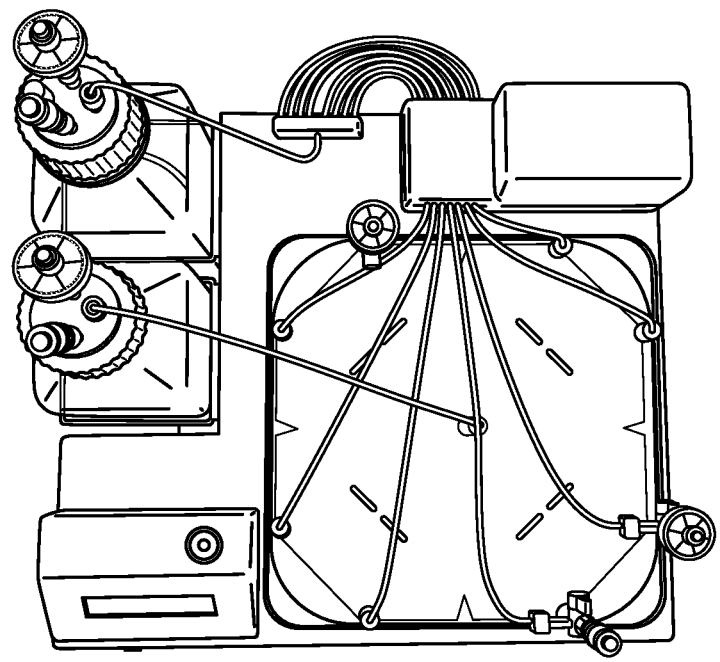
FIG. 3 shows a top view of a cell culture cartridge and system.
Figure 4:
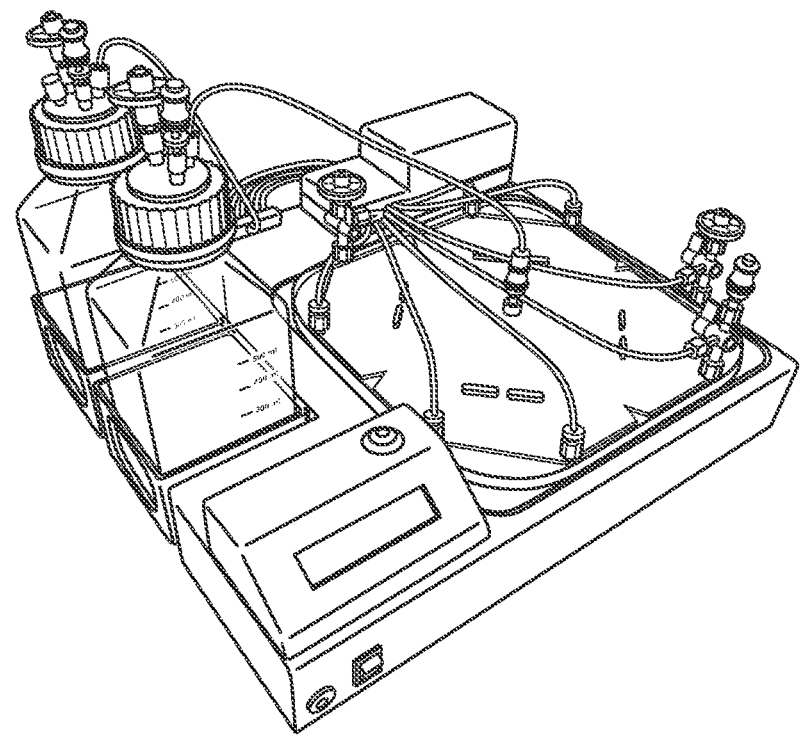
FIG. 4 shows a left side view of a cell culture cartridge and system.
Figure 5:
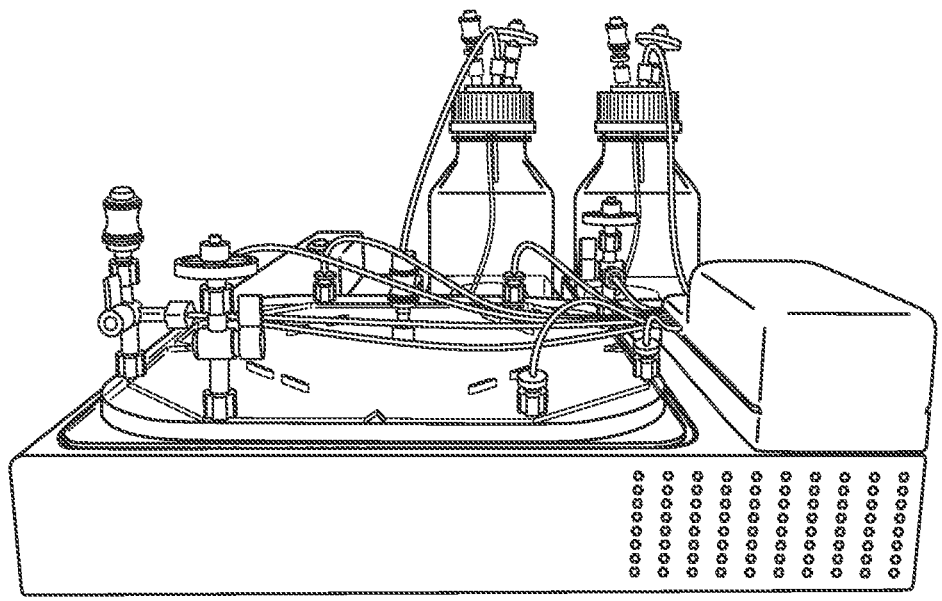
FIG. 5 shows a right side view of a cell culture cartridge and system.

In some embodiments of the invention, the cartridges are optically clear or transparent. Such optical clarity, in combination with the fluidic ports being segregated appropriately, allows a user to view cells at any vertical plane within the cartridge. As shown in FIGS. 2-5, embodiments of the invention comprise optically clear or transparent cell culture cartridges. FIG. 2 shows a front view of a cell culture cartridge and system. FIG. 3 shows a top view of a cell culture cartridge and system. FIG. 4 shows a left side view of a cell culture cartridge and system. FIG. 5 shows a right side view of a cell culture cartridge and system.

Further, as shown in FIGS. 2-5, stopcocks may be placed on the cartridge or on the reservoir bottles. In particular, stopcocks are placed at specific ports on the cartridge and each serves a specific function. Placement is specific to each function, and work was performed to determine the optimal locations to ensure that the process is successful and workflow is easy. For example, the stopcock at the front is for seeding and harvesting, and the luer activated valve (LAV) on top of stopcock allows for syringe to be sterilely connected. The stopcock at the front-right is for seeding and harvesting (adding cold buffer for washes), and air inside the cartridge will flow out through the filter at this stopcock as cell solution is seeded into the cartridge. As another example, the stopcock at the back-left is for harvest, and air inside the cartridge will flow into the cartridge as cell solution is removed. The filters attached to the stopcocks avoid pressure or vacuum buildup within cartridge as liquid is being added or removed from cartridge.

In the invention, LAVs may be used on the bottles to add and/or remove medium. Traditionally, LAVs are sold and marketed to be used for anesthesia and IV lines. Therefore, using the LAVs for addition or removal of medium departs from traditional use.

Computational fluid dynamics (CFD) aided in the design of the current EDEN cartridge. In particular, CFD aided in designing the size of cartridge, placement of pillars, and placement and size of triangle notches.

In some embodiments, an 8 μL/min perfusion flow rate may be maintained. Because this is the same perfusion rate as cell culture systems such as MicroDEN, linear scaling up of MicroDEN runs using systems according to the present invention (EDEN) is likely. Each of the 8 sub-sections of the EDEN cartridge are slightly larger than a single MicroDEN cartridge, so the effect of perfusion on the cells should be similar in EDEN as in MicroDEN. Therefore, the invention allows MicroDEN experiments to be easily scaled to EDEN without unknown factors such as different fluid flow rate.

Figure 6:
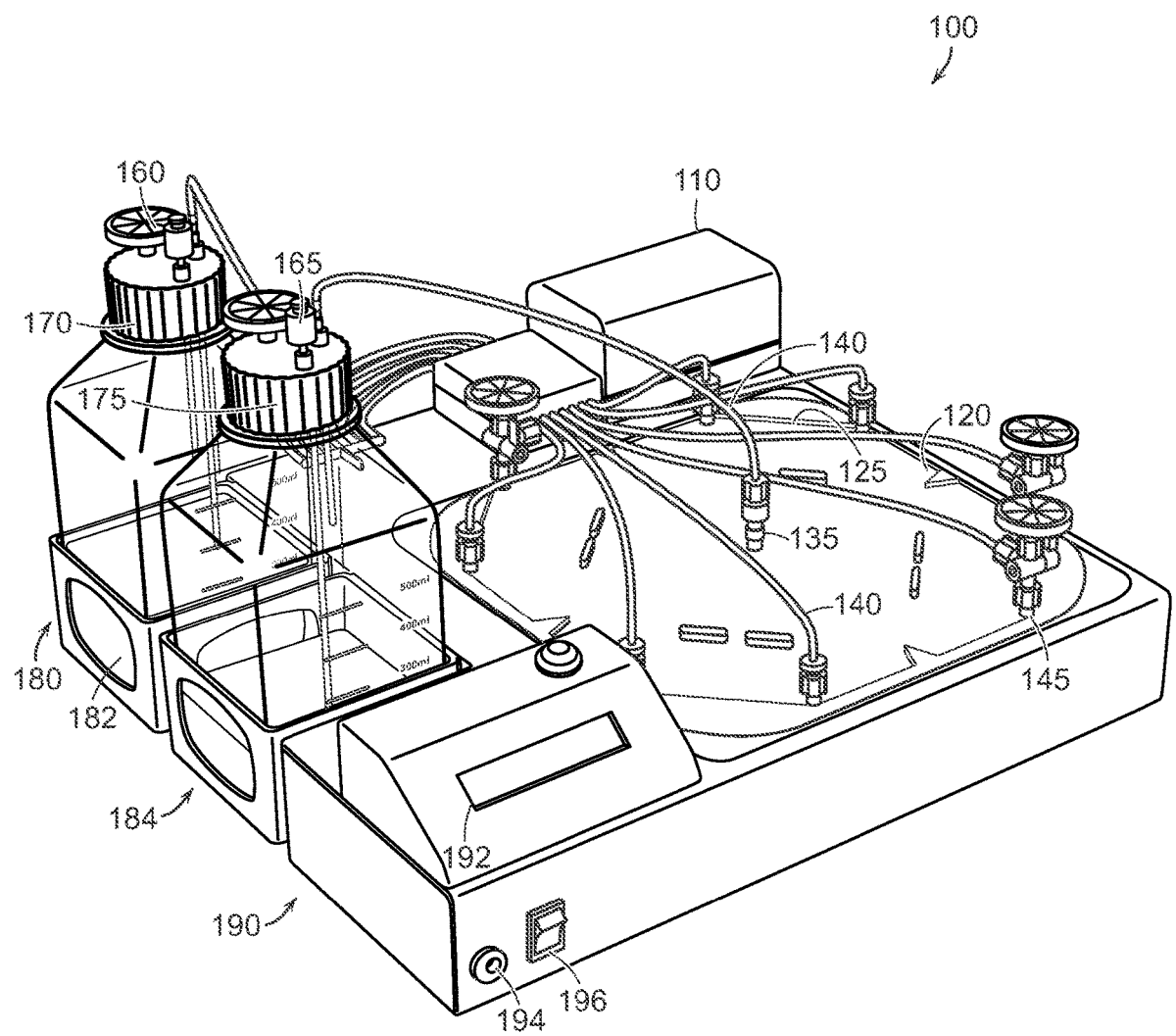
FIG. 6 shows an embodiment of a system 100 of the invention.

FIG. 6 shows an embodiment of a system 100 of the invention. A peristaltic pump 110 is provided. The pump 110 is used to pump fluid into and out of the cell culture cartridge 120. The cell culture cartridge 120 has a bottom surface 125 to which cells adhere. In other embodiments, cells do not adhere to the bottom surface. The cell culture cartridge 120 has eight fluid inlets 145 arranged at the corners of the cell culture cartridge 120. One fluid outlet 135 is arranged at a center of the cell culture cartridge 120. Connective tubing 140 connects the fluid inlets with the differentiation medium reservoir (perfusion source) 180 containing differentiation medium 182. The differentiation medium reservoir 180 contains differentiation medium 182 that will be pumped into the cell culture cartridge 120. The connective tubing 140 also connects the fluid outlet 135 with the waste reservoir 184. Depleted medium will be pumped out of the cell culture cartridge 120 through the outlet 135 and into the waste reservoir 184. Lids 170 and 175 on the differentiation medium reservoir 180 and the waste reservoir 184 are not removable, thereby maintaining a sterile system. In other embodiments, the lids 170 and 175 are removable. Stopcocks and/or LAVs 160 and 165 on the reservoir bottles 180 and 184 allow for sterile transfer of differentiation medium to fill the inlet bottle and remove waste from the outlet bottle. The console 190 provides designated spaces for arrangement of the previously mentioned components and also provides a display/userface 192, connection 194, and on/off switch 196.

Figure 7:
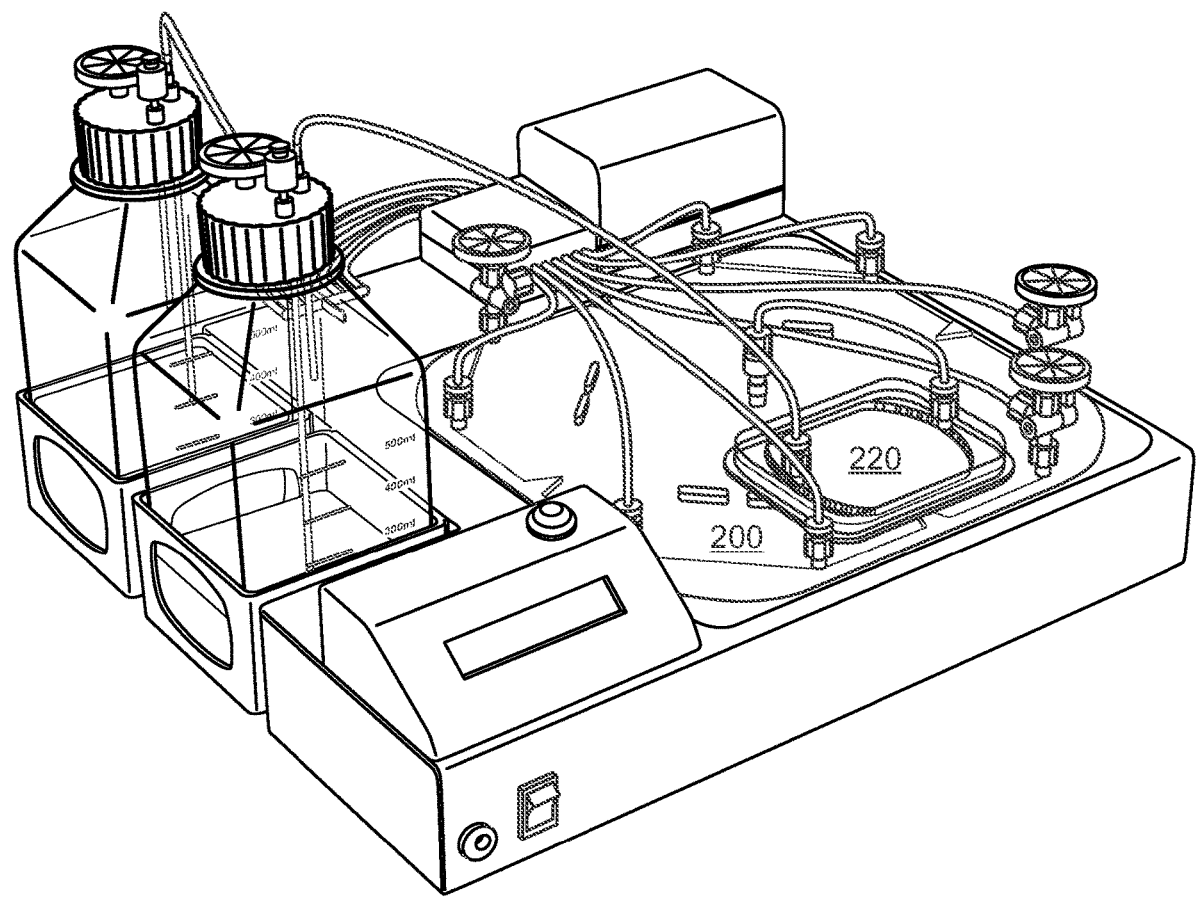
FIG. 7 shows an embodiment of the invention with two cartridges.

FIG. 7 shows an embodiment of the invention with two cartridges. A cell culture cartridge 200 is provided for monocyte to dendritic cell differentiation. A smaller cartridge 220 is provided for maturation and antigen pulsing. In other embodiments, maturation and antigen pulsing may be carried out in the main cell culture cartridge without use of a second cartridge.

Figure 8:
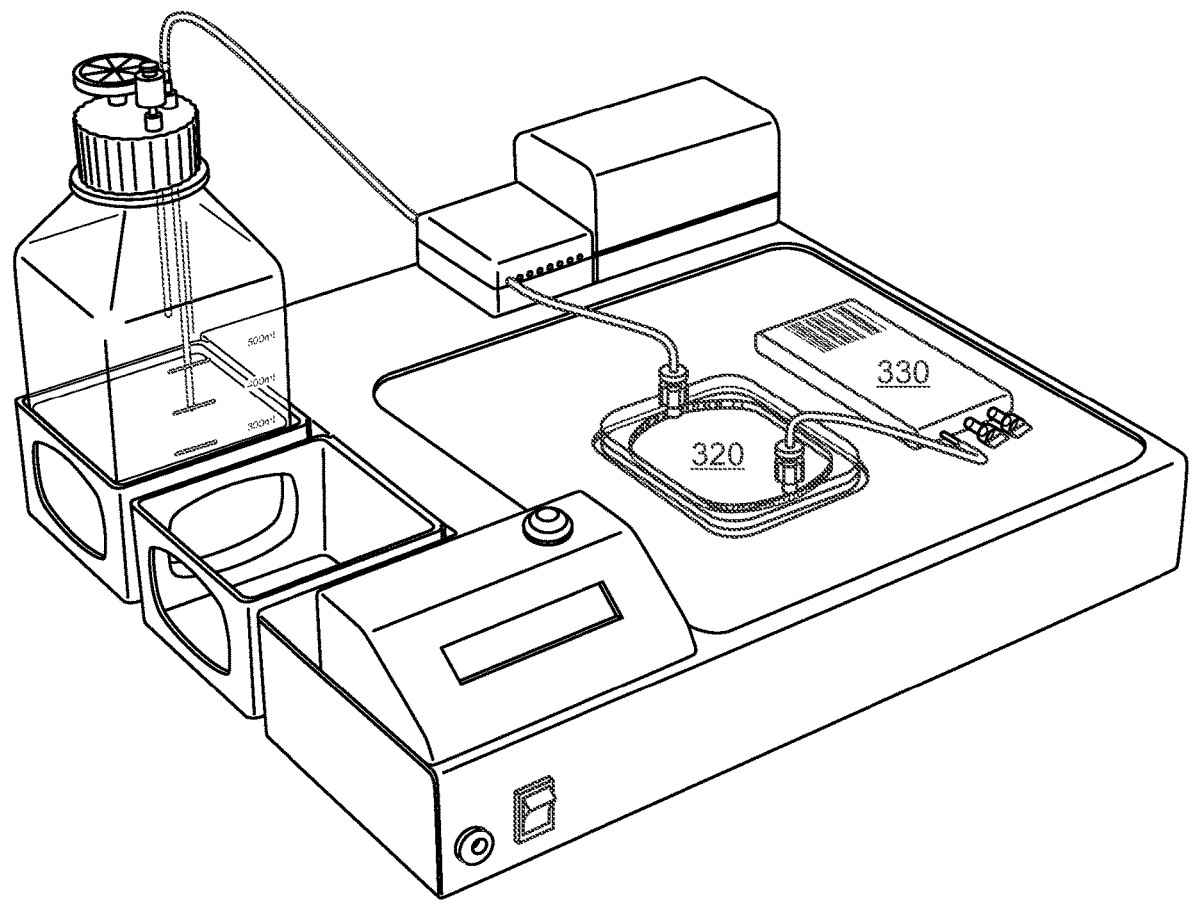
FIG. 8 shows an embodiment of the invention showing transfer from a smaller cartridge to an infusion bag.

FIG. 8 shows an embodiment of the invention having a smaller cartridge 320 for maturation and antigen pulsing. The smaller cartridge 320 is fluidly connected to an infusion bag 330 containing the final product transferred from the smaller cartridge 320.

Figure 9:
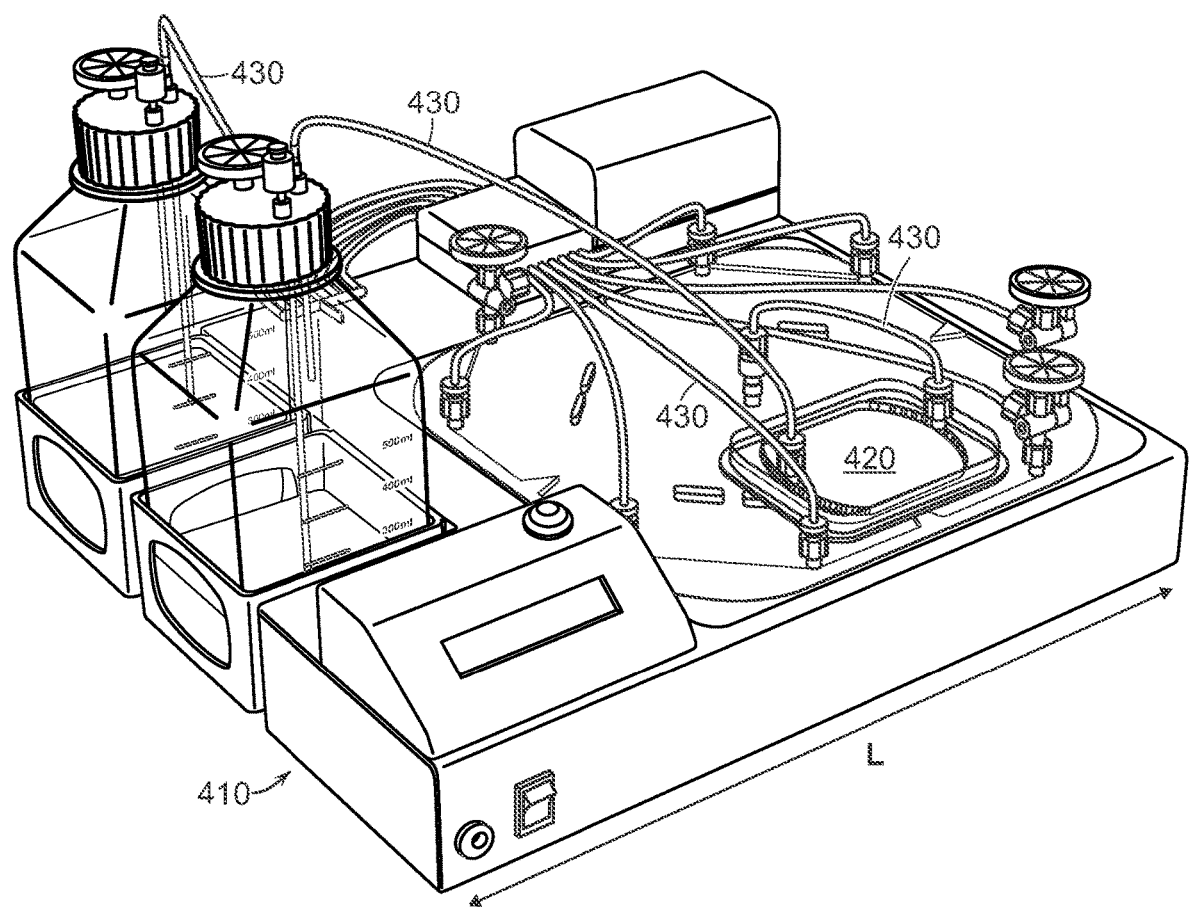
FIG. 9 shows the disposable and non-disposable components of the invention.

FIG. 9 shows the disposable and non-disposable components of the invention. The EDEN console 410 is non-disposable and has a length L. In this embodiment, the length L is 14 inches. A smaller cartridge 420 is for maturation and antigen pulsing. Connective tubing 430 connects the inlets and outlet with the reservoirs and the cartridges. The smaller cartridge 420 and connective tubing 430 are single-use and disposable.

Figure 10:
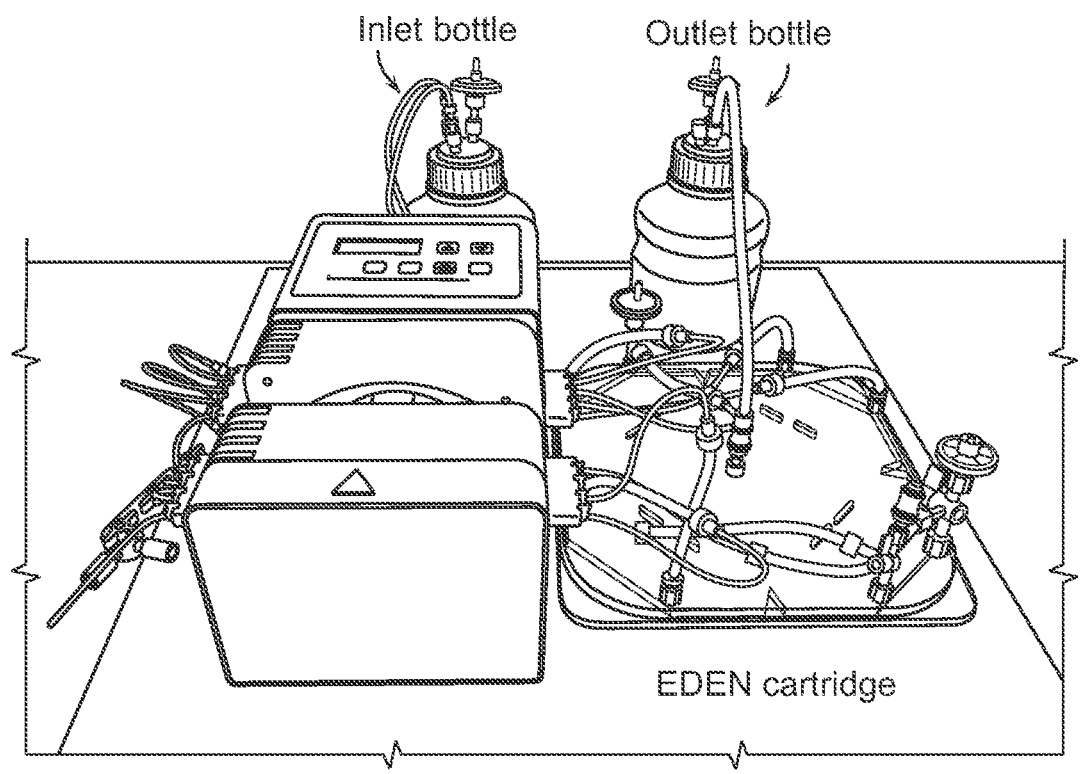
FIG. 10 shows an embodiment of the EDEN automated fluidic system.

FIG. 10 shows an embodiment of the EDEN automated fluidic system. The EDEN system generates monocyte derived iDCs while continuously perfusing fresh differentiation medium into the cell culture cartridge.

Figure 11:
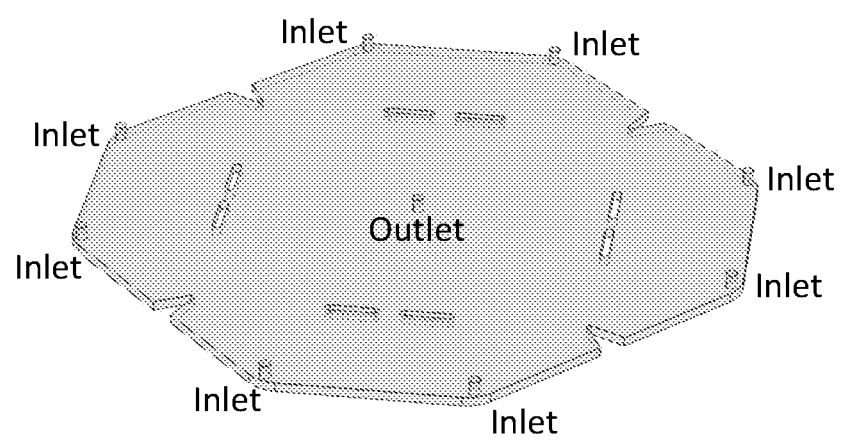
FIG. 11 shows a cell culture cartridge design of the cell culture cartridge flow channel.
Figure 12:
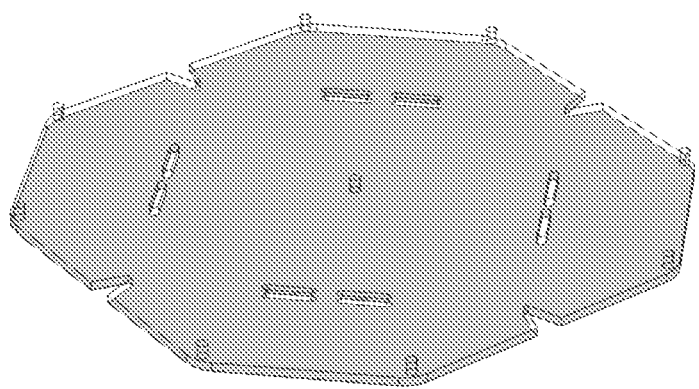
FIG. 12 shows a cell culture cartridge design of the polystyrene surface (shaded) at the base of the cell culture cartridge where the cells reside.
Figure 13:
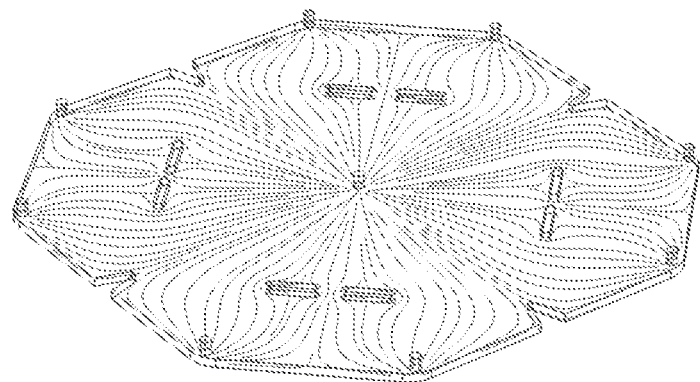
FIG. 13 shows a cell culture cartridge design of streamlines due to perfusion within the cell culture cartridge.
Figure 14:
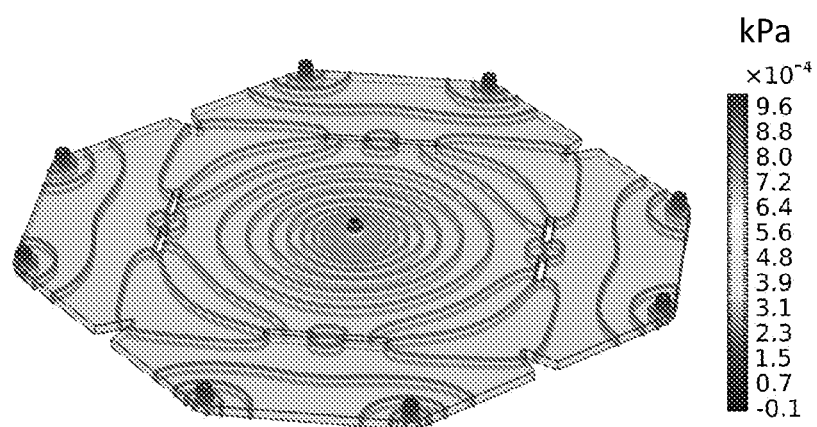
FIG. 14 shows a cell culture cartridge design of gauge pressure due to perfusion within the cell culture cartridge.

FIGS. 11-14 show cell culture cartridge designs according to embodiments of the invention. FIG. 11 shows a cell culture cartridge design of the cell culture cartridge flow channel. FIG. 12 shows a cell culture cartridge design of the polystyrene surface (shaded) at the base of the cell culture cartridge where the cells reside. FIG. 13 shows a cell culture cartridge design of streamlines due to perfusion within the cell culture cartridge. FIG. 14 shows a cell culture cartridge design of gauge pressure due to perfusion within the cell culture cartridge.

Figure 15:
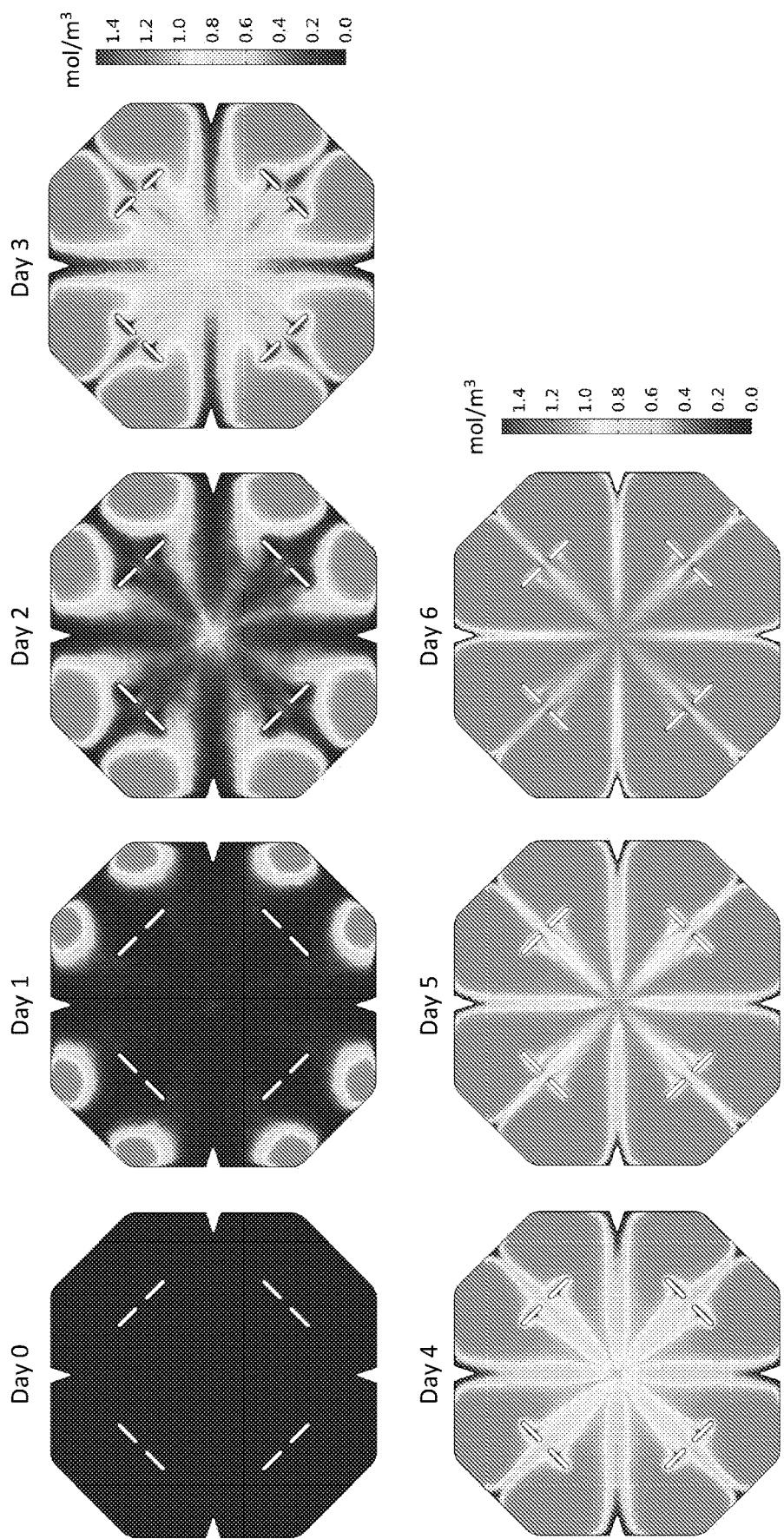
FIG. 15 shows cytokine perfusion into the cell culture cartridge.

FIG. 15 shows cytokine perfusion into the cell culture cartridge. In this embodiment, the cartridge is initially filled with water (medium) without cytokines. Cytokines perfuse into the cartridge at the 8 inlet ports at 1.16 mol/m3 (IL-4), flow through the cartridge driven by perfusion, and flow out through the outlet port at the center. In practice, the cell culture cartridge is filled with medium containing cytokines. The data is taken at the lower surface, or bottom surface, of the flow channel, as shown in FIG. 12.

Figure 16:
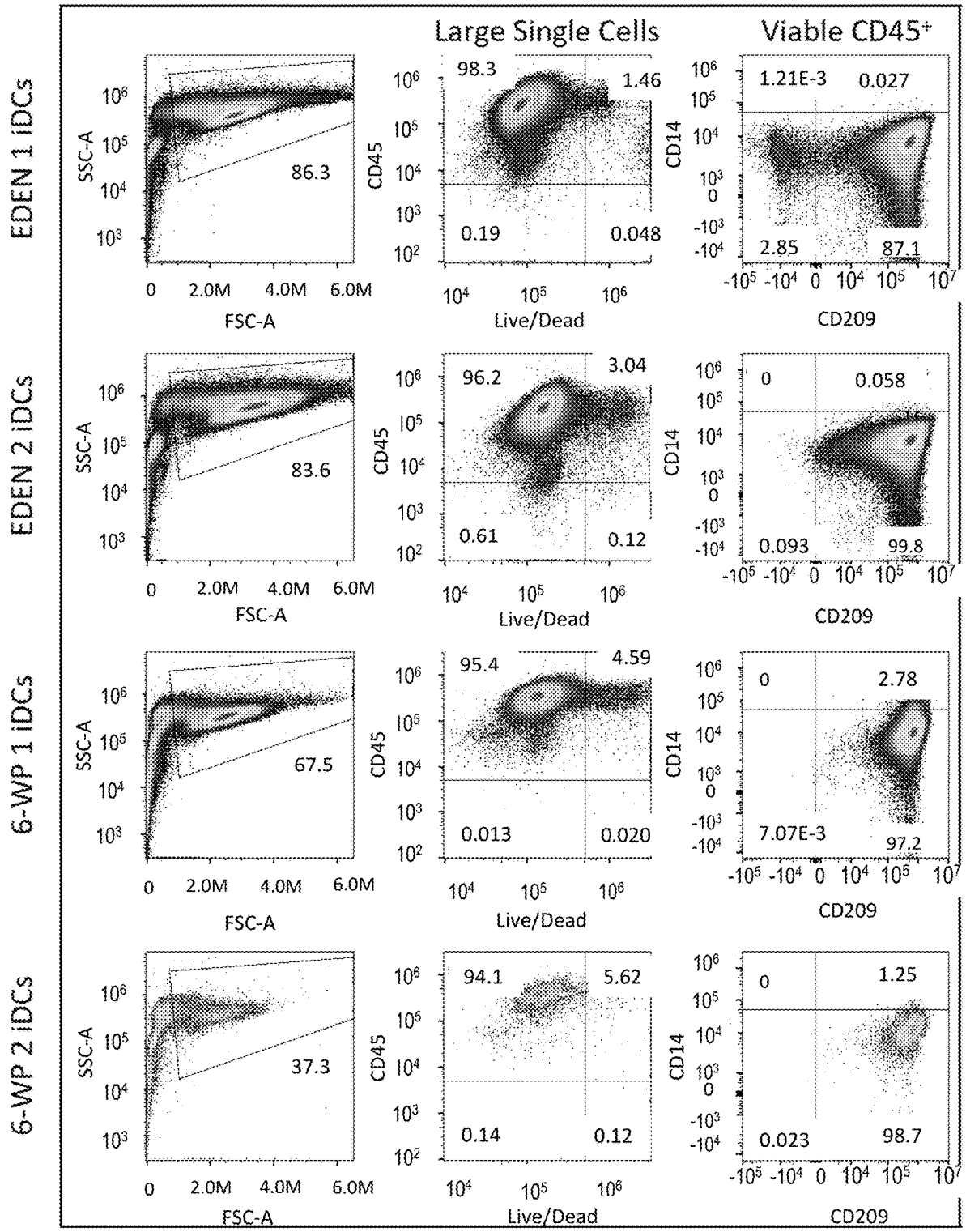
FIG. 16 shows the phenotype of the cell culture cartridge and 6-well plate generated iDCs differentiated from MOs for 6 days.
Figure 16:
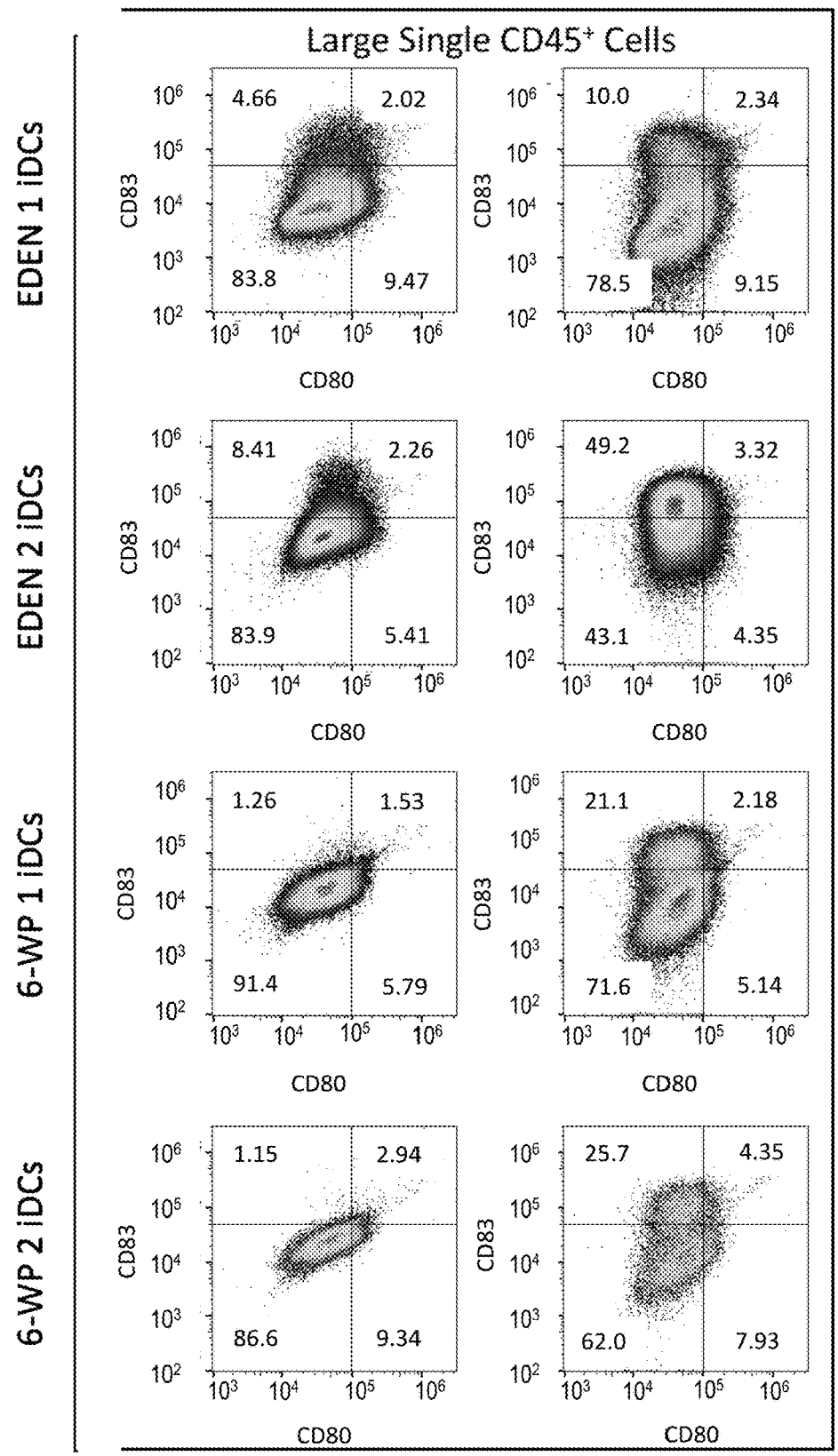

FIG. 16 shows the phenotype of the cell culture cartridge and 6-well plate generated iDCs differentiated from MOs for 6 days. Labels above the figures indicate the gates from which the plots derive.

Figure 17:
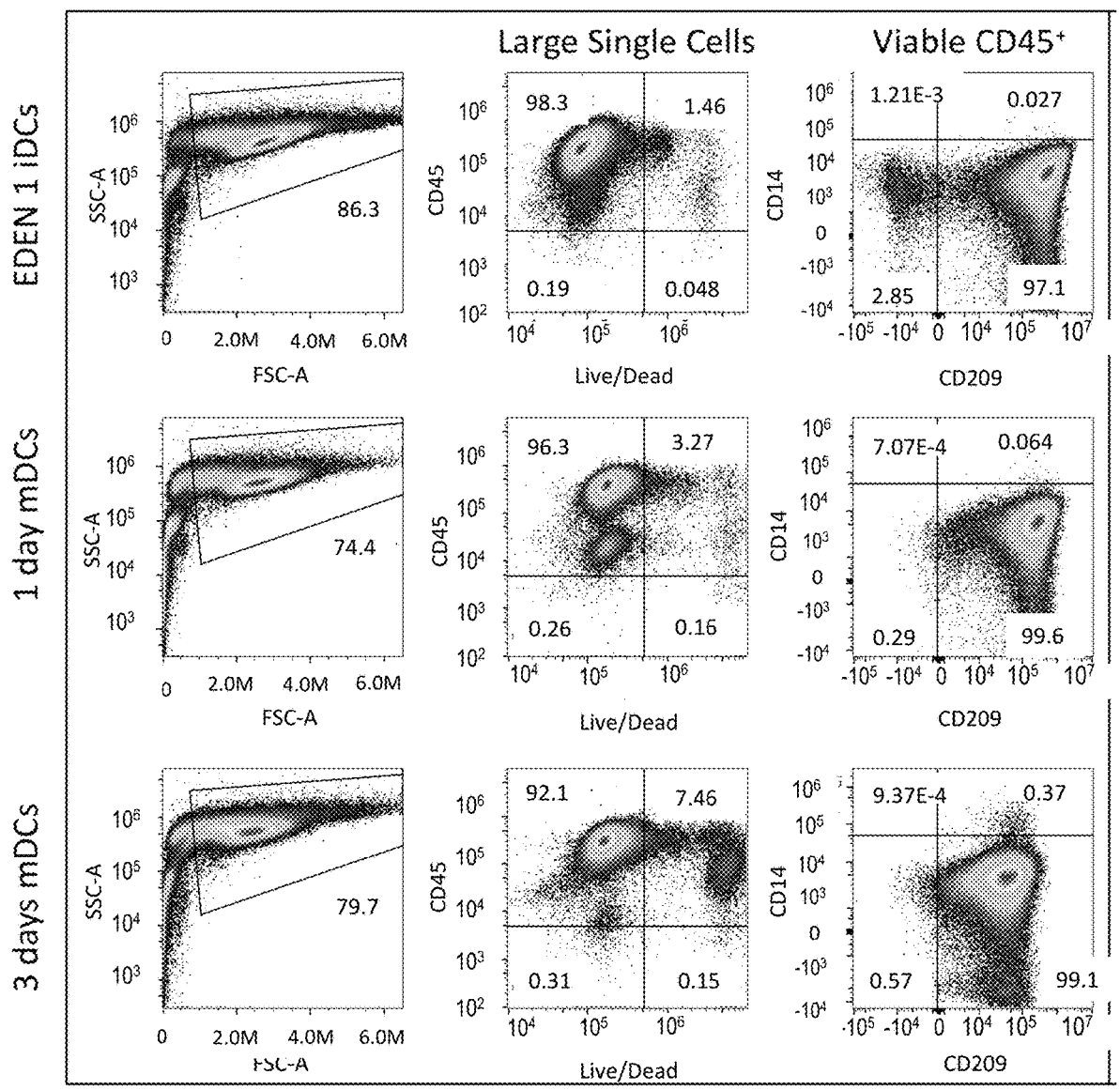
FIG. 17 shows the IDC and mDC phenotype from the cell culture cartridge. IDCs were generated in the cell culture cartridge then seeded into cell culture systems of the invention for 1 or 3 days maturation. Labels above the figures indicate the gates from which the plots derive.
Figure 17:
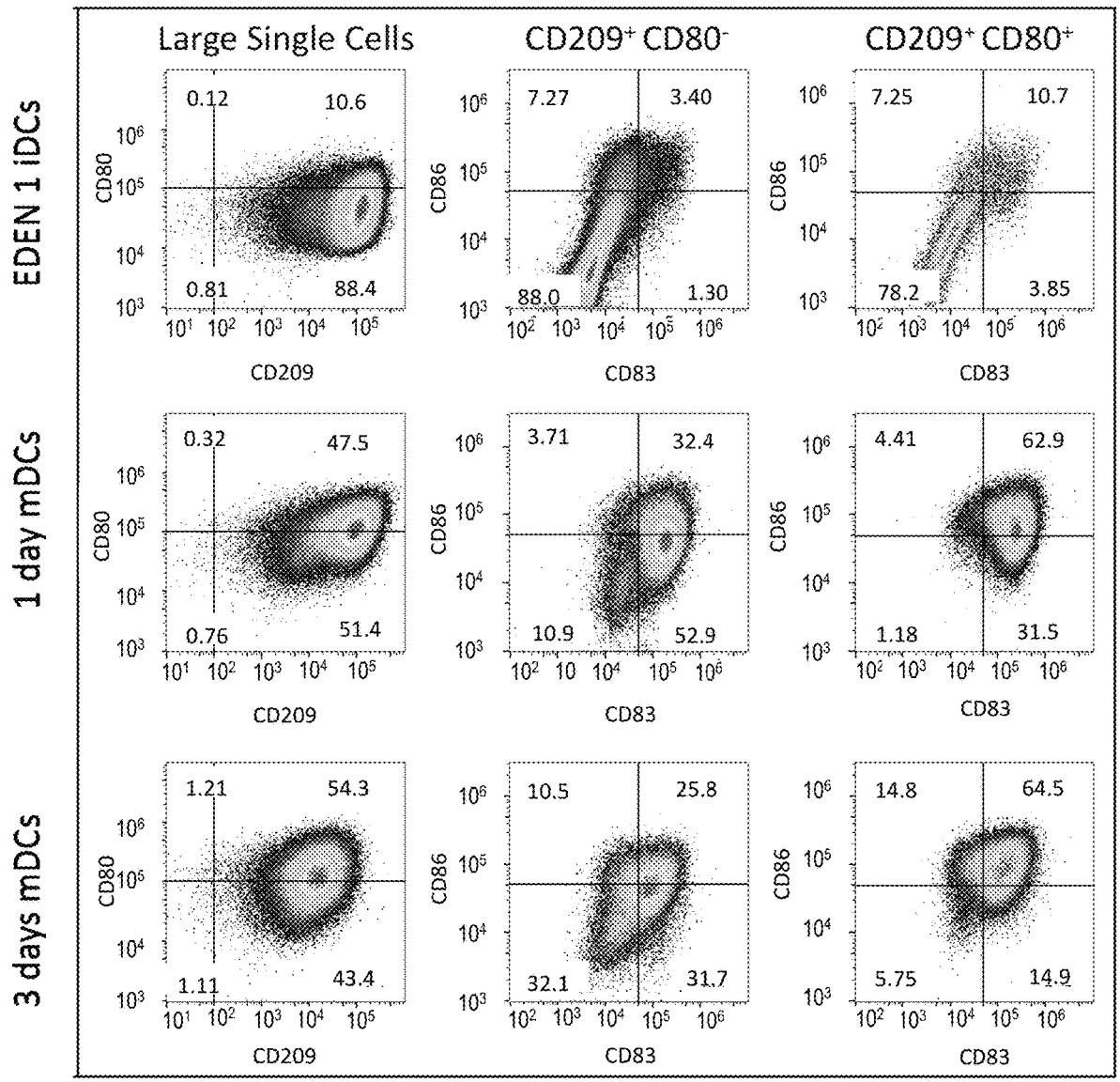

FIG. 17 shows the iDC and mDC phenotype from the cell culture cartridge. IDCs were generated in the cell culture cartridge then seeded into cell culture systems of the invention for 1 or 3 days maturation. Labels above the figures indicate the gates from which the plots derive.

Figure 18:
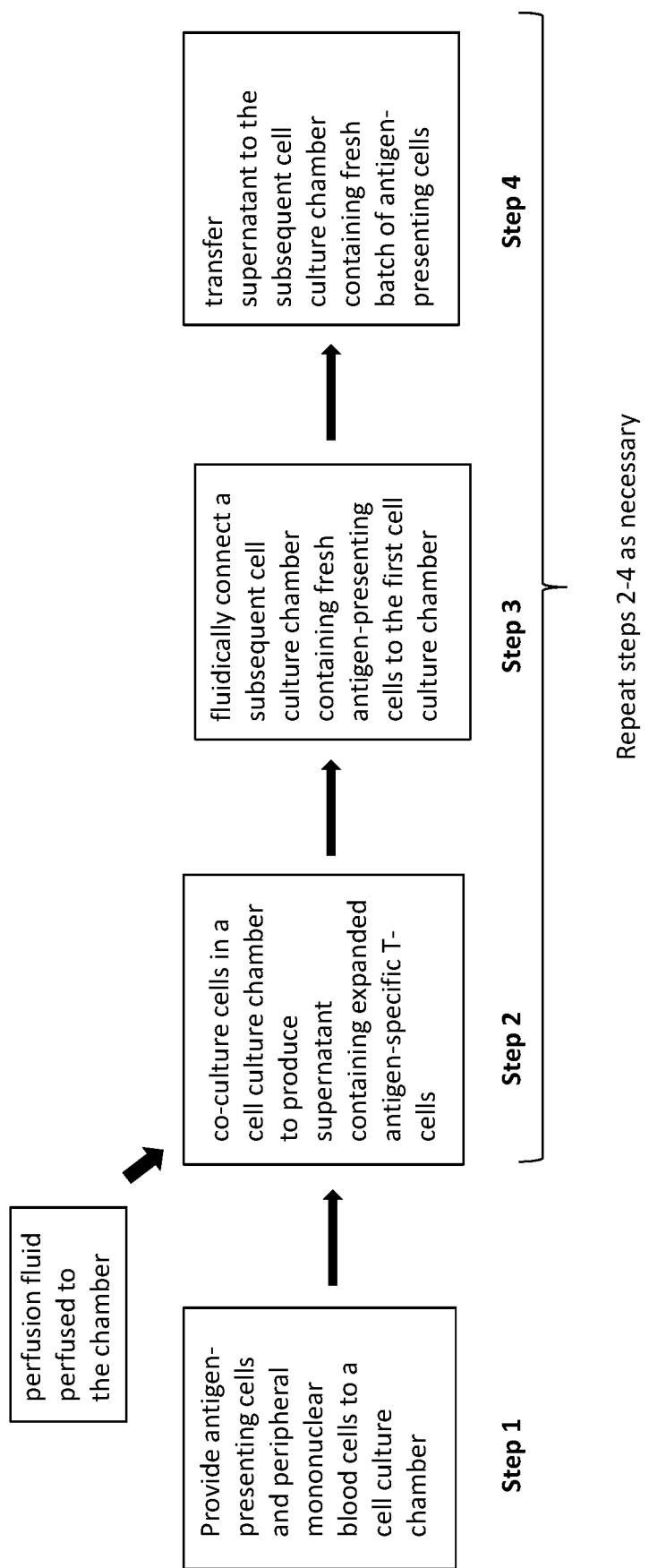
FIG. 18 shows an example method for producing immunotherapeutic products in accordance with an embodiment of the present invention.

FIG. 18 shows an example method for producing immunotherapeutic products in accordance with an embodiment of the present invention. FIG. 18 shows an overview of a method for generation of cell-based immunotherapeutic products using the systems described herein. Briefly, the steps in generating cellular therapeutic product in accordance with certain embodiments of the present invention include the co-culturing of stimulated antigen-presenting cells with T-cell containing cells in a biological reactor containing a cell culturing chamber. A supernatant containing expanded therapeutic T-cell products is generated during culturing. In certain aspects, in order to produce a quantity of antigen-specific T-cells sufficient to elicit a therapeutic response in a patient, the T-cells must undergo additional culturing in one or more additional cell culturing chambers. In order to effectuate this additional culturing, the transfer of supernatant from the culture chamber in which the supernatant was generated to a subsequent cell culture chamber containing a fresh supply of antigen-presenting cells must occur. The transfer of supernatant between cell culture chambers may involve the introduction of a gas flow into the first cell culture chamber that transfers the supernatant comprising the first cell product through a fluidic connector and into the new cell culture chamber. Furthermore, during each of the culturing steps, perfusion fluid containing, for example, medium and cytokines, can be perfused to the chambers. In certain aspects, the perfusion fluid flows through the chambers along a vertical flow path so as to ensure that the cells remain within the chamber during culturing. The only manual steps involved using the systems of the invention are the provision of one or more subsequent cell culture cartridges to the system, each cell culture cartridge containing a cell culture chamber, with each chamber containing a new batch of antigen peptide-pulsed autologous antigen-presenting cells. Using gas facilitated transfer may also involve manual steps of manipulating the setup of the system, but will not break sterility of the system.

In certain embodiments of the invention, the cells are harvested. Cell harvest is typically accomplished by injecting cold buffer into the cartridge. In some embodiments of the invention, a Peltier device may be integrated under the cartridge to cool the cartridge down to somewhere between about 20° C. to about 30° C., which allows for release without the need to dilute the cells down in a greater fluid volume.

In some embodiments, the dendritic cells generated in the octagonal cartridge may be moved into a smaller cartridge. When manufacturing dendritic cell based immunotherapies, immature dendritic cells generated from the differentiation of monocytes (first step) are typically subject to additional steps (maturation and antigen pulsing). Conventionally, this is accomplished by performing the first step in multiple flasks or wells and then combining immature dendritic cells into a single flask or well. This type of concentration/consolidation allows for less use and subsequent waste of reagents used for maturation and antigen pulsing, which are expensive. In the present invention, the immature dendritic cells from the octagonal cartridge where the first step is performed are transferred to a smaller cartridge for maturation and antigen pulsing. In some embodiments of the invention, the maturation and antigen pulsing are carried out in the main cell culture cartridge and do not require use of a second cartridge.

Some embodiments of the present invention may use Luer Activated Valves (LAVs) for seeding and harvesting monocytes (MOs) and immature dendritic cells (iDCs), respectively. This improves the workflow so that cell solution is not lost during seeding/harvest. Syringes may be connected to the LAVs, such as in the MicroDEN systems. Syringes may be used as funnels to add MO solution (for seeding) and cold buffer (for harvest). The syringe may be used to "pipette" up and down to un-adhere and re-suspend iDCs due to turbulence caused by "pipetting" action. This "pipetting" up and down is actually pushing and pulling on the syringe plunger.

An example arrangement is now described in which systems and methods of the invention utilize one or more cell culture cartridges, each cell culture cartridge containing a cell culture chamber, configured to be fluidically coupled to one another for carrying out the processing of a patient's cellular material to generate an immunotherapeutic product. It is to be understood that the cell culture cartridges are provided in a closed environment in certain embodiments. Scale-up of this example embodiment will be within the knowledge of the skilled artisan by adding modules (e.g., cell culture cartridges) to allow for serial and/or parallel processing. The skilled artisan will also appreciate that different or alternative arrangements may be desired based on the product to be produced.

In certain embodiments, one or more pumps are operably coupled to the cell culture chamber for perfusing perfusion medium into the cell culture chamber. Perfusion medium comprises any suitable medium. In some embodiments, the perfusion medium is differentiation medium. The cell culture cartridge can also include one or more fluid reservoirs. The fluid reservoirs are in fluidic communication with the cell culture chamber and can be operably coupled to one or more pumps. One or more tubes for connecting the fluid reservoirs to the pumps and cell culture chamber are also provided. In certain aspects, the one or more pumps are configured for pumping fluid from the fluid reservoir, through the cell culture chamber, and into the waste collection reservoir. In an embodiment, fluid moves from the fluid reservoir, through tubing to the pump and into the cell culture chamber via inlet, back out of the cell culture chamber via outlet, through tubing, and into the waste collection reservoir.

In certain embodiments, the fluid reservoir and/or waste collection reservoir can each be provided as one or more capped bottles either contained within the cell culture chamber or fluidically coupled to the chamber. Each reservoir contains an inlet port and an outlet port, or an outlet port and a vent fluidically coupled to the inlet of one or more cell culture chambers. In certain aspects, for example, Luer connectors and silicone gaskets cut to fit around the Luer connectors can be used to prevent leakage through either or both of the inlet or outlet.

In certain embodiments, the one or more cell culture cartridges are sized and configured to fit within an incubator, such that the process will be carried out within an incubator. Conditions within the incubator include sustained temperatures of 37° C. and 95-100% relative humidity. Thus, the materials chosen must have the integrity to withstand these conditions, given that the materials (including fluids and biologics) tend to expand under such conditions. Furthermore, in some circumstances, conditions within the incubator remain stable, and automated recording of the temperature is possible to have knowledge of temperature fluctuations to correlate with any aberrations in the reactions performed in the incubator. Accordingly, any supply of power should not change the environment within the incubator. For example, certain pumps generate heat.

Accordingly, in one embodiment, the pumps are housed separately from the cell culture cartridge, but are still in fluidic and operable communications with the cell culture cartridge. In another embodiment, the pumps are directly attached to the cell culture cartridge and located within the incubator, but are heat free or are operably connected to a heat sink and/or a fan to dissipate the heat. Regardless of the configuration, the pumps are operably coupled to the cell culture cartridge, and, in turn, the cell culture chambers. Additional details regarding perfusion-based automated cell culture systems, such as small scale culture system for endothelial cell culture with on-board reagent storage and perfusion enabled by an on-board disposable peristaltic pump and a larger scale culture system for dendritic cell generation from monocytes using chambers with polystyrene bottom surfaces, can be found in International Patent Application Numbers PCT/US2016/040042 and PCT/US2016/60701, both of which are incorporated herein by reference in their entirety.

This system can also include a heater for controlling the temperature of the cell culture reservoir and optionally the fluid reservoir. In such a configuration, no incubator is required, and the system can operate autonomously, with only a source of electrical power. If the system lacks a heater, it can be operated inside of a cell culture incubator. Some embodiments of the invention comprise a carbon dioxide ($CO_2$) environment for medium buffer.

In still other aspects, the cell culture chamber includes one or more sensors (not shown) operably coupled to the cell culture chamber. The sensors may be capable of measuring any suitable parameters. For example, the sensors may be capable of measuring one or more parameters within the cell culture chamber, such as pH, dissolved oxygen, total biomass, cell diameter, glucose concentration, lactate concentration, and cell metabolite concentration. In embodiments wherein the system includes multiple cell culture chambers, one or more sensors can be coupled to one or more of the cell culture chambers. In certain embodiments, one or more sensors are coupled to one or more cell culture chambers, but not all of the chambers in a system. In other embodiments, one or more sensors are coupled to all of the cell culture chambers in a system. In systems having multiple chambers operably coupled to one or more sensors, the sensors can be the same in each of the chambers to which they are coupled, they can all be different, or some sensors can be the same and some can be different. In certain aspects, the one or more sensors are operably coupled to a computer system having a central processing unit for carrying out instructions, such that automatic monitoring and adjustment of parameters is possible. Additional details regarding computer systems for implementing methods of the present invention using the cell culture chambers is provided below.

In certain embodiments, the cell culture chamber has an inlet and an outlet, both of which can be used to fluidically couple the chamber via a fluidic connector with one or more additional vessels. In certain embodiments the additional vessels include one or more additional cell culture chambers. Systems of the present invention can include, for example, 2, 3, 4, 5, 6, 7, 8, 9, 10, 15, 20, 30, 40, 50, 60, 70, 80, 90, 100, or any number of cell culture chambers in between or higher than one hundred configured to fluidically connect with one another in a series to produce the immunotherapeutic product. Alternatively or additionally, one or more cell culture chambers can be arranged in parallel with one another to allow for production of immunotherapeutic product for more than one individual at a time. In a preferred embodiment, the cell culture chambers of the cell culture cartridge are connected via a sterile connection.

The system and some or all of its components can be designed using CAD software and then transferred to a laser cutter, which allows the plastic to be cut to the specified size and shape. The various connections, such as inlets and outlets, can be made by laser cutting through holes which can then be then tapped manually to provide threads for accepting male Luer fittings. Fluid can later be introduced to the system by connecting the Luer adapter to a blunt dispensing needle with tubing pushed onto the blunt needle portion. Additional detail regarding construction of fluidic system components can be found in International Patent Application Numbers PCT/US2016/040042 and PCT/US2016/60701, both of which are incorporated herein by reference in their entirety. The system and some or all of its components can also be produced using injection molding.

The above description focuses on the system components and various possible configurations. The following description focuses on the processes that are carried out using example embodiment systems of the invention. In order to stimulate and expand antigen-specific T-cells, the process begins with a co-culture of T-cell containing cells with APCs obtained from the same individual in a cell culture chamber. In a particular embodiment, the T-cell containing cells include peripheral blood mononuclear cells (PBMCs) and the APCs include DCs. The T-cell containing cells and APCs can be provided to the cell culture chamber in a ratio (T-cell containing cells:APCs) from about 1000:1 to 1:1000 of about, such as, for example and not limitation, 1000:1, 900:1, 800:1, 700:1, 600:1, 500:1, 400:1, 300:1, 200:1, 100:1, 75:1, 50:1, 25:1, 20:1, 15:1, 10:1, 5:1, 4:1, 3:1, 2:1, 1:1, 1:2, 1:3, 1:4, 1:5, 1:6, 1:7, 1:8, 1:9, 1:10, 1:15, 1:20, 1:50, 1:75; 1:100, 1:200: 1:300, 1:400, 1:500, 1:600, 1:700, 1:800, 1:900, 1:1000, or any ratio therebetween. In one aspect, a ratio of 10:1 is preferred.

In order to initiate stimulation and expansion of T-cells from the interaction of APCs with T-cell containing cells, the APCs need to be stimulated. This can be done through the use of one or more stimulatory molecules. In certain embodiments, the stimulatory molecule is non-tumor specific. In other embodiments, the stimulatory molecule is tumor specific. For example, the stimulatory molecule can be chosen from one or more characteristics of an individual's tumor, such as different antigen peptides. In some embodiments, the stimulatory molecule is preferably added only in the beginning of a culturing cycle. The stimulatory molecule can be added over a period of only about a few minutes, an hour, a few hours, or longer. In one preferred embodiment, the stimulatory molecules are added over about an hour time period.

During culturing of the two cell materials, a supernatant is formed containing lighter non-adherent T-cells, whereas the heavier, mature APCs (e.g., dendritic cells) adhere to or reside on the bottom surface. In those embodiments wherein DCs are used as the APCs, the expanded T-cells must be extracted from the cell culture chamber by the end of the seven days because primary DCs cannot be maintained for more than seven days in culture. Thus, if additional expansion of T-cells is desired, a fresh supply of dendritic cells is needed. It is also to be understood that the culturing of cells using one batch of dendritic cells can be for any period of time less than seven days. For example, the cells can be cultured for a period of anywhere from less than a minute to seven days, with the duration of culture dependent on the extent of stimulation desired.

In an example embodiment, after up to seven days in culture, the expanded T-cells are extracted and transferred to a new cell culture chamber containing fresh DCs pulsed with, for example, the same antigen peptides used in the first cell culture chamber. The stimulation process can be repeated as many times as needed in order to generate a sufficiently large number of cells for a therapeutic dose of T cells. When using a culture surface area comparable to that of typical well plates, the stimulation process is typically repeated four times to generate a sufficient supply of T-cells.

The co-culturing of APCs and T-cells takes place in a culture medium. Example culture media include, but are not limited to, RPMI medium, and DC medium sold under the trademark CELLGENIX by CellGenix Inc. (Portsmouth, NH). Any other suitable culture medium known in the art can be used in accordance with embodiments of the present invention. Cytokines such as IL-4 and GM-CSF can also be added to the culture medium.

In one embodiment, a perfusion of medium and cytokines can be provided to the cellular mixture within the cell culture chamber(s) to assist with the formation of the cell-based immunotherapeutic product. In plate-based protocols for stimulation of T cells by DCs, a culture volume of approximately 2 mL is maintained from the start, with infusion of cytokines occurring twice within each 7 day stimulation period. A major advantage of perfusion is the ability to maintain consistent local concentration profile of medium and cytokines, which ensures greater yields and the potential ability to speed up the process of monocyte differentiation to DCs compared to prior art plate-based protocols. However, the combination of adherent (DC) and non-adherent (T cell) types, along with the high sensitivity of DCs to mechanical forces poses challenges to the stimulation and expansion of antigen-specific T-cells, especially with respect to the flow of fluid through the cell culture chamber. Thus, in those embodiments in which medium and cytokines are provided via perfusion, systems of the present invention must be able to supply cells with nutrients and cytokines without removing cells from the cell culture cartridge while also taking into account the shear sensitivity of certain antigen-presenting cells, such as DCs. Essentially, some embodiment systems and methods of the invention aim to optimize retention of autocrine/paracrine signals favoring T cell proliferation while refreshing growth factors and maintaining minimal physical stimulation of DCs. In order to account for this, both the direction and the rate of perfusion flow through the cell culture chamber must be taken into consideration. For example, some embodiments of the invention may comprise medium flow arrangement other than unidirectional flow, such as counter-current medium flow arrangement.

In certain aspects, the fluid flow rate is maintained below the sedimentation rate of the antigen-presenting cells. As such, the antigen-presenting cells will remain within the culture chamber because of their mass. In other words, the antigen-presenting cells will sink toward the bottom of the cell culture chamber and therefore remain in the cell culture chamber.

In other aspects, the plurality of inlets and the outlet of the cell culture chamber are arranged to move fluid, such as perfusion fluid, within the cell culture chamber along a vertical flow path. This configuration helps to prevent cells (e.g., both DCs and T-cells) from leaving the chamber, especially when flow rates through the chamber are in the range of 2-10 mL/min. A configuration with symmetric inflows and vertical outflow prevents cells from leaving the chamber. As shown in at least FIG. 1, certain embodiments of the cell culture cartridge of the present invention have eight inlets and one vertical outlet.

Although shown in FIG. 1 as having eight inlets and one vertical outlet, any number of inlets and outlets can be provided, as long as the fluid flowing out of the chamber flows in the vertical direction out of the top of the chamber and flows in symmetrical fluid channels within the chamber. For example, the chamber can have any one of 1, 2, 3, 4, 5, 6, 7, 8, 9, 10, or more perfusion fluid inlets and/or outlets.

In certain aspects, medium perfusion occurs at specific points in time over the time period in which the cells are cultured in any one cell culture chamber, such as, for example, 1, 2, 3, 4, 5, 6, 7, 8, 9, 10, or more times each day or week. In other aspects, medium is continuously perfused during culturing. Continuous perfusion helps to maintain a near constant culture volume throughout the process.

In certain aspects, cytokines are infused at one or more points during culturing, such as, for example, 1, 2, 3, 4, 5, 6, 7, 8, 9, 10, or more times. Alternatively, cytokines can be continuously perfused with medium. In those embodiments, the continuous perfusion helps maintain a consistent local concentration profile of cytokines, which can help to ensure greater yields and has the ability to increase the speed at which T-cells are stimulated and expanded compared to static cell culture methods.

Perfusion parameters can be varied at any time during a culture cycle. Example parameters include, but are not limited to, the median flow rate, cytokine concentration, and duration of culture cycle. Each of these parameters may have an impact on the efficacy of T-stimulation. For example, in recent work designing culture chambers for monocyte-diffusion to DCs, as described in International Patent Application Nos. PCT/US2016/040042 and PCT/US2016/60701, medium perfusion rates corresponding to wall shear stress levels of 0.1 dyn/cm$^2$ were determined to be capable of producing DCs that are phenotypically identical to those generated using conventional 6- or 24-well plate-based protocols. As such, by measuring the one or more of the phenotypic and functional measures described above during the culture cycle, the effect of one or more perfusion parameters on efficacy can be monitored, allowing for appropriate adjustments.

In accordance with certain aspects, the stimulation efficacy can be assessed at any point during the culturing, preferably after seven days. Both phenotypic and functional measures can be used to assess the efficacy. For example, cell number (fold-expansion) can be calculated using directed cell counting methods. Cell phenotype, including assessment of antigen-specificity by tetramer staining, can be characterized by flow cytometry. Functional assays can also be used to assess the ability of expanded T cells to recognize antigen-loaded target cells as well as autologous tumor cell. The results can be benchmarked against DC-based T cell stimulations carried out in both 24-well plate and G-Rex® formats.

As described above, because certain APCs, such as dendritic cells, cannot survive in culture beyond seven days, certain embodiments of the present invention involve multiple cycles of T-cell stimulation using more than one cell culture cartridge in semi-batch configurations. Each cycle is performed with freshly generated autologous antigen-presenting cells. In certain embodiments, the antigen-presenting cells are pulsed with the same set of antigens for each stimulation cycle. In other embodiments, different sets of antigens are used for one or more of the stimulation cycles.

In general, multiple cycle T-cell stimulation involves the culturing of cells in a first cell culture chamber in a manner that generates a supernatant comprising a first cell product, the provision of a second cell culture chamber, and the subsequent transfer of supernatant from the first cell culture chamber to the second cell culture chamber by introducing a gas flow into the first cell culture chamber.

For example, in certain embodiments, a cell culture system is provided that includes a cell culture chamber and a central processing unit comprising memory containing instructions executable by the central processing unit. In certain aspects, the instructions cause the system to receive as a first input data comprising a size of the cell culture chamber, receive as a second input data comprising a first concentration of a first cell type and a second concentration of a second cell type in one or more fluids that will be introduced into the cell culture chamber, and calculate, based on the first and second inputs, a perfusion rate of a perfusion fluid that will be introduced into the cell culture chamber that maximizes a probability of the first cell type and the second cell type contacting each other within the cell culture chamber.

In some aspects, the system also includes one or more pumps operably coupled to one or more perfusion fluid reservoirs and operably coupled to the central processing unit, such that the central processing unit also controls the perfusion rate of the perfusion fluid by controlling the one or more pumps.

In certain embodiments, systems and methods of the invention utilize modules (e.g., cell culture cartridges and systems thereof containing cell culture chambers, etc.) that are fluidically coupled to one another for processing an individual's cellular material to produce an immunotherapeutic product. Systems, or devices, of the invention are modular and capable of fluidic connection to other similar devices in series (i.e., with fluid flowing from one device into another) and/or in parallel, and may also be so configured as to physically stack with one another or be capable of physical arrangement within a related device such as an incubator. The modular design of the system specifically allows for modules to be flexibly switched in and out depending on a desired process to be included within the system.

Fluidic devices of the invention, including the cell culture cartridges comprising cell culture chambers, can be provided in either a microfluidic embodiment (i.e., wherein one or more channels or chambers therein has a dimension in the range of from about 1 µm to about 999 µm) or a macrofluidic embodiment (wherein all of the channels or chambers therein have dimensions of about 1 mm or more), or both.

The fluidic devices can further include additional fluid channels or compartments, gaskets or seals, mixing zones, valves, pumps, vents, channels for pressurized gas, electrical conductors, reagents, ports, and tubing as required by a particular design. They also may contain one or more control modules, transmitters, receivers, processors, memory chips, batteries, displays, buttons, controls, motors, pneumatic actuators, antennas, electrical connectors, and the like. The devices preferably contain only materials that are nontoxic to mammalian cells and that are compatible with sterilization by the use of alcohol and/or heat or other means, such as exposure to gamma radiation or ethylene oxide gas.

The materials of equipment are chosen with the appropriate chemical compatibility under different temperature and pressure rating specific to each process. Additionally, the choice of pumps implemented in the device, such as syringe, peristaltic, pressure, and rotary pump, ranges from a nL to a mL in flow rates and 10 to 10,000 psi in pressure depending on the flow and pressure requirements for the different functions.

Systems of the invention can also include one or more sample solution reservoirs or well or other apparatus for introducing a sample to the device, at various inlets of the modules, which are in fluid communication with an inlet channel. Reservoirs and wells used for loading one or more samples onto the fluidic device of the present invention includes but are not limited to, syringes, cartridges, vials, eppendorf tubes and cell culture materials (e.g., 96 well plates).

Where useful, surfaces of the devices can be made more hydrophilic, such as by exposure to a plasma, or can be coated with one or more gels, chemical functionalization coatings, proteins, antibodies, proteoglycans, glycosaminoglycans, cytokines, or cells. In an embodiment, the cell culture cartridge and system are located at a centralized site. The equipment is single-use, i.e., patient material is processed within bags, tubing, and cell culture vessels that are used only for a single patient's cells.

Fluidic devices of the invention are preferably devoid of fluid leaks under operating conditions and capable of sterile operation over a period of days to weeks. Fluidic devices of the invention also include a sampling mechanism that allows fluid to be removed from the system for testing without introducing new material or contaminants to the system.

In certain aspects, at least part of the cell culture system comprises disposable components, some or all of which can be housed within a non-disposable frame or console. In other aspects, all components of the system are disposable. Furthermore, in some embodiments, the cell culture system includes a sample tracking component for tracking and documenting patient material. In an embodiment, the cell culture cartridge and system are located at a centralized site. The equipment is single-use, i.e., patient material is processed within bags, tubing, and cell culture vessels that are used only for a single patient's cells.

At least one step, and sometimes a plurality or all steps, during the manufacturing process are monitored for product characteristics (e.g., purity and polymorphic forms) using a variety of inline process analytical tools (PAT) or miniaturized micro-total analysis system (micro-TAS).

As described above, the cell culture systems of the present invention are capable of controlling the direction and flow of fluids and entities within the system. Systems of the invention can use pressure drive flow control, e.g., utilizing valves and pumps, to manipulate the flow of cells, reagents, etc. in one or more directions and/or into one or more channels of a fluidic device. However, other methods may also be used, alone or in combination with pumps and valves, such as electro-osmotic flow control, electrophoresis and dielectrophoresis (Fulwyer, Science 156, 910 (1974); Li and Harrison, Analytical Chemistry 69, 1564 (1997); Fiedler, et al. Analytical Chemistry 70, 1909-1915 (1998); and U.S. Pat. No. 5,656,155, each of which is incorporated herein by reference).

Systems of the invention can also include or be operably coupled to one or more control systems for controlling the movement of fluid through the system; monitoring and controlling various parameters, such as temperature, within the systems; as well as detecting the presence of cell-based immunotherapeutic products, quantity of product (directly or indirectly), conversion rate, etc. The system may also be equipped with numerous classes of software, such as an advanced real-time process monitoring and control process, allowing for feedback control, as well as processes that allow integration and scale-up given reaction and purification results obtained using the system.

In certain embodiments, the system includes a combination of micro-, milli-, or macro-fluidic modules and tubing that are interchangeable in terms of channel dimensions, flow geometry, and inter-connections between the different modules of the device. Each module and tubing may be designed for a specific function. In one embodiment, all of the modules within the system are designed for cell culturing and T-cell stimulation. In other embodiments, the modules with the system are designed for different functions, such as tissue processing, dendritic cell generation, cell culturing, concentration, and/or purification, all integrated for the continuous manufacturing of an immunotherapeutic product. Both homogenous and heterogeneous processes are considered which are suitable for flow application. These processes are designed and optimized with respect to the starting materials and operating conditions, such as temperature, pressure and flow rates so as to not readily clog the system during the flow process.

The method of device scale-up is performed by parallel addition of module reactors or enlargement of the module channels while maintaining a set of dimensionless parameters characteristic to each process constant and dimensional parameters within the upper and lower bound limit. During process integration and optimization, the process decision variables, including temperature, pressure, flow-rate and channel dimensions, are varied to achieve the desired trade-off between yield, purity and throughput. Throughout the optimization process, the aforementioned set of dimensionless parameters undergoes an algebraic optimization with operational constraints. The operational constraints are the lower and upper bound of the decision variables. The objective function considers a combination of purity, yield and throughput operating variables. While the dimensionless parameters determine the steady-state quality of the device, the start-up quality of the device is also useful as it determines the time required to reach steady state and, in turn, the productivity of the device in the form of lag-time and waste. The start-up dynamics are analyzed using both simulation and experimentation, the results of which are used to perform a start-up optimization by implementation of real-time feedback control.

Aspects of the present disclosure described herein, such as control of the movement of fluid through the system, as described above, and the monitoring and controlling of various parameters, can be performed using any type of computing device, such as a computer or programmable logic controller (PLC), that includes a processor, e.g., a central processing unit, or any combination of computing devices where each device performs at least part of the process or method. In some embodiments, systems and methods described herein may be performed with a hand-held device, e.g., a smart tablet, a smart phone, or a specialty device produced for the system.

Methods of the present disclosure can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. Elements of computer are a processor for executing instructions and one or more memory devices for storing instructions and data. Generally, a computer will also include, or be operatively coupled to receive data from or transfer data to, or both, one or more non-transitory mass storage devices for storing data, e.g., magnetic, magneto-optical disks, or optical disks. In some embodiments, sensors on the system send process data via Bluetooth to a central data collection unit located outside of an incubator. In some embodiments, data is sent directly to the cloud rather than to physical storage devices. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTMLS, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to embodiments of the invention involves transforming a tangible, non-transitory, computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

As one skilled in the art would recognize as necessary or best-suited for performance of the methods of the invention, a computer system or machines employed in embodiments of the invention may include one or more processors (e.g., a central processing unit (CPU) a graphics processing unit (GPU) or both), a main memory and a static memory, which communicate with each other via a bus.

Figure 19:
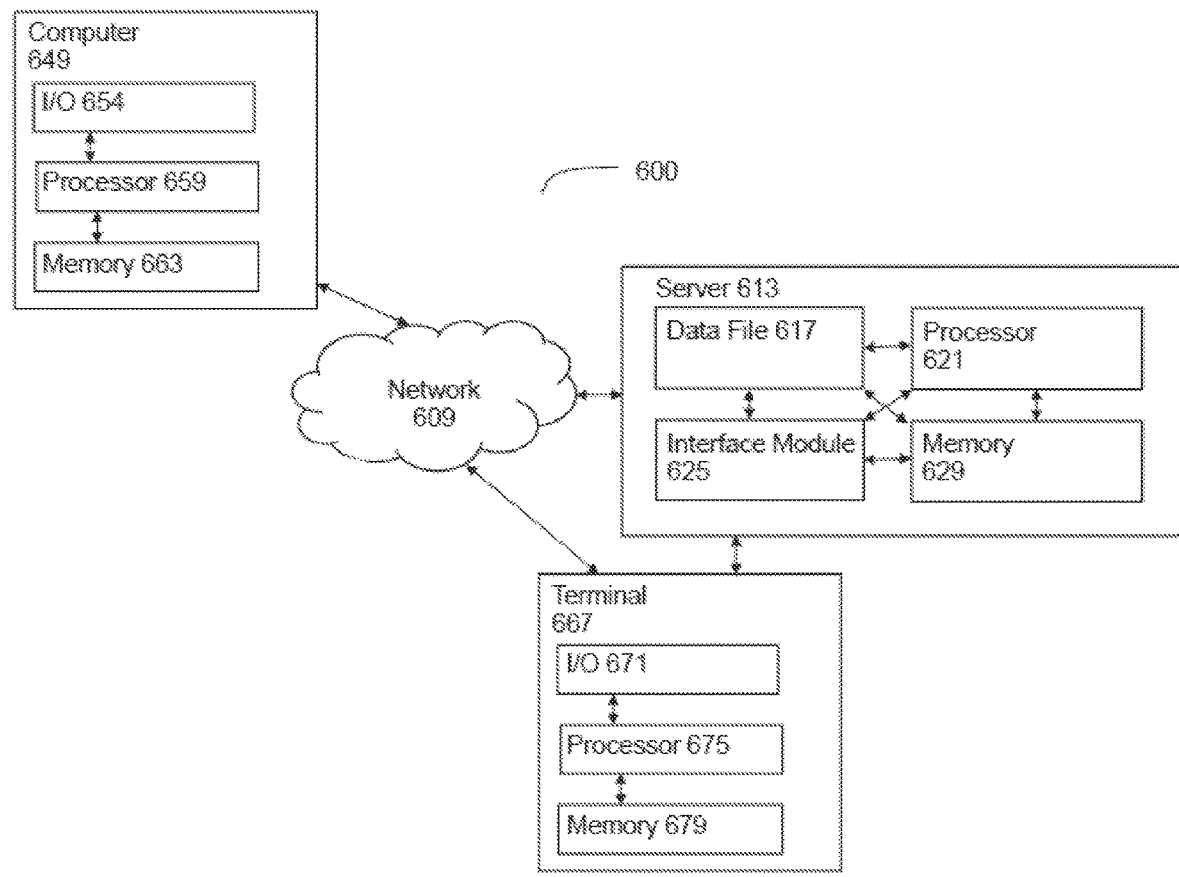
FIG. 19 depicts a system of the invention in accordance with certain embodiments.

In an example embodiment shown in FIG. 19, system 600 can include a computer 649 (e.g., laptop, desktop, or tablet). The computer 649 may be configured to communicate across a network 609. Computer 649 includes one or more processor 659 and memory 663 as well as an input/output mechanism 654. Where methods of the invention employ a client/server architecture, operations of methods of the invention may be performed using server 613, which includes one or more of processor 621 and memory 629, capable of obtaining data, instructions, etc., or providing results via interface module 625 or providing results as a file 617. Server 613 may be engaged over network 609 through computer 649 or terminal 667, or server 613 may be directly connected to terminal 667, including one or more processor 675 and memory 679, as well as input/output mechanism 671.

System 600 or machines according to example embodiments of the invention may further include, for any of I/O 649, 637, or 671 a video display unit (e.g., a liquid crystal display (LCD) or a cathode ray tube (CRT)). Computer systems or machines according to some embodiments can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 663, 679, or 629 according to example embodiments of the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

Effect of Monocyte Seeding Density on DC Generation

Dendritic cells (DCs) are increasingly important for research and clinical use, but obtaining sufficient numbers of dendritic cells is a growing challenge. The effect of monocyte (MO) seeding density on the generation of monocyte-derived immature DCs (iDCs) was investigated in a perfusion-based culture system of the present invention, as well as 6-well plates. Cell surface markers and the ability of the iDCs to induce proliferation of allogeneic T cells were examined. The data shows a strong relationship between iDC phenotype, specifically CD80/83/86 expression, and T cell proliferation. Cell culture systems of the invention-generated iDCs proved better than well plate generated iDCs at inducing T cell proliferation within the 200k-600k MO/cm$^2$ seeding density range studied. This may be attributed to perfusion in cell culture systems of the invention which supplies fresh differentiation medium continuously to the differentiating MOs while concurrently removing depleted medium and toxic byproducts of cellular respiration. Cell culture systems of the invention generated fewer iDCs on a normalized basis than the well plates at lower MO seeding densities but generated equivalent numbers of iDCs at 600k MO seeding density. The results demonstrate that cell culture systems of the invention are capable of generating greater numbers of iDCs with less manual work than standard well plate culture and the cell culture systems of the invention-generated iDCs have greater ability to induce T cell proliferation.

Dendritic cells are antigen-presenting cells that primarily reside in solid tissue and play an essential role in activating both the adaptive and humoral immune response. The primary function of dendritic cells (DCs) is to identify and capture foreign antigens that are a threat to the body, process them into smaller peptides, and present these peptides to naïve T or B cells. Upon antigen presentation, DCs can activate CD4$^+$ helper T cells and CD8$^+$ cytotoxic T cells as well as naïve and memory B cells. Additionally, DC s activate natural killer (NK) and natural killer T (NKT) cells. Given their ability to elicit a response from a variety of immune cells, DCs are an attractive target for therapeutic manipulation. Vaccines that contain antigen-loaded DCs for in vivo activation and expansion of T and B cells are used for infectious disease treatment and are being developed to specifically target cancerous cells in several clinical and pre-clinical research trials. Furthermore, DCs play a critical role in the emerging field of T cell based immunotherapies and are used to expand activated T cells in vitro.

Direct isolation of patient-specific DCs is a challenge since they reside in solid tissue and are present in very low concentration (<1%) in human blood. Therefore, DCs are often generated ex vivo from monocytes or stem cell precursors that can be readily isolated from circulating blood. In order to generate DCs for therapeutic manipulation, the standard method is to isolate peripheral blood mononuclear cells (PBMCs) from peripheral blood leukapheresis product, enrich CD14+ monocytes (MOs) through plastic adherence, elutriation, or positive selection by magnetic beads, followed by culture with IL-4 and GM-CSF for 5-10 days. Traditionally performed in well plates and T-flasks, this method requires numerous manual manipulations involving replenishment of differentiation medium throughout the culture duration. Generated immature DC (iDC) counts range from ca. 9-15 million and 6-20 million in a 6-well plate and T-175 flask, respectively; whereas, therapies may require ca. 150 million DCs for a single dose. Scaling up current DC generation techniques to manufacture relevant numbers of DCs required for clinical immunotherapies is challenging due to the need for numerous manual manipulations, large number of well plates/T-flasks required, and significant labor costs. Additionally, identifying optimal monocyte seeding density is a substantial challenge associated with scaling up the MO-to-iDC differentiation process and such information is difficult to ascertain from literature.

In order to overcome the aforementioned deficiencies of manual DC generation, an enclosed automated cell culture system was designed that generates DCs from monocytes with functionality similar to well plate generated iDCs. Cell culture systems of the invention incorporate a closed tubing and cell culture cartridge system that continuously perfuses fresh differentiation medium into the cartridge while simultaneously removing depleted medium and waste ($CO_2$ and lactate). This setup also reduces manual manipulation steps required for startup and media replenishment.

The effects of MO seeding density on iDC yield, phenotype, and functionality were examined. Three seeding densities were studied in cell culture systems of the invention and a 6-well plate control: 200,000 MOs/cm$^2$, 400,000 MOs/cm$^2$, and 600,000 MOs/cm$^2$. IDC yield increased in cell culture systems of the invention and remained constant in well plates as iDC seeding density increased. IDC yield in cell culture systems of the invention was lower than in well plates at 200k and 400k MO seeding densities and comparable to well plates at 600k MO seeding density. IDC phenotype showed strong dependence on MO seeding density in cell culture systems of the invention in which iDCs generated from a low seeding density induced greater T cell proliferation. Cell culture systems of the invention-generated iDCs that are phenotypically similar to iDCs generated in a 6-well plate, thereby corroborating previous research, and show that cell culture systems of the invention-generated iDCs induce greater T cell proliferation than well plate-generated iDCs.

A total of three identical experiments (N1, N2, N3) were systematically performed to evaluate the performance of cell culture systems of the invention. Each experiment consisted of three cartridges of the present invention (one cartridge per seeding density) and one or two 6-well plates (two to three wells per seeding density). MOs from a single donor were used for each individual experiment (N1, N2, or N3), requiring three total donors for iDC generation. T cells from a fourth donor were used for all allogeneic functional assays. CellGenix GMP DC medium was used as the base medium for MO-to-iDC differentiation. The medium was supplemented with 1% penicillin-streptomycin (Gibco 15140122) and 350 U/mL preclinical IL-4 and GM-CSF (CellGenix) for iDC generation.

Each MO-to-iDC differentiation experiment was 6 days in duration. All experiments were performed in a standard cell culture incubator maintained at 37° C. and 5% $CO_2$ at near saturation humidity. All work was performed under aseptic conditions in a laminar flow hood. All cell counts were conducted using a Countess II Automated Cell Counter.

Cell Culture Systems of the Invention

Experiments with cell culture systems of the invention were performed using the automated cell culture system previously described by our group. The polystyrene surface of each cell culture cartridge was treated with $O_2$ plasma for 90 seconds at 50 W power. Each cartridge had a polystyrene surface area of 39.7 cm2 and volume of ca. 12.7 mL. The perfusion rate of differentiation medium was 8.0 µL/min for the entire experiment duration. For each experiment, one cartridge of the present invention was used for each seeding density for a total of three cartridges. This required two pumping instruments since each instrument holds two cartridges. Previous experiments indicated that no cells were removed from the cartridge by the 8.0 µL/min medium perfusion over the course of the experiment, verified by centrifugation of the effluent followed by cell count.

At setup on Day 0, differentiation medium was added to the inlet bottle to allow for medium perfusion for 3 days. On Day 3 when the inlet bottle was nearly empty, fresh differentiation medium was added to allow for medium perfusion for an additional 3 days. Effluent was removed from the outlet bottle on Day 3. On Day 6, cells were harvested by aspirating the cell media and washing the cartridge 2 times with cold DPBS (4° C.). Adherent cells remaining after the two DPBS washes were not collected.

6-Well Plate

Corning Costar 6-well plates (3516) were used as a control for each experiment. A volume of 2.5 mL of differentiation medium was added to each well. Empty wells were filled with 3.0 mL of DPBS to minimize evaporation. On Day 3, 1 mL of fresh differentiation medium was added to each well. On Day 6, cells were harvested by aspirating the culture medium and washing each well 2 times with cold DPBS (4° C.). Adherent cells remaining after the two DPBS washes were not collected.

PBMC and MO/T Cell Isolation

Four units of whole blood (ca. 470 mL/unit) drawn from normal healthy donors were purchased from StemExpress. The blood was collected via venipuncture and processed on the same day. PBMCs were isolated using Ficoll density gradient medium and suspended in CryoStor CS10 cryopreservation medium at a concentration of ca. 50 million PBMCs per mL. Cells were cooled in a Mr. Frosty container at −80° C. for 12-24 hours then transferred to cryogenic LN2 storage for at least one week before resuscitation. MOs or T cells were enriched from PBMCs using Miltenyi Biotec CD14 or CD3 Microbeads and passed through two LS Columns.

Allogeneic T Cell Functional Assay

Allogeneic T cell functional assays were performed in a Corning Costar 24-well plate (3526) using 0, 200,000 (200k), or 500,000 (500k) iDCs generated in MicroDEN or a 6-well plate. Each well contained 1 million allogeneic T cells. CellGenix DCM was used as the base medium and was supplemented with 1% penicillin-streptomycin (Gibco 15140122) and 5% Human AB Serum (Sigma Aldrich H4522). T cells were stained with CellTrace Far Red to evaluate proliferation. The 24-well plate was covered in foil to protect from light and placed in the incubator (37° C. and 5% $CO_2$) for 5 days. At harvest, the cell solution was aspirated and the wells were washed 2 times with cold DPBS (4° C.) to collect remaining cells. Data was analyzed using FCS Express 6 Flow software.

Immunophenotyping

Flow cytometry was performed on an ACEA Biosciences NovoCyte instrument with 488 nm and 640 nm laser lines and four fluorescence channels. Cells were first stained with Fc Block (BD Biosciences 564220) for 10 minutes after viability staining and prior to antibody staining. Panel A tested viability (Live/Dead Fixable Green; Invitrogen L34970), CD209/DC-SIGN (R&D Systems FAB161P100), CD14 (Abcam ab157312), and CD45 (R&D Systems FAB1430A). Panel B tested CD80 (BD Biosciences 557226), CD83 (BD Biosciences 556855), CD86 (BD Biosciences 561128), and CD45. Panel C tested viability, HLA-DR (R&D Systems FAB4869P), CD11c (BD Biosciences 565227), and CD45 (R&D Systems FAB1430A). Panel D tested viability, CD3 (BD Biosciences 555333), CD45 (BD Biosciences 340953), and CellTrace Far Red. Gates were set using a CD209 isotype control (R&D Systems IC0041P) for Panel A and fluorescence-minus-one (FMO) controls. Data was analyzed using FlowJo software.

Flow Cytometry Gating Strategy

Large cells were gated in the SSC-A/FSC-A plot followed by single cells in a FSC-A/FSC-H plot. Panel A: Viable/$CD45^+$ cells were gated then CD14/CD209 was plotted to determine iDC percentage based on the $CD14^-/CD209^+$ population. Panel B: Lymphocytes were gated on a CD45 histogram then CD80/83 and CD80/86 was plotted to determine iDC phenotype. Panel C: Viable/$CD45^+$ cells were gated then HLA-DR/CD11c was plotted to determine iDC phenotype. Panel D: Viable cells were gated followed by a CD3/CD45 plot to isolate T cells, then a CellTrace Far Red histogram to deconvolute T cell proliferation.

Three experiments (N1, N2, N3) were ran consecutively (beginning different days) and each experiment included 1 cartridge of the present invention and 2-3 wells of a 6-well plate at each MO seeding density. Viability and iDC immunophenotyping were performed via flow cytometry. Generated iDC count and iDC yield were calculated by:

Live iDCs Harvested=[Cells Harvested]×[Viable/CD45+Cells]×[CD209+/CD14−Cells]

iDC Yield=Live iDCs Harvested÷MOs Seeded iDC Phenotype

Figure 20:
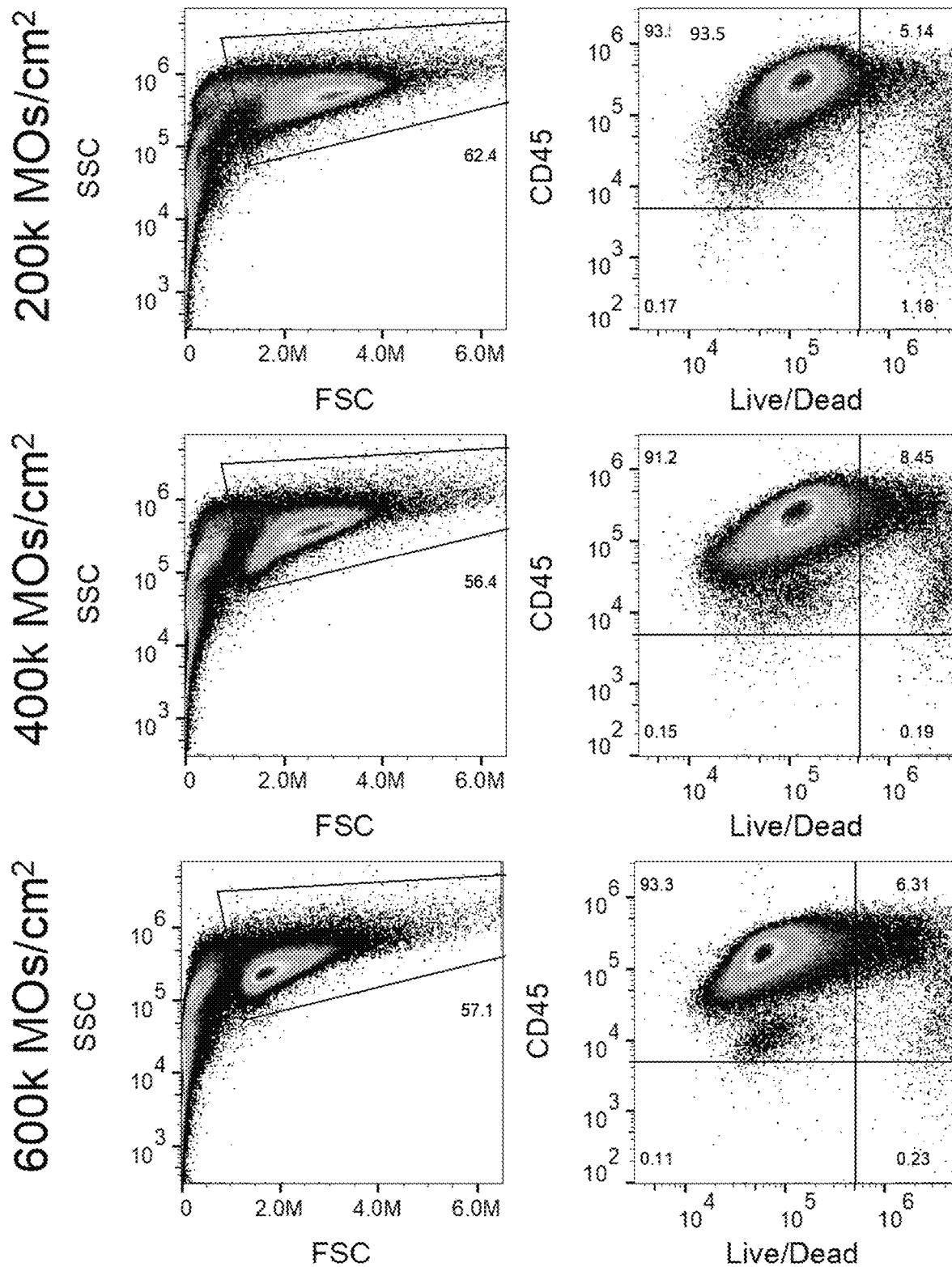
FIG. 20 shows MicroDEN N3 iDC phenotype. Data for experiments N1-N2 are shown in FIGS. 28 and 30.
Figure 20:
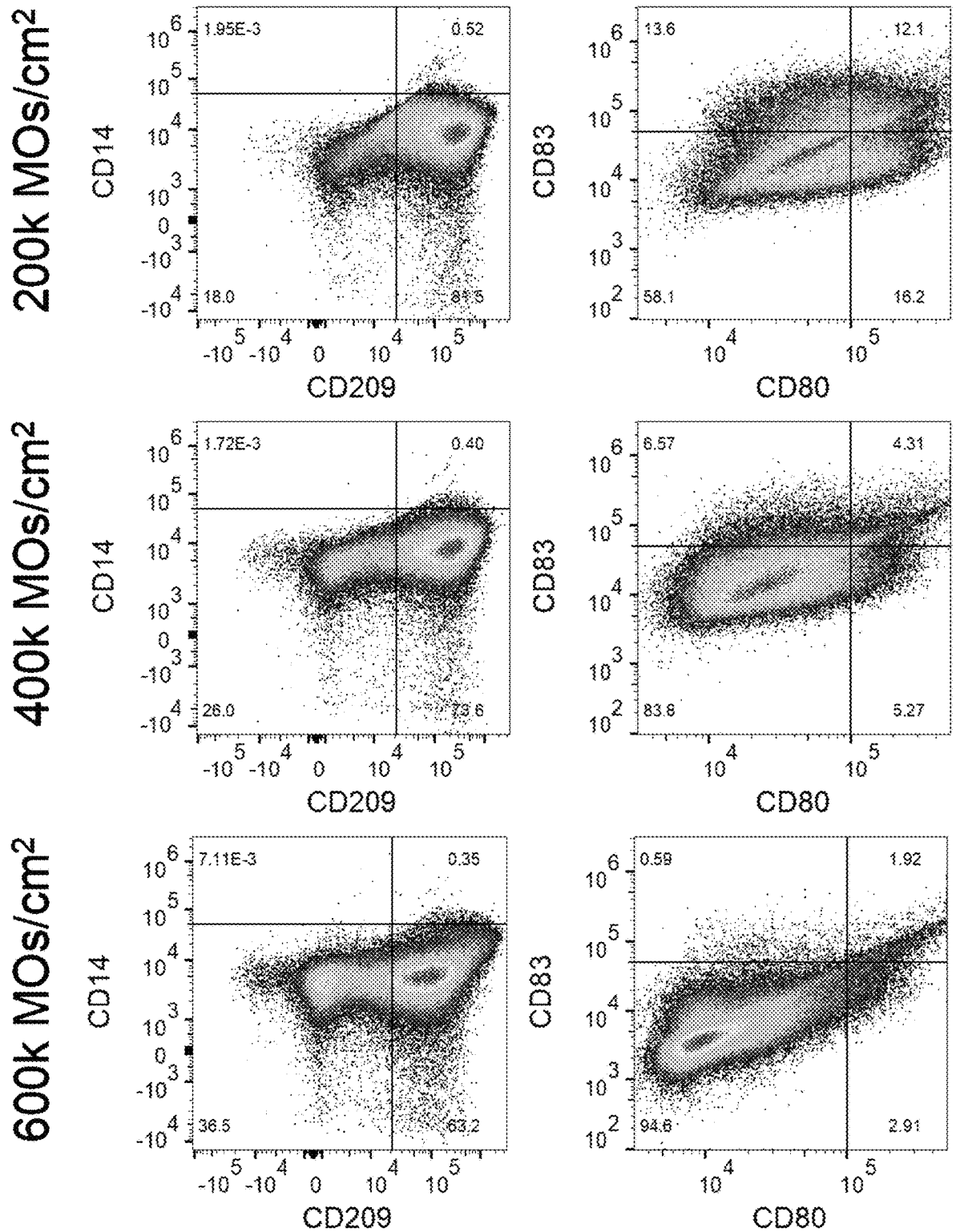
Figure 20:
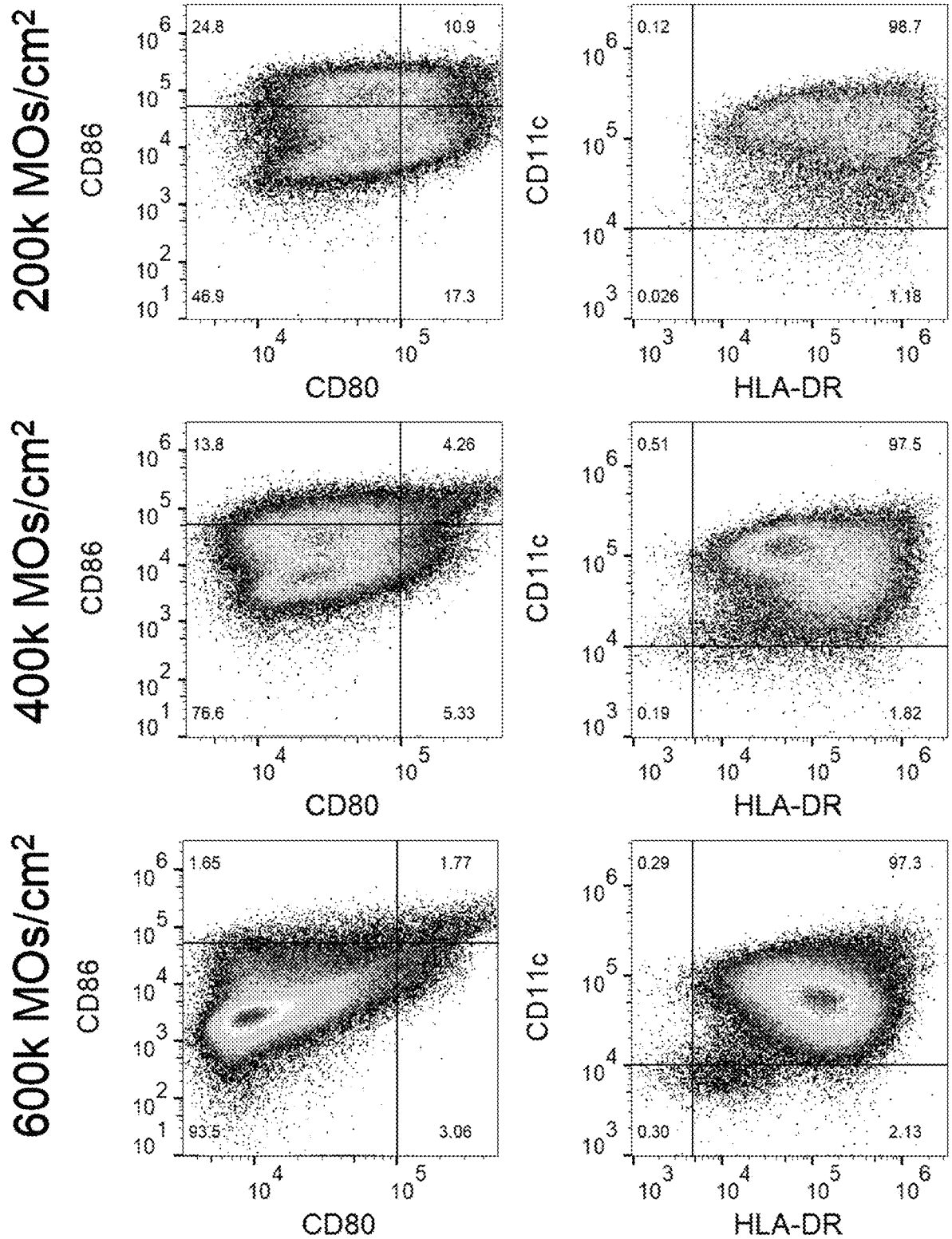
Figure 21:
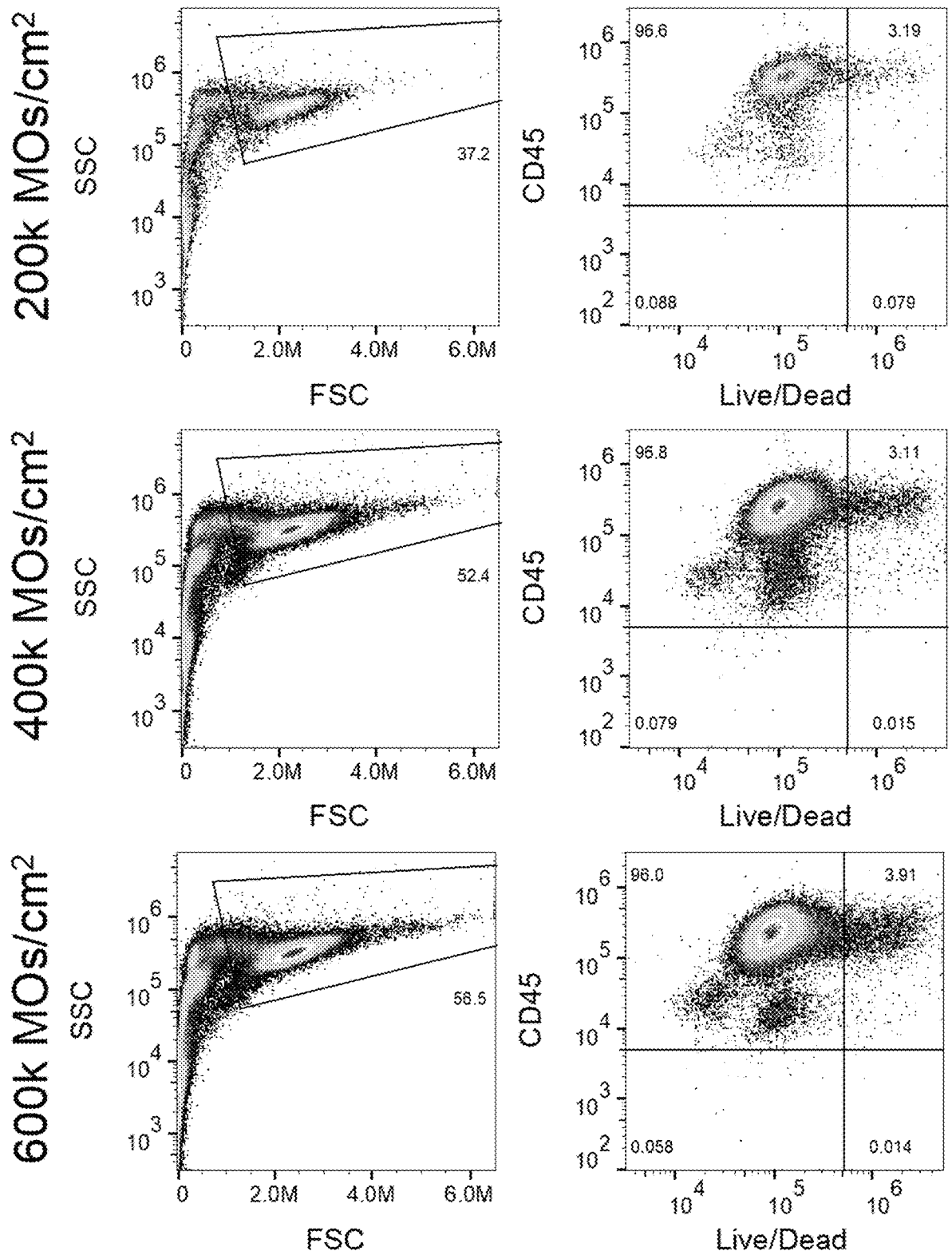
FIG. 21 shows 6-well plate N3 iDC phenotype. Data for experiments N1-N2 are shown in FIGS. 29 and 31.
Figure 21:
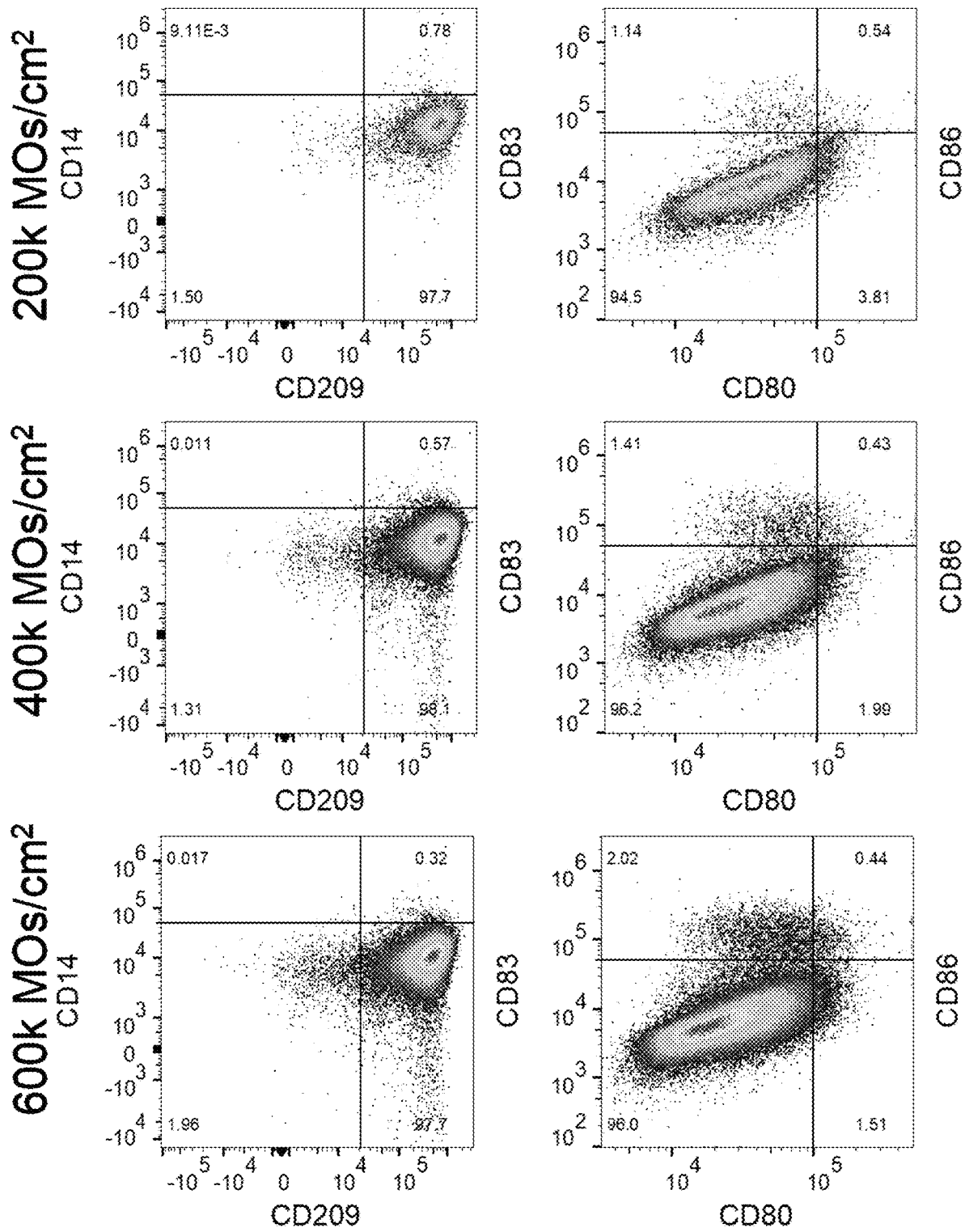
Figure 21:
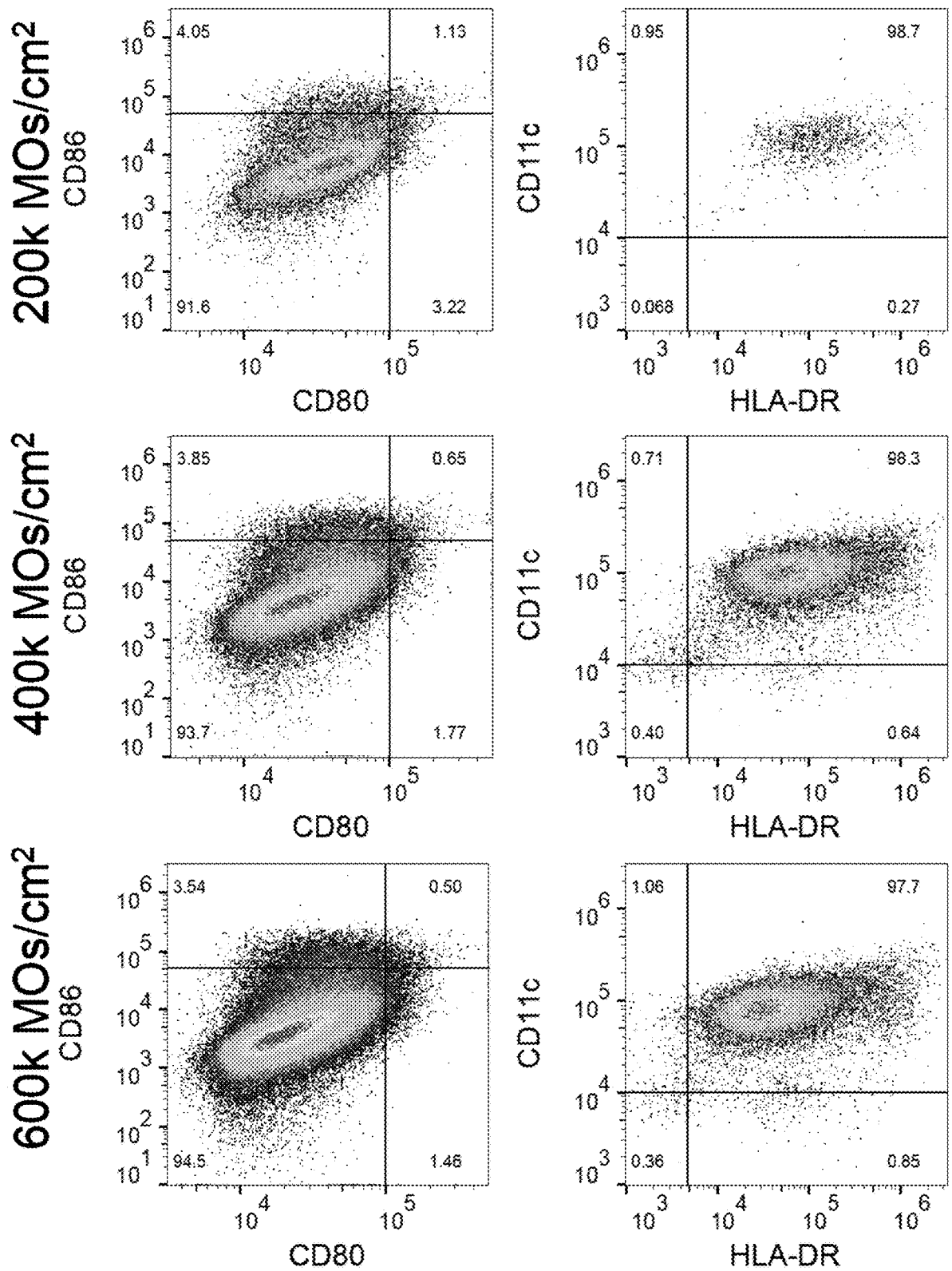

Cell culture systems of the invention and 6-well plate generated iDCs were phenotypically similar with subtle differences in CD209 (DC-SIGN)/80/83/86 expression that was dependent on MO seeding density. MO derived iDCs are $CD209^+$ and may have low CD14 expression depending on differentiation conditions. For this study, only $CD209^+$ $CD14^-$ cells were considered iDCs. FIGS. 20 and 21 show phenotype expression for cell culture systems of the invention and 6-well plate generated iDCs, respectively, for experiment N3. Data from N1 and N2 are shown in FIGS. 28-32.

The viability of harvested cells was >90% and comparable between cell culture systems of the invention and 6-well plates for experiments N1 and N3. Experiment N2 has significantly lower viability, ca. 70-90% for cell culture systems of the invention and ca. 77% for well plates. There was no correlation between MO seeding density and viability and all harvested cells were CD45+ leukocytes. CD209 expression of iDCs did not show any dependence on MO seeding density in either cell culture systems of the invention or 6-well plates, although cell culture systems of the invention iDCs did have slightly less CD209 expression than well plate iDCs (indicated by the left shift of CD209 fluorescence) for experiments N1 and N3. Experiment N2 iDCs had similar CD209 expression in both cell culture systems of the invention and well plates.

A significant population of viable CD45+ cells harvested from cell culture systems of the invention were CD209$^-$. This CD209$^-$ population accounted for ca. 20-40% of harvested cells for experiments N1/N3 and ca. 2-7% for experiment N2. 6-well plates generated ca. 2-4% CD209$^-$ cells within all three experiments. There was no a clear trend between the CD209- population and MO seeding density although the 200k and 400k MO seeding densities yielded fewer CD209- cells than the 600k MO seeding density. The dichotomy between CD209- cells harvested from cell culture systems of the invention and 6-well plates may be due to perfusion in cell culture systems of the invention during differentiation under the conditions tested. Perfusion may play a role in slowing MO-to-iDC kinetics, potentially requiring longer differentiation duration or higher cytokine concentration to further differentiate this population into CD209+ iDCs. Cell culture systems of the invention generate iDCs that are less differentiated under certain conditions and believe that further optimization of differentiation conditions (i.e., differentiation duration and cytokine concentration, specifically IL-4 concentration) in cell culture systems of the invention is necessary.

There was a salient dependence of CD80/83/86 iDC expression on MO seeding density in cell culture systems of the invention. Well plate generated iDCs showed relatively constant CD83/86 expression and CD80 expression was greatest at 200k MO seeding density and decreased as seeding density increased. All iDCs in both cell culture systems of the invention and 6-well plates were HLA-DR+ and CD11c+. Collectively, the phenotypic expression of cells harvested from cell culture systems of the invention and well plates are indicative of MO derived iDCs. Cell culture systems of the invention generated iDCs are phenotypically similar to 6-well plate generated iDCs under similar conditions with slight differences at low MO seeding densities.

iDCs Harvested

Directly comparing the total count of harvested cells between cell culture systems of the invention and 6-well plates is not instructive because cell culture systems of the invention had a greater number of seeded MOs, thus the number of iDCs harvested normalized to either cell culture systems of the invention or well plate surface area and iDC yield is plotted in FIGS. 22-25 to allow for direct comparison. There was variability between each experiment (N1-N3) in both cell culture systems of the invention and well plates which is expected when using different donor cells for each experiment. CD209 (DC-SIGN) expression is typically high for MO derived iDCs and the relatively high percentage of CD209- cells generated in cell culture systems of the invention negatively impacts the number of iDCs harvested.

Table 1 shows experimental data for iDC generation experiments in cell culture systems of the invention and 6-well plates.

Normalized iDCs Harvested

Figure 22:
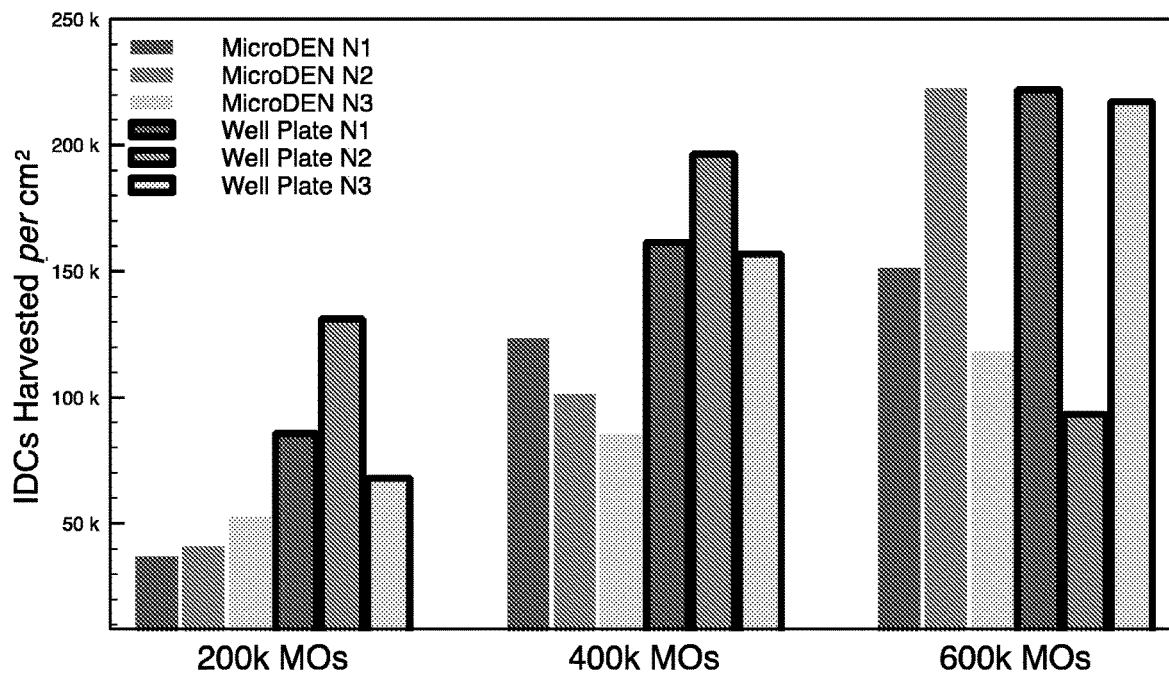
FIG. 22 shows differentiation data for iDCs generated in cell culture systems of the invention and 6-well plates, particularly harvested iDCs normalized to the surface area of the cartridge of the invention (39.7 $cm^2$) or 6-well plates (9.5 $cm^2$/well).
Figure 23:
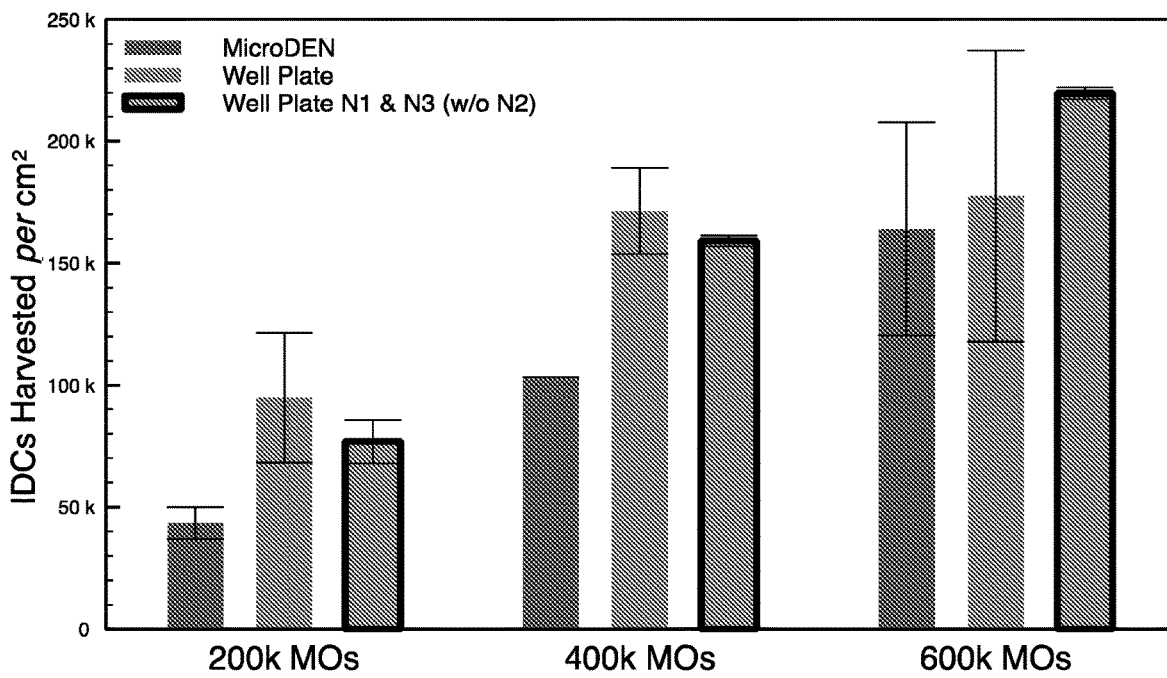
FIG. 23 shows differentiation data for iDCs generated in cell culture systems of the invention and 6-well plates, particularly average iDCs harvested normalized to the surface area of the cartridge of the invention or 6-well plates. Data presented as average±standard deviation of the indicated experiments. Data is tabulated in Tables 1-3.

FIGS. 22 and 23 show the number of iDCs harvested normalized to the cell culture surface area for each experiment and averaged data. Both cell culture systems of the invention and 6-well plates showed a positive correlation between MO seeding density and harvested iDCs on a "per cm$^2$" basis, indicating that more iDCs are generated when more MOs are seeded. At lower MO seeding densities, the well plates generated more iDCs per cm$^2$ than cell culture systems of the invention. At 600k MO seeding density, both cell culture systems of the invention and well plates generated similar numbers of iDCs per cm$^2$.

iDC Yield

Figure 24:
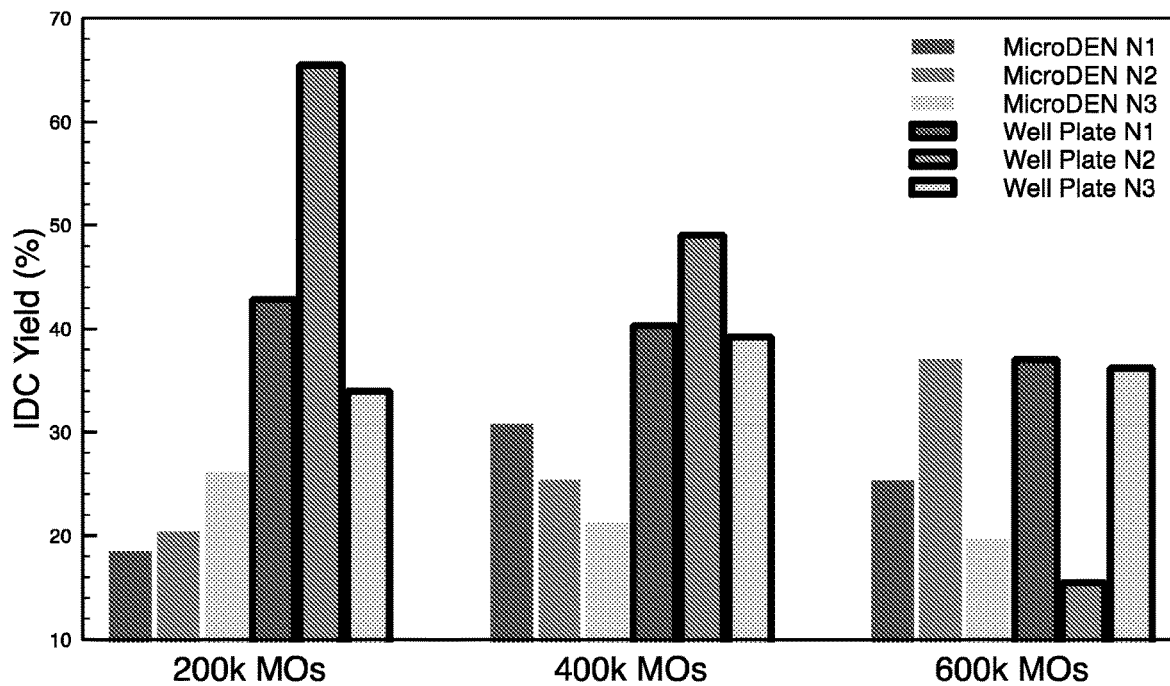
FIG. 24 shows differentiation data for iDCs generated in cell culture systems of the invention and 6-well plates, particularly IDC yield for each experiment at 200k-600k MOs/$cm^2$ seeding density.
Figure 25:
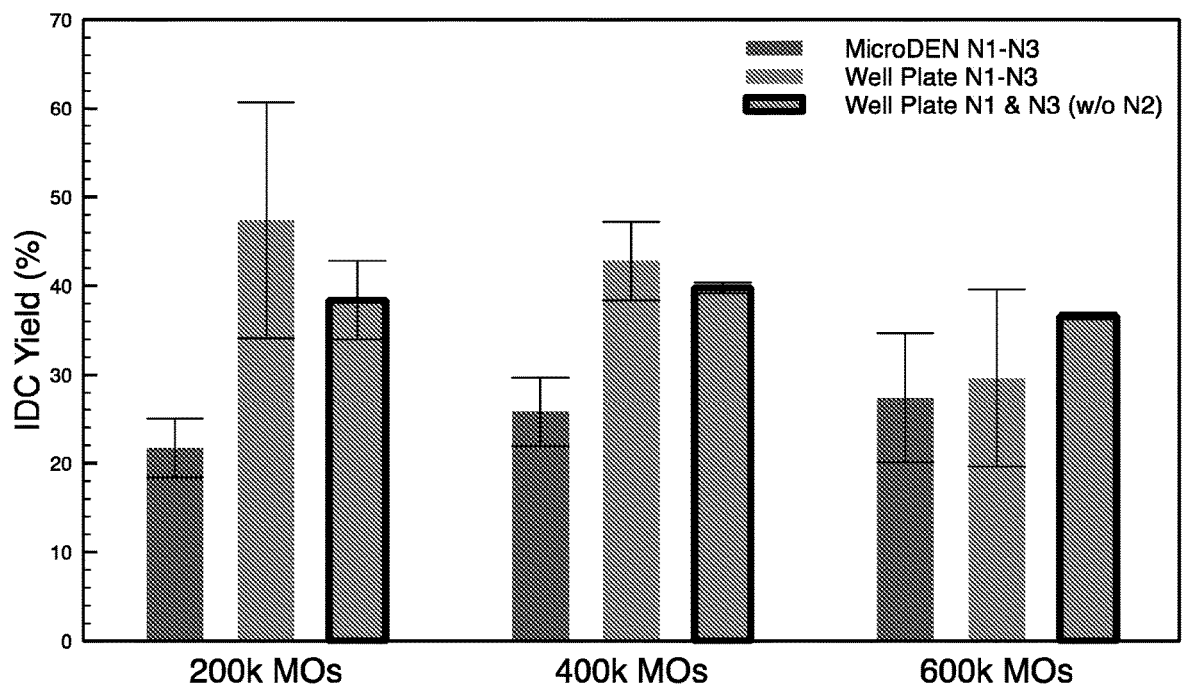
FIG. 25 shows differentiation data for iDCs generated in cell culture systems of the invention and 6-well plates, particularly average iDC yield for each experiment at 200k-600k MOs/$cm^2$ seeding density. Data presented as average±standard deviation of the indicated experiments. Data is tabulated in Tables 1-3.

FIGS. 24 and 25 show the iDC yield for each experiment and averaged data. Cell culture systems of the invention showed a slightly positive correlation between MO seeding density and iDC yield when the data is averaged between the three experiments; however, there isn't a clear trend within each individual experiment. At 600k MO seeding density, average iDC yield was similar for both cell culture systems of the invention and 6-well plates. The 6-well plates had a relatively constant iDC yield as MO seeding density increased in experiments N1 and N3; however, iDC yield decreased precipitously with MO seeding density for experiment N2.

Well plate N2 exhibited a trend inconsistent with data generated in this study and other experiments conducted in our lab. The experimental procedure was exactly the same for this well plate and we do not know of a specific issue causing this outlying trend. Viability for experiment N2 was lower than expected which is likely related to the inconsistent iDC yields in this experiment. Interestingly, phenotype was normal for these well plate generated iDCs. Average iDC data was plotted with and without 6-well plate N2 data.

Cell culture systems of the invention and 6-well plates have similar iDC yield at the highest seeding density and diverge as seeding density decreases. This indicates that MO seeding density influences the ability of MOs to differentiate into iDCs and cell culture systems of the invention iDC yield is greatest at higher seeding densities where yield is similar to the 6-well plates. Further increasing MO seeding density beyond 600k may improve iDC yield in cell culture systems of the invention, although this needs to be experimentally determined as increasing the number of MOs beyond a critical upper limit may negatively affect differentiation and phenotype of generated cells. Similar iDC yields at 600k MO seeding density between cell culture systems of the invention and well plates indicate that cell culture systems of the invention generates phenotypically similar iDCs at similar yields as well plates. Furthermore, more MOs can be seeded into a single cartridge of the present invention, allowing for greater numbers of iDCs to be harvested from a single cartridge of the present invention compared to using multiple wells/well plates. This ultimately reduces user time and minimizes potential error and contamination.

TABLE 1

Differentiation data for cell culture systems of the invention and 6-well plates

| | Seeding Density (MOs/cm$^2$) | MOs-per-cytokine activity ratio | | MOs Seeded (×10$^6$) | Cells Harvested (×10$^6$) | Viable CD45$^+$ Cells | iDCs CD209$^+$ CD141$^-$ | Viable iDCs Harvested (×10$^6$) | iDC Yield |
|---|---|---|---|---|---|---|---|---|---|
| Cell culture systems of present invention | 200 k | 1,786 | N1 | 7.94 | 2.03 | 91.0% | 79.4% | 1.47 | 18.5% |
| | | | N2 | 7.94 | 2.38 | 71.2% | 95.5% | 1.62 | 20.4% |
| | | | N3 | 7.94 | 2.73 | 93.5% | 81.5% | 2.08 | 26.2% |
| | 400 k | 3,573 | N1 | 15.88 | 6.50 | 93.9% | 80.2% | 4.9 | 30.8% |
| | | | N2 | 15.88 | 5.12 | 81.2% | 96.9% | 4.03 | 25.4% |
| | | | N3 | 15.88 | 5.05 | 91.2% | 73.6% | 3.39 | 21.3% |
| | 600 k | 5,357 | N1 | 23.81 | 9.03 | 94.7% | 70.3% | 6.01 | 25.3% |
| | | | N2 | 23.81 | 10.90 | 88.3% | 91.8% | 8.84 | 37.1% |
| | | | N3 | 23.81 | 7.95 | 93.3% | 63.2% | 4.69 | 19.7% |
| 6-Well Plate | 200 k | 2,171 | N1 | 5.70 | 2.46 | 97.5% | 97.8% | 2.44 | 42.8% |
| | | | N2 | 3.80 | 3.42 | 76.4% | 95.3% | 2.49 | 65.5% |
| | | | N3 | 3.80 | 1.37 | 96.6% | 97.7% | 1.29 | 34.0% |
| | 400 k | 4,343 | N1 | 11.40 | 4.84 | 98.0% | 96.9% | 4.60 | 40.3% |
| | | | N2 | 7.60 | 5.00 | 78.3% | 95.2% | 3.73 | 49.0% |
| | | | N3 | 7.60 | 3.14 | 96.8% | 98.1% | 2.98 | 39.2% |
| | 600 k | 6,514 | N1 | 17.10 | 6.74 | 98.3% | 95.5% | 6.33 | 37.0% |
| | | | N2 | 11.40 | 2.48 | 75.4% | 94.7% | 1.77 | 15.5% |
| | | | N3 | 11.40 | 4.40 | 96.0% | 97.7% | 4.13 | 36.2% |

As shown above in Table 1, for 6-well plates, N1 used 3 wells and N2-N3 used 2 wells. Phenotype data is shown in FIG. 20 (cell culture systems of the invention) and FIG. 21 (6-well plates).

Allogeneic Functional Assay

Figure 26:
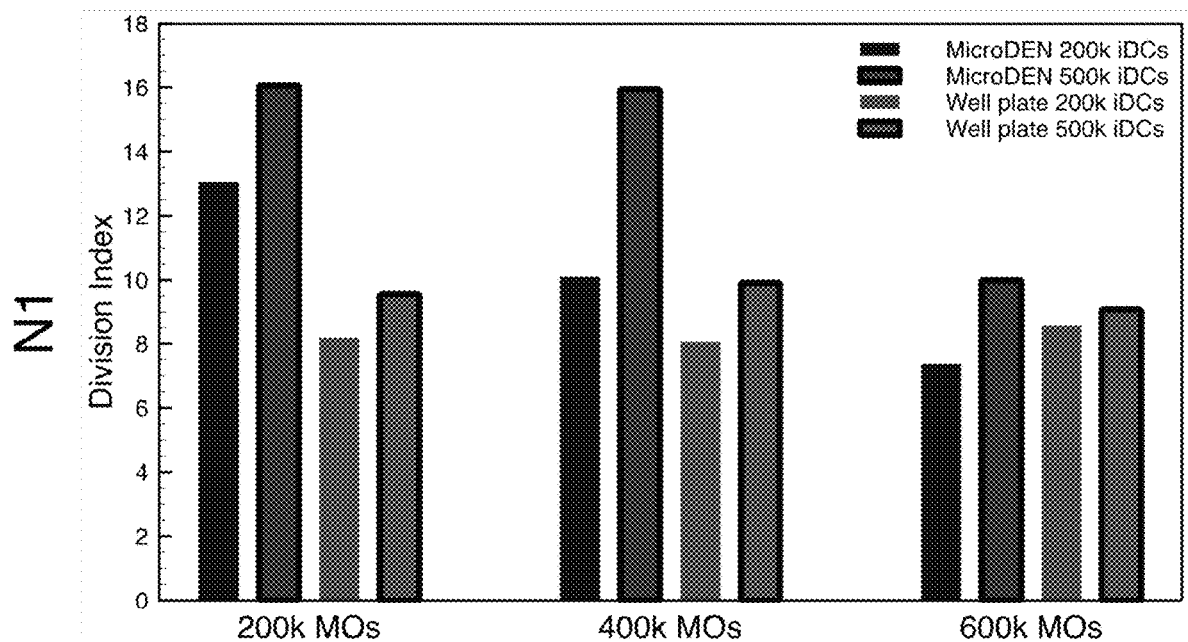
FIG. 26 shows allogeneic functional assay proliferation statistics for iDCs generated in cell culture systems of the invention or 6-well plates at 200k-600k MOs/$cm^2$ differentiation seeding density. The legend indicates iDC source (cell culture systems of the invention or 6-well plates) and the number of iDCs co-cultured with 1 million allogeneic T cells from a single donor. Tabulated data is shown in Tables 4-6.
Figure 26:
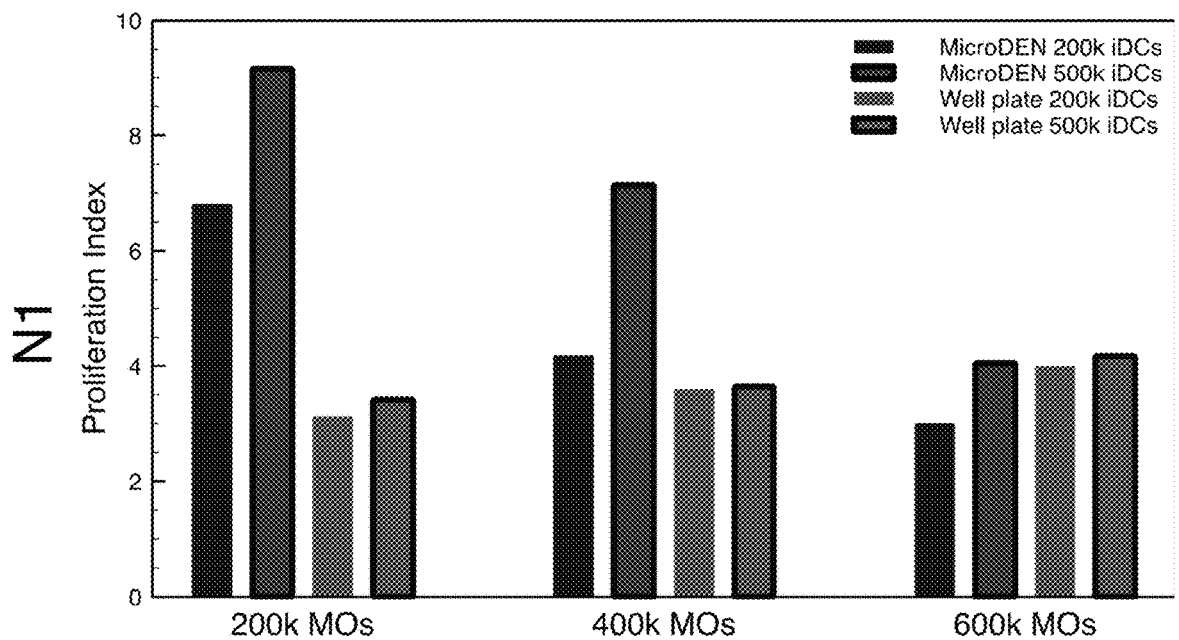
Figure 26:
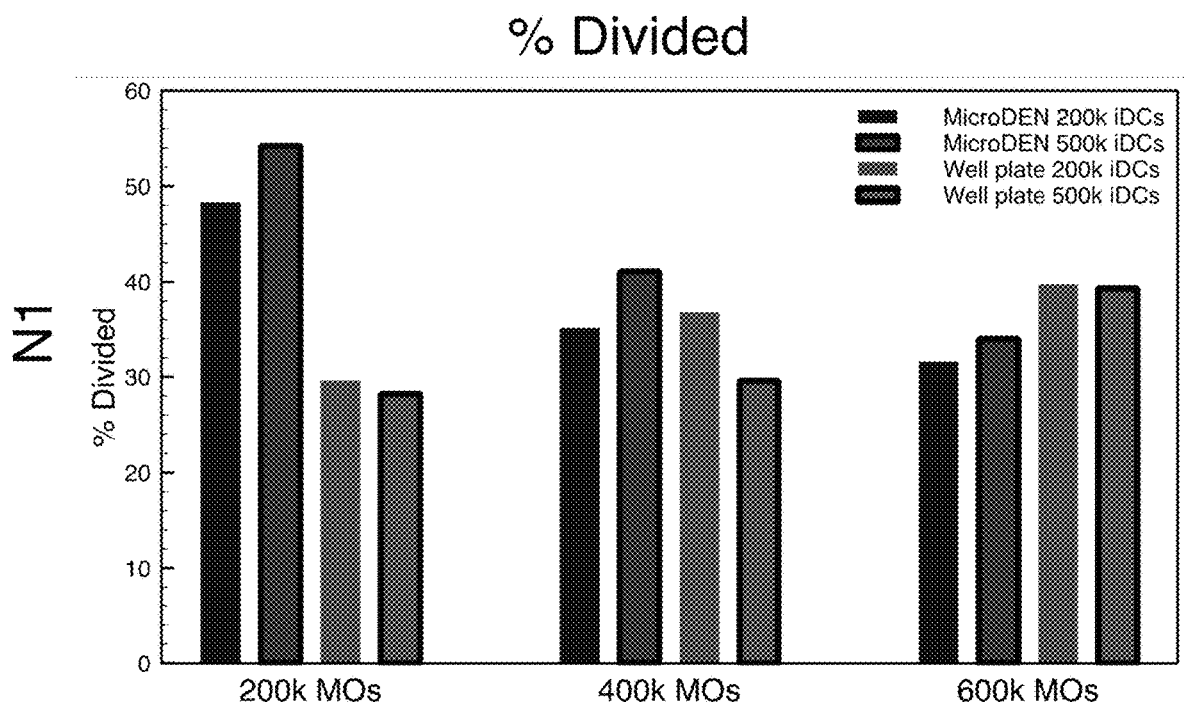
Figure 26:
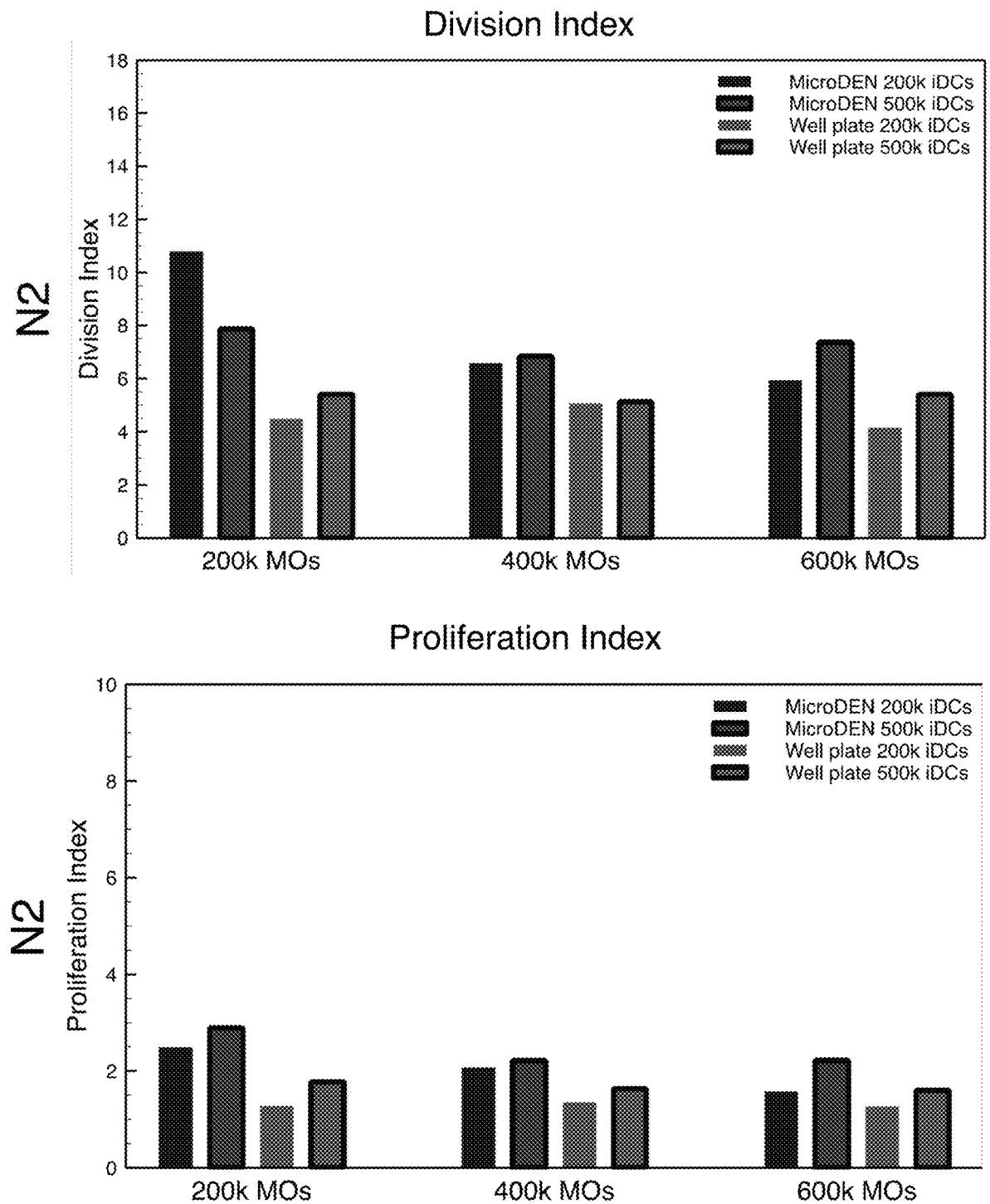
Figure 26:
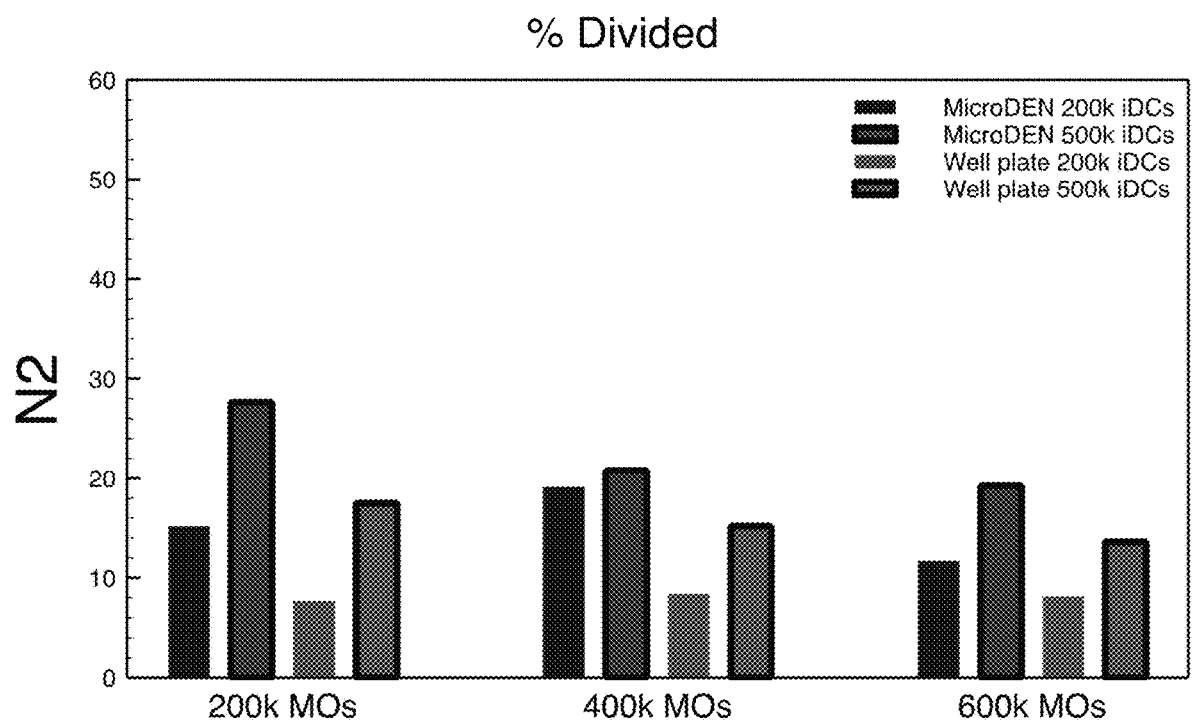
Figure 26:
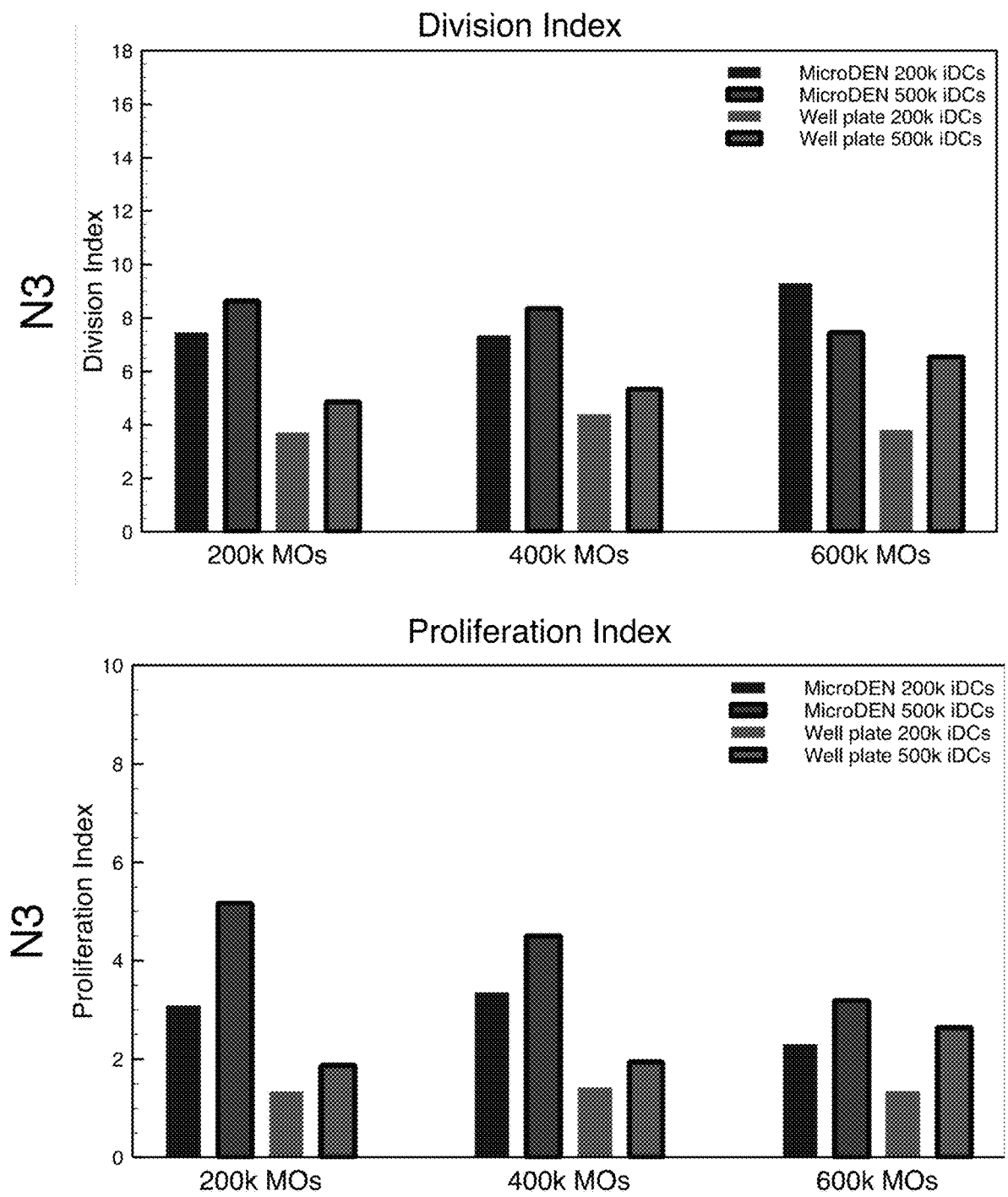
Figure 26:
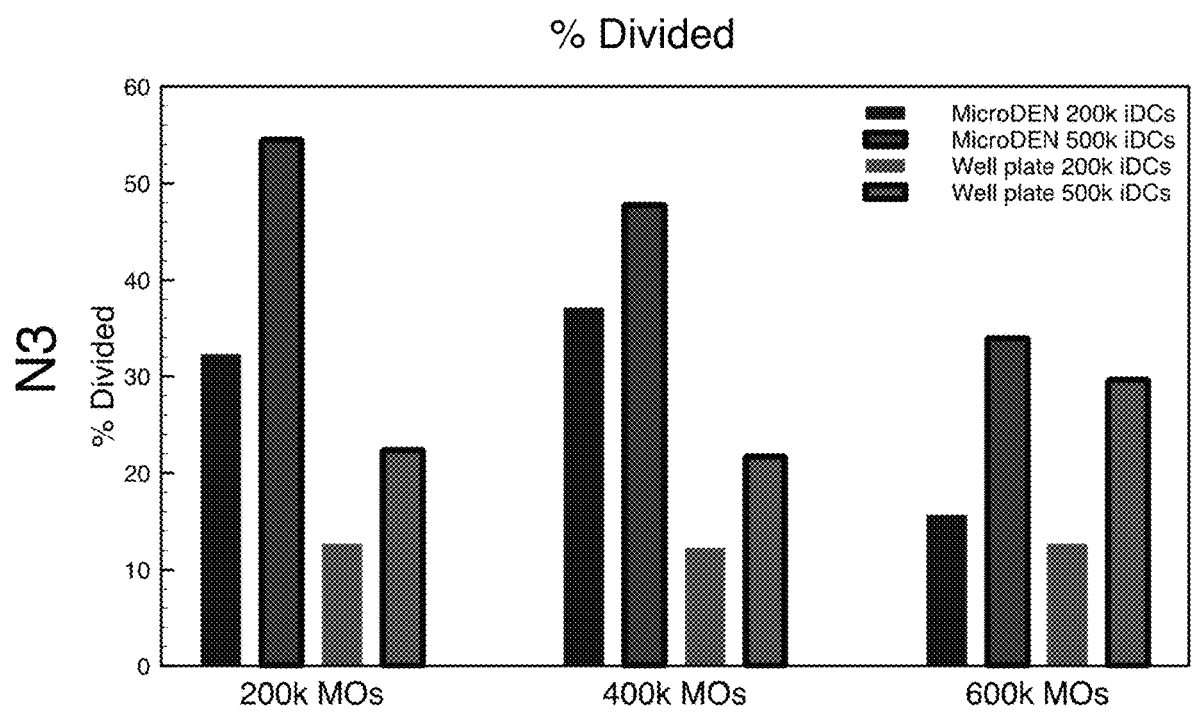
Figure 27:
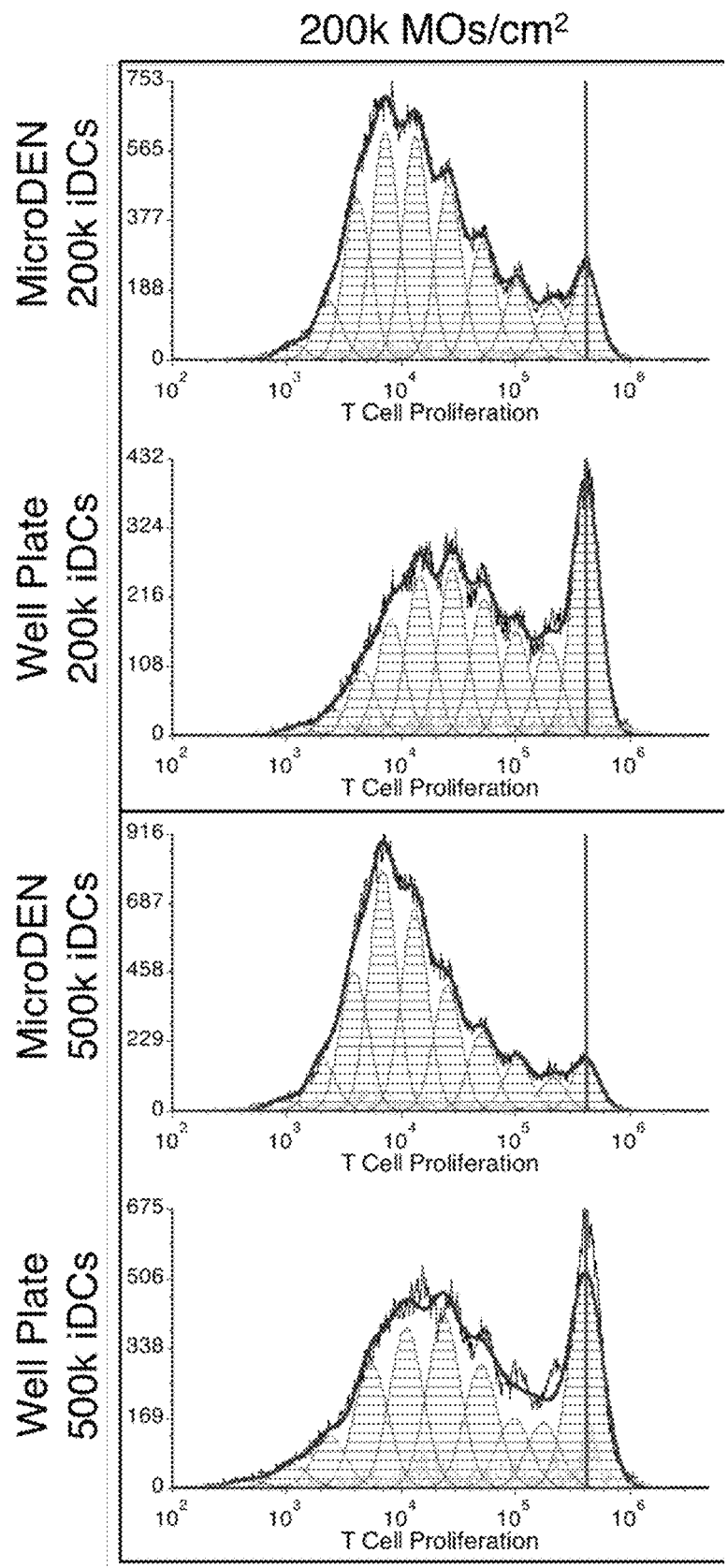
FIG. 27 shows allogeneic functional assay proliferation histograms for experiment N1. Columns indicate MO seeding density for iDC generation in cell culture systems of the invention or 6-well plates. Rows indicate iDC source (cell culture systems of the invention or 6-well plate) and the number of iDCs co-cultured with 1 million allogeneic T cells for 5 days. The green vertical line indicates the stained, unstimulated control peak location which is also the location of undivided cells. The thicker curve indicates the overall fit and the thinner curves indicate individual T cell generations. Histograms for experiments N2-N3 are shown in FIGS. 32 and 33. Unstimulated T cell control is shown in FIGS. 34-36.
Figure 27:
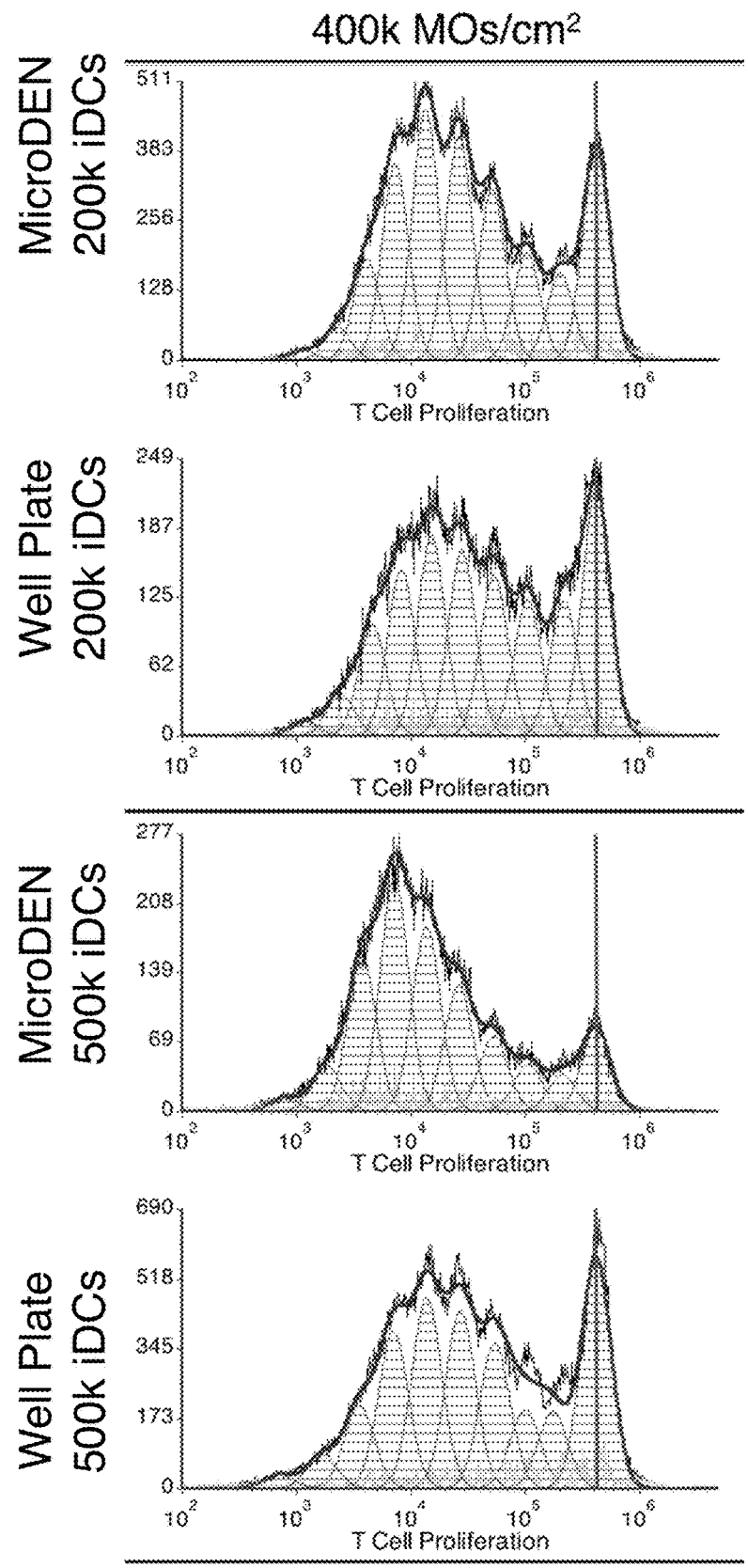
Figure 27:
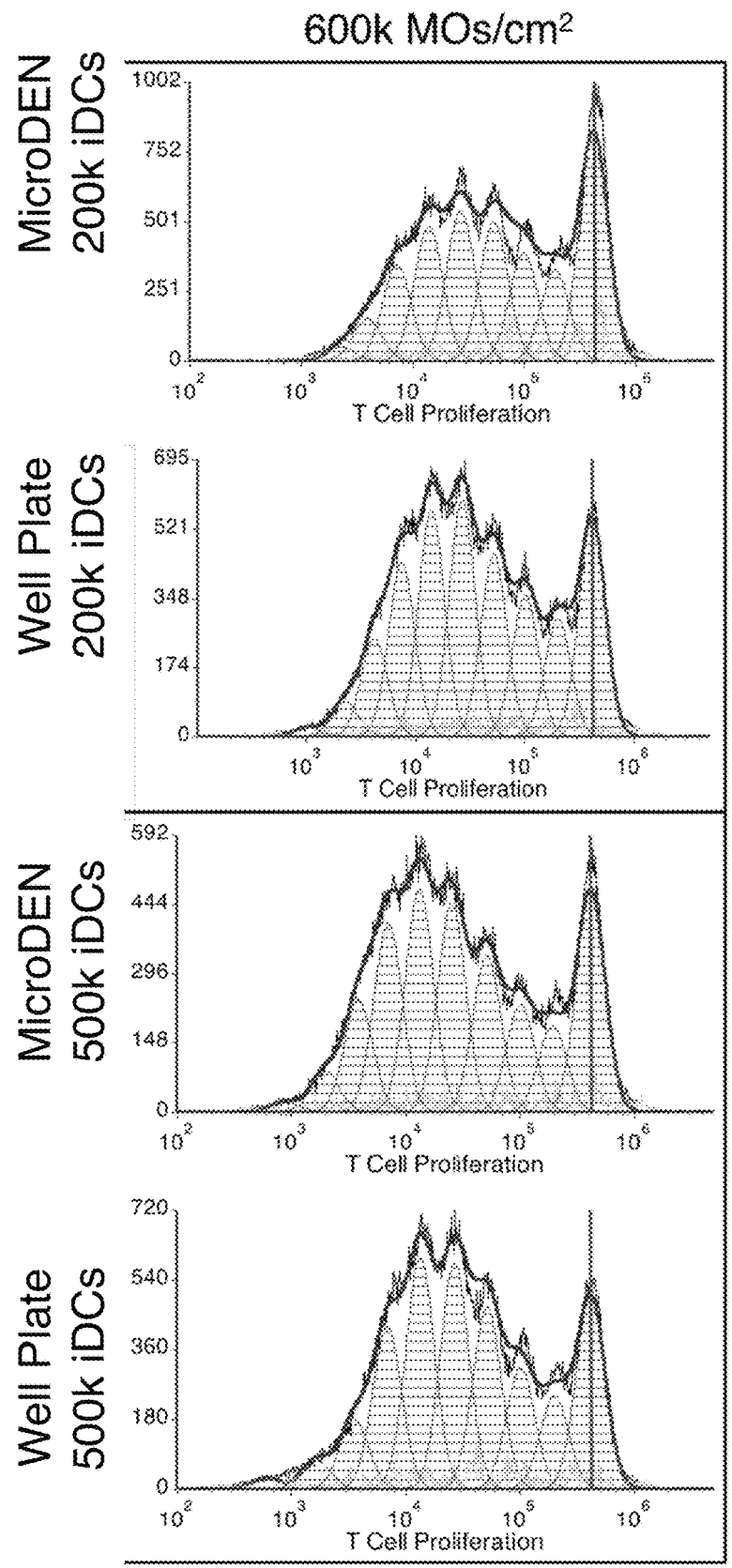
Figure 32:
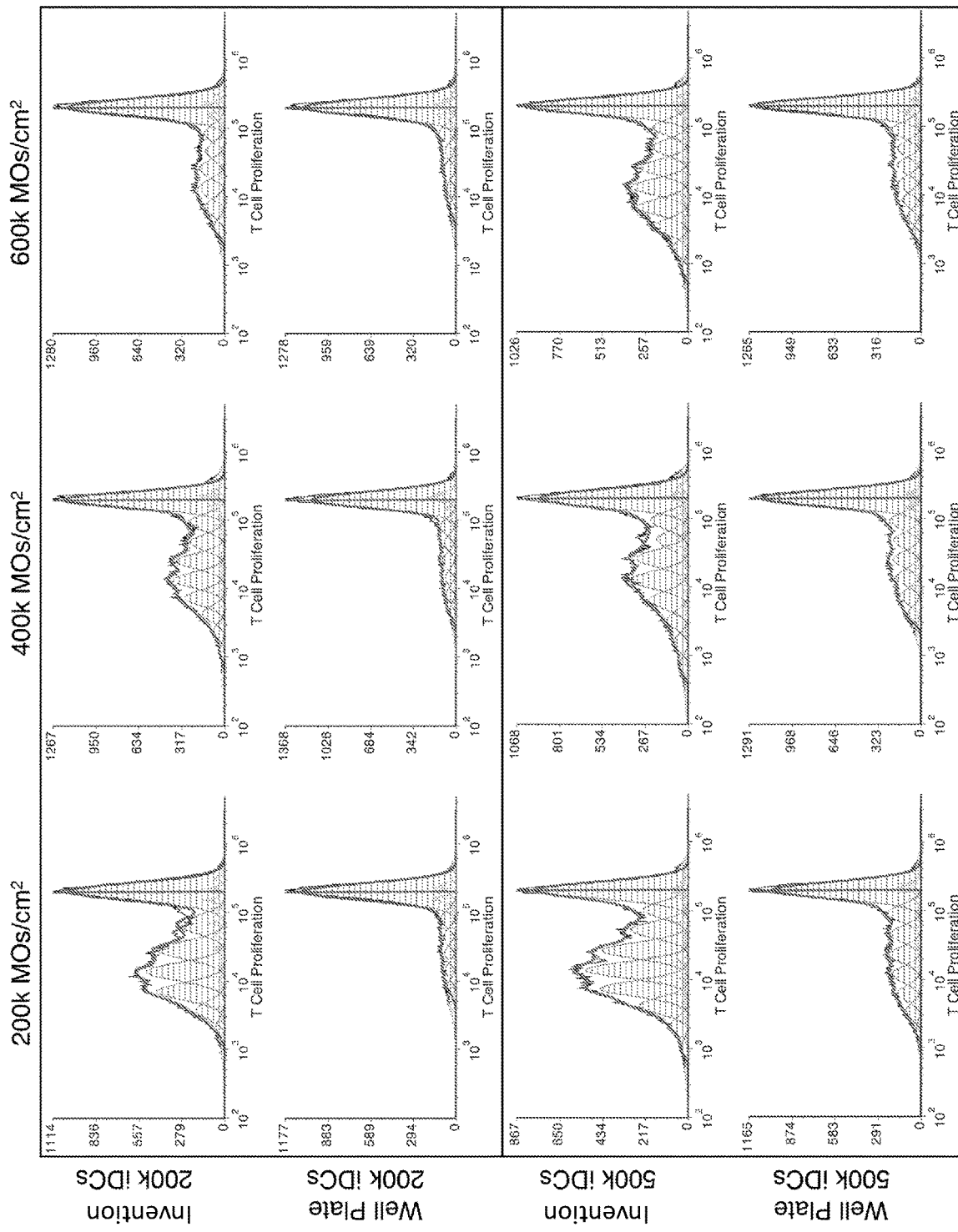
FIG. 32 shows Experiment N2: Allogeneic functional assay histograms. T cell control is shown in FIGS. 34-36.
Figure 33:
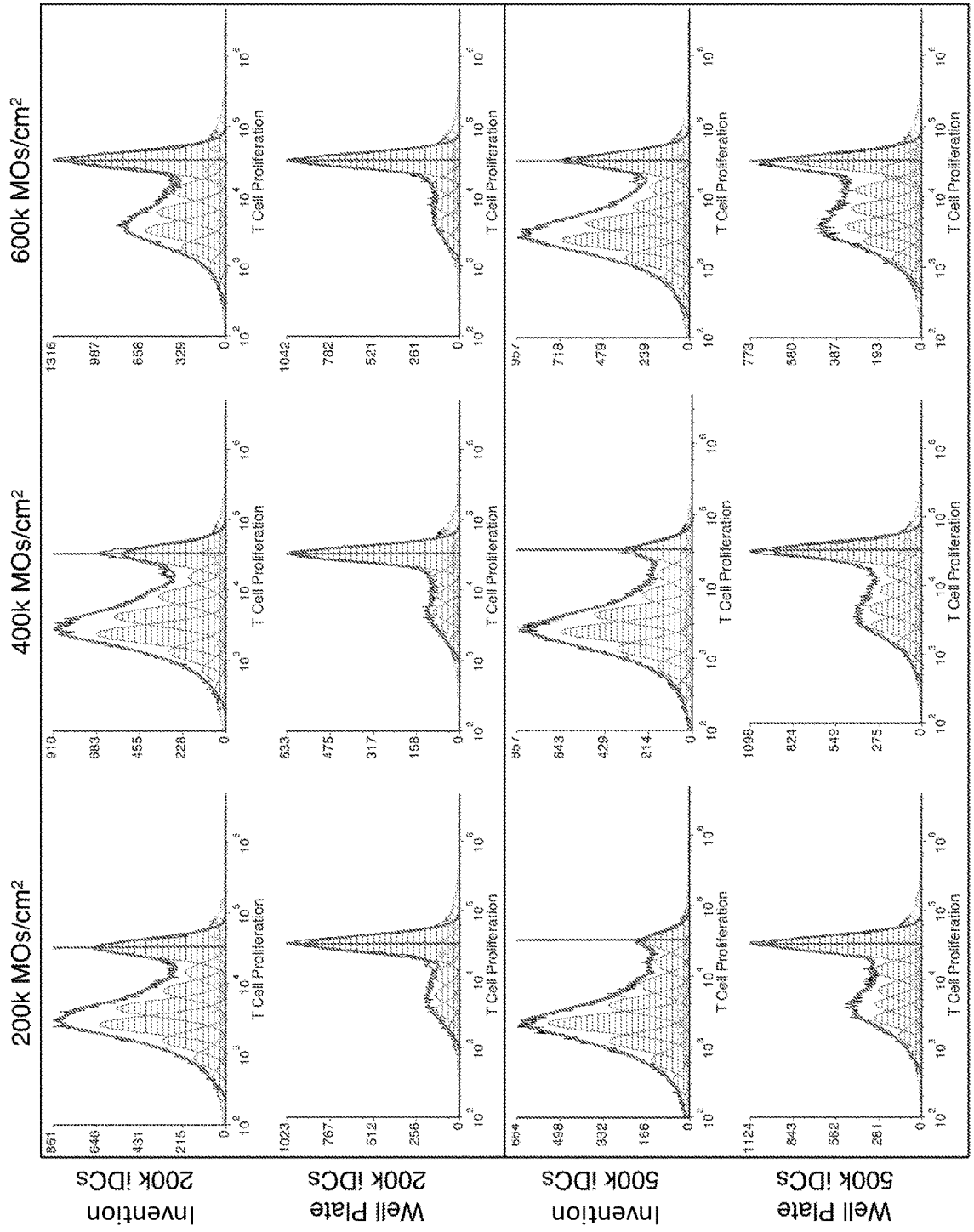
FIG. 33 shows Experiment N3: Allogeneic functional assay histograms. T cell control is shown in FIGS. 34-36.

The ability of generated iDCs to induce T cell proliferation was examined via allogeneic functional assays. 1 million T cells derived from a single donor were co-cultured with 200k or 500k iDCs derived from a different MO donor for each experiment (N1, N2, N3). FIG. 26 shows proliferation statistics and FIG. 27 shows T cell proliferation histograms for experiment N[1]. Histograms for experiments N2 and N3 are shown in FIGS. 32 and 33. Proliferation statistics include division index (average number of cells resulting from each dividing cell), proliferation index (average number of cells relative to the number of initial, generation 0 cells), and percent divided (the percentage of cells in the initial population that underwent division). By performing this allogeneic functional assay, we sought to answer two questions: (i) does MO seeding density affect the ability of iDCs to induce T cell proliferation? and (ii) how do cell culture systems of the invention iDCs compare to 6-well plate iDCs at a given MO seeding density?

(i) There is a clear correlation between MO seeding density used for cell culture systems of the invention-generated iDCs and the ability of those iDCs to induce T cell proliferation; whereas, MO seeding density appears to have very little effect on functionality of well plate generated iDCs. Cell culture systems of the invention iDCs generated from low MO seeding densities (200k and 400k) exhibit greater ability to induce T cell proliferation than iDCs generated from 600k MO seeding density. T cell proliferation decreases as MO seeding density used to generate iDCs increases for cell culture systems of the invention iDCs and cell culture systems of the invention iDCs have similar functionality to well plate iDCs when generated at 600k MO seeding density.

(ii) IDCs generated from low MO seeding densities (200k and 400k) in cell culture systems of the invention are markedly better at inducing T cell proliferation compared to 6-well plate iDCs. This effect is reduced at high MO seeding density (600k) where cell culture systems of the invention iDCs perform marginally better than well plate generated iDCs. These results were consistent for all three experiments.

Expectedly, T cell proliferation was greater when 500k iDCs were seeded into the T cell assay compared to 200k iDCs. The data from this assay shows that cell culture systems of the invention generated iDCs are capable of inducing T cell proliferation without addition of IL-2, a common cytokine used for T cell expansion. Cell culture systems of the invention-generated iDCs also induce greater T cell proliferation compared to 6-well plate generated iDCs, regardless of MO seeding density. It is important to note that the allogeneic T cell assay is a straightforward benchmark used for ascertaining DC functionality and the results observed within this study may not extend to specialized syngeneic and other mixed lymphocyte reaction (MLR) functional assays.

Relationship Between iDC Phenotype and T Cell Proliferation

Figure 28:
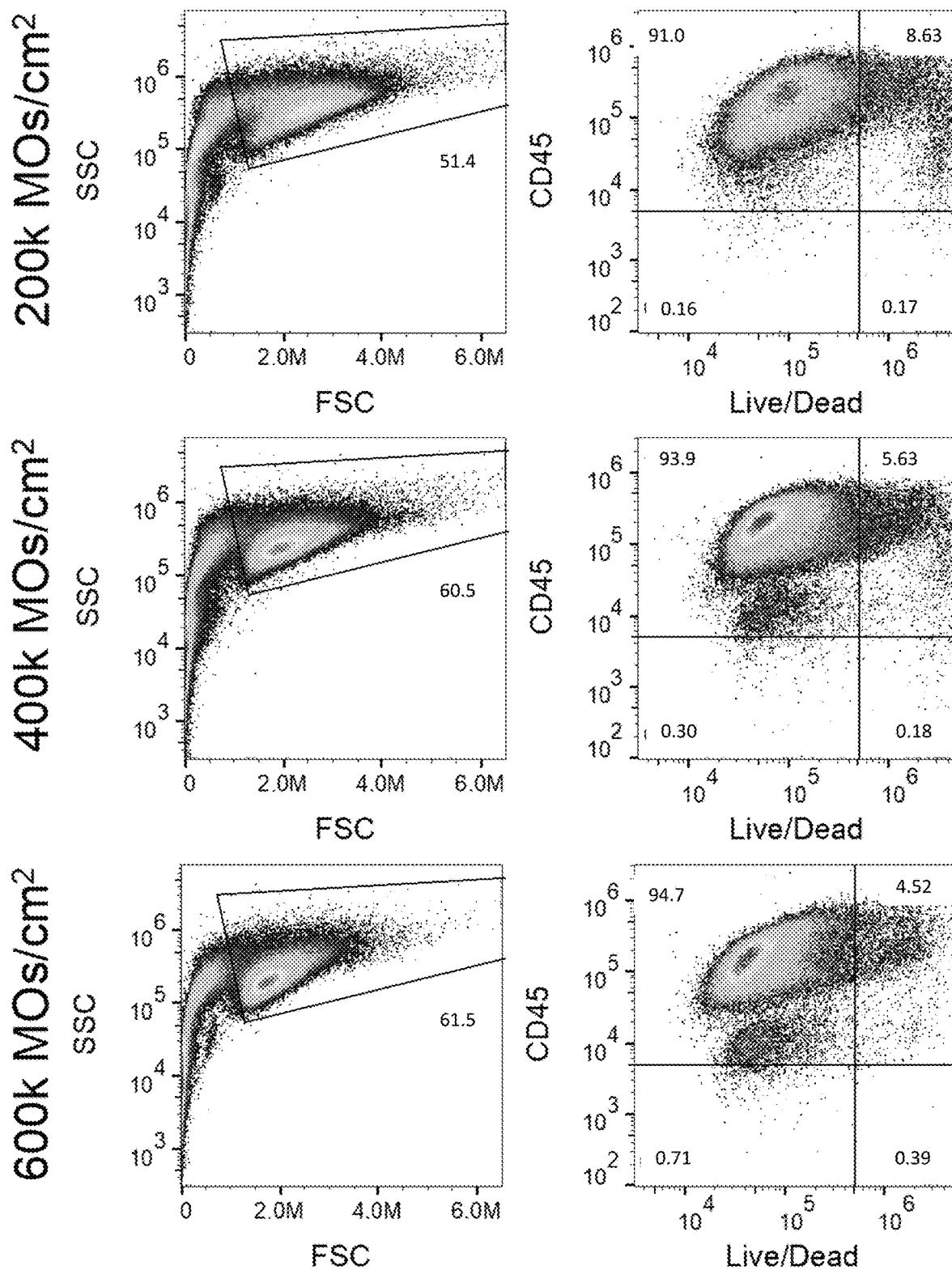
FIG. 28 shows cell culture systems of the invention N1 iDC phenotype.
Figure 28:
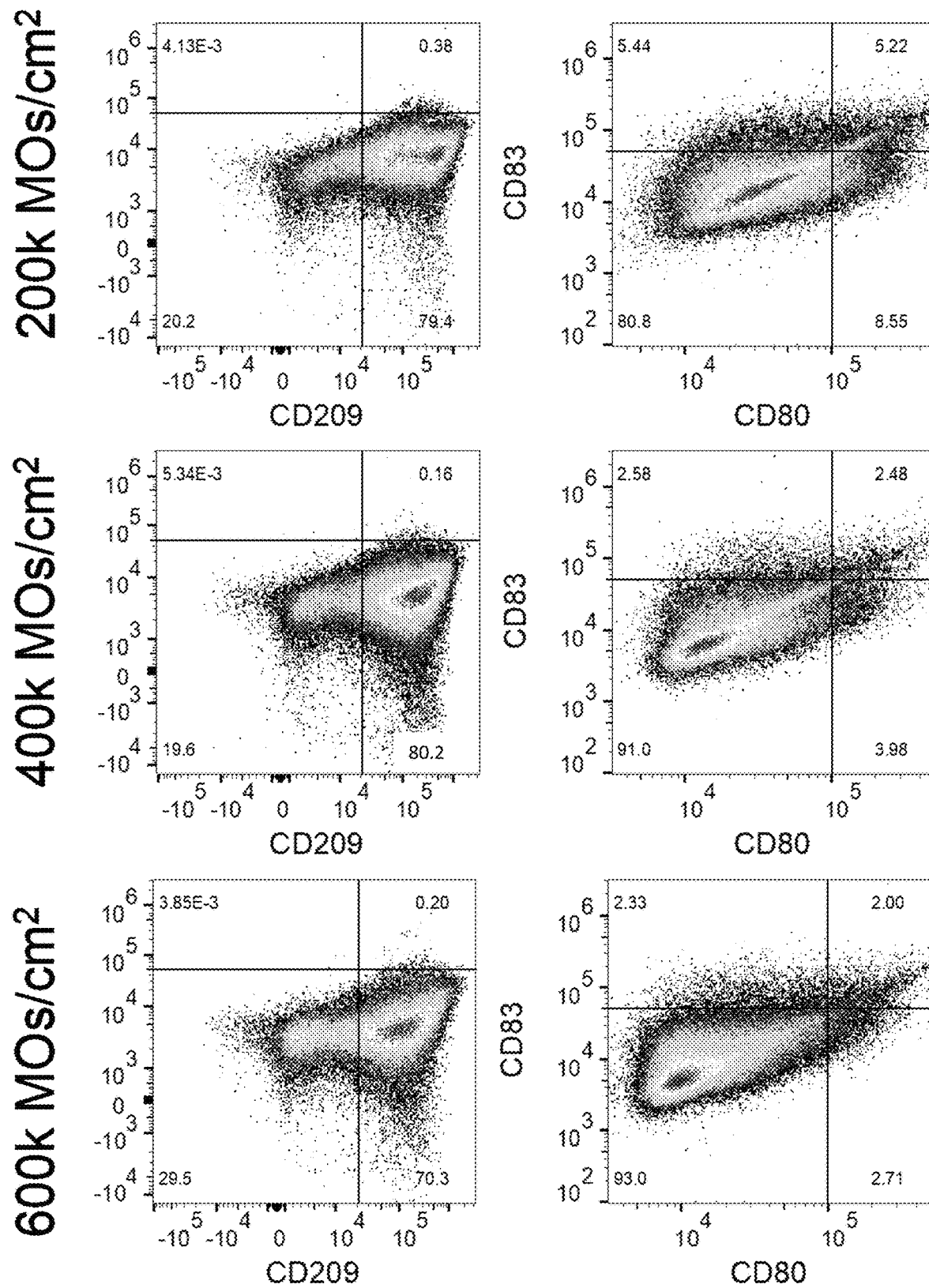
Figure 28:
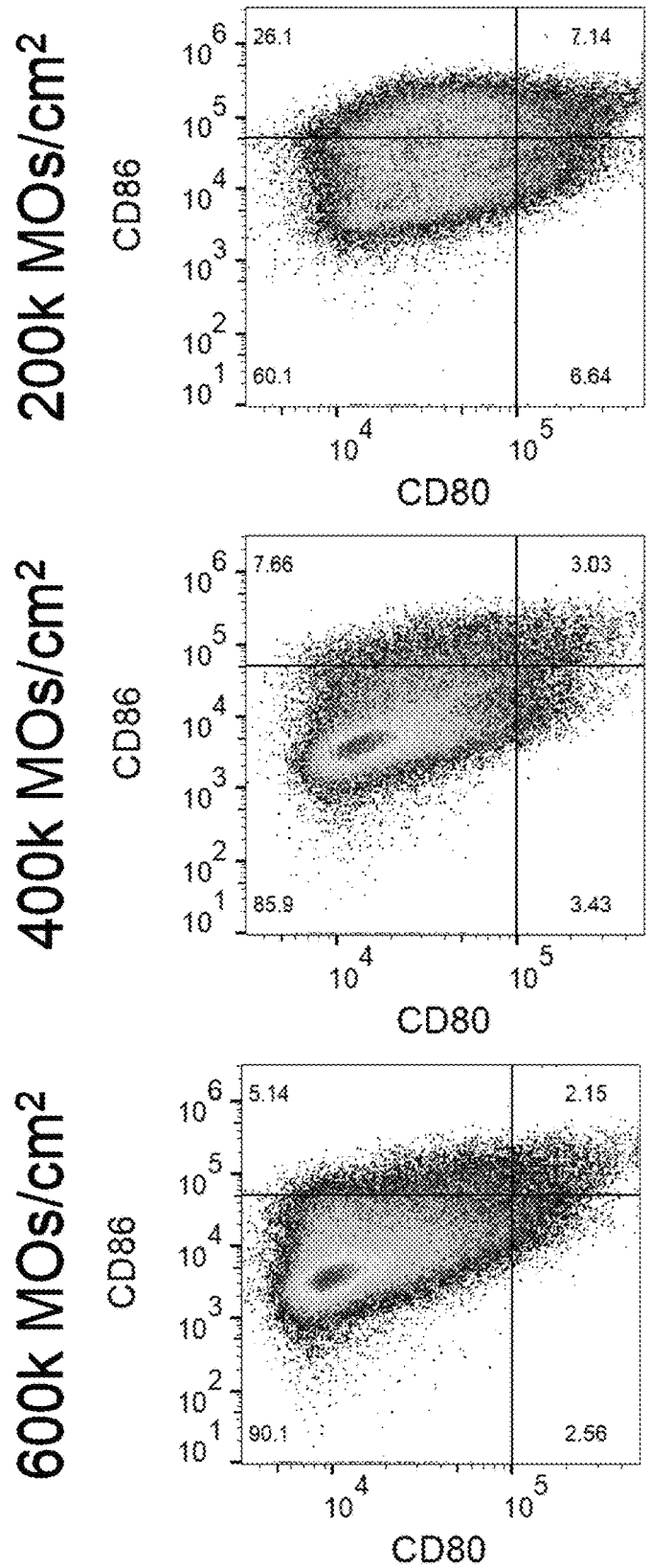
Figure 29:
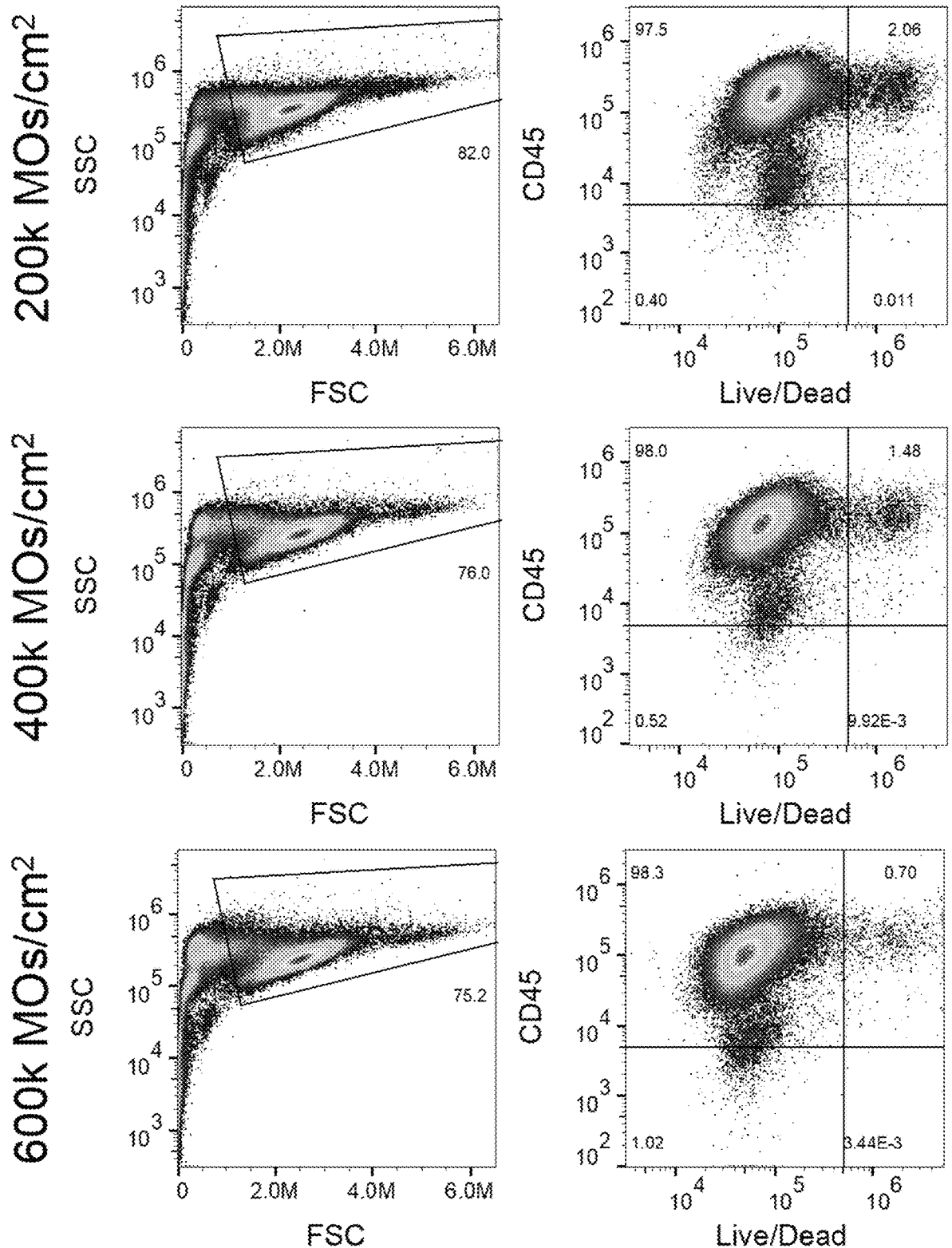
FIG. 29 shows 6-well plate N1 iDC phenotype.
Figure 29:
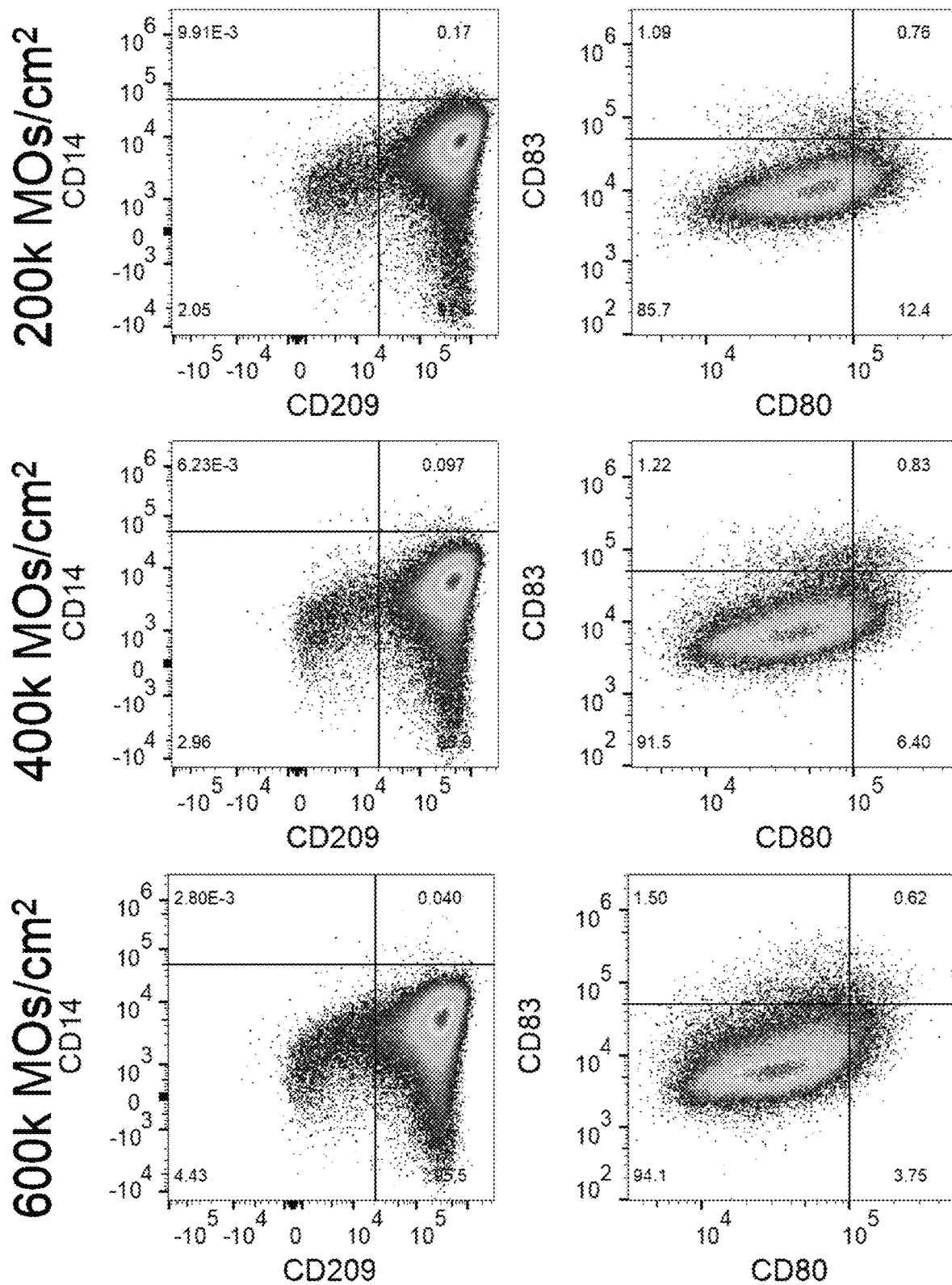
Figure 29:
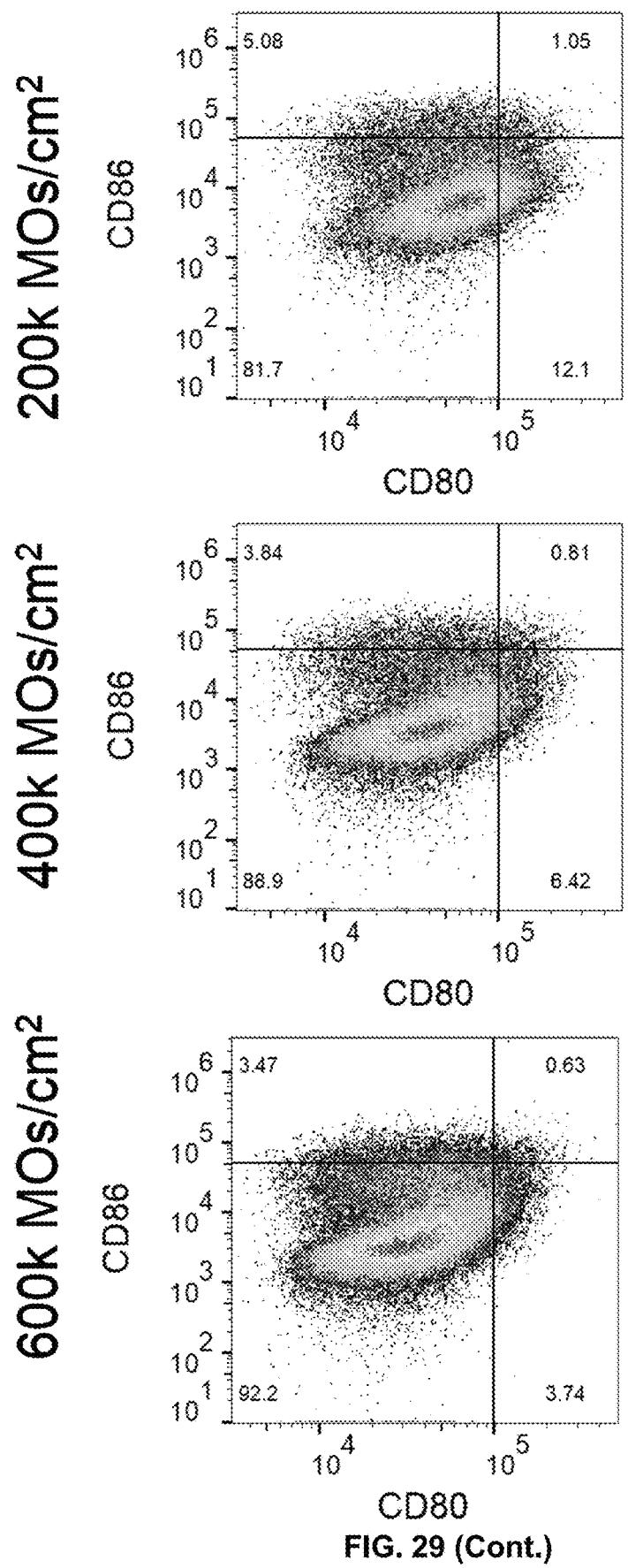
Figure 30:
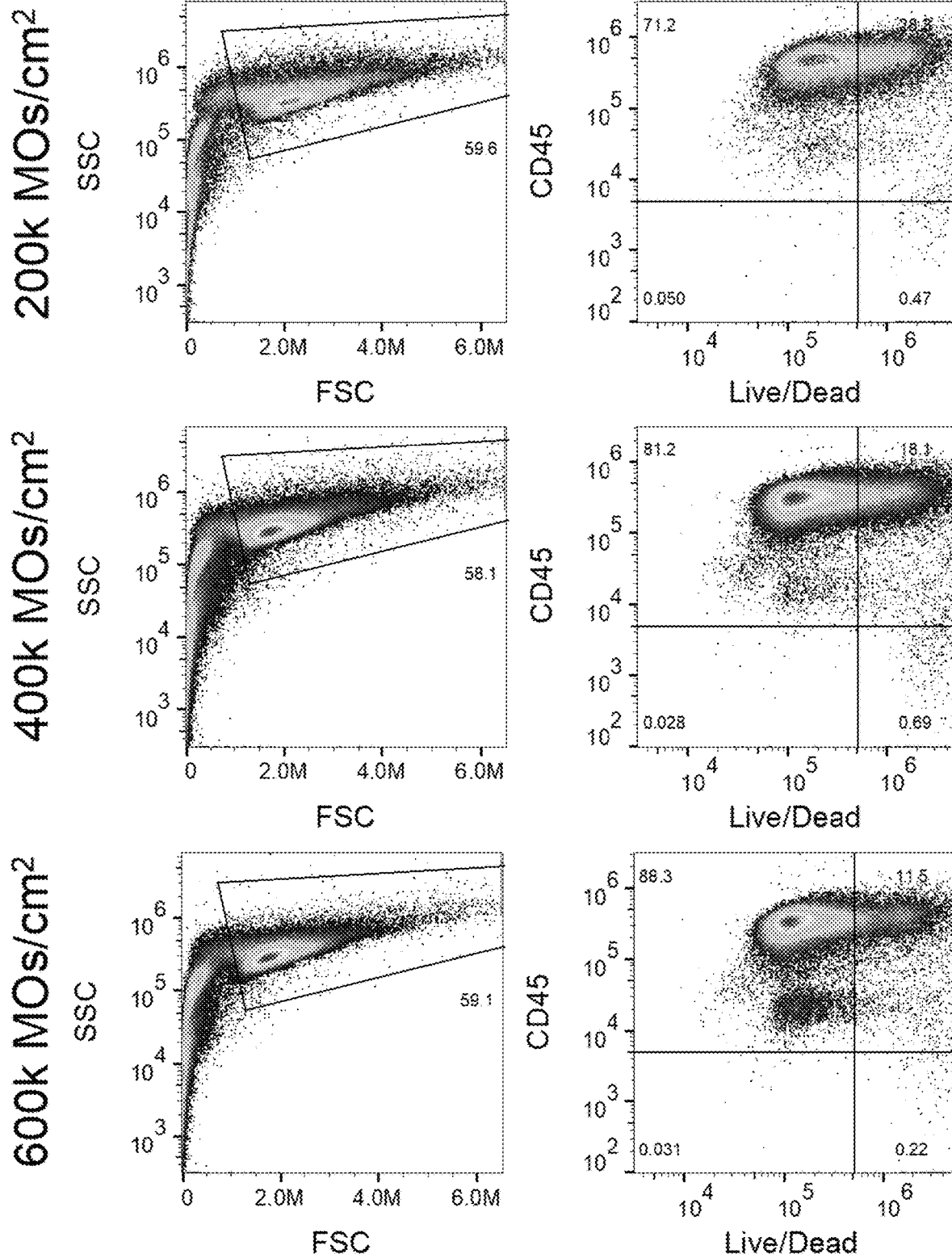
FIG. 30 shows cell culture systems of the invention N2 iDC phenotype.
Figure 30:
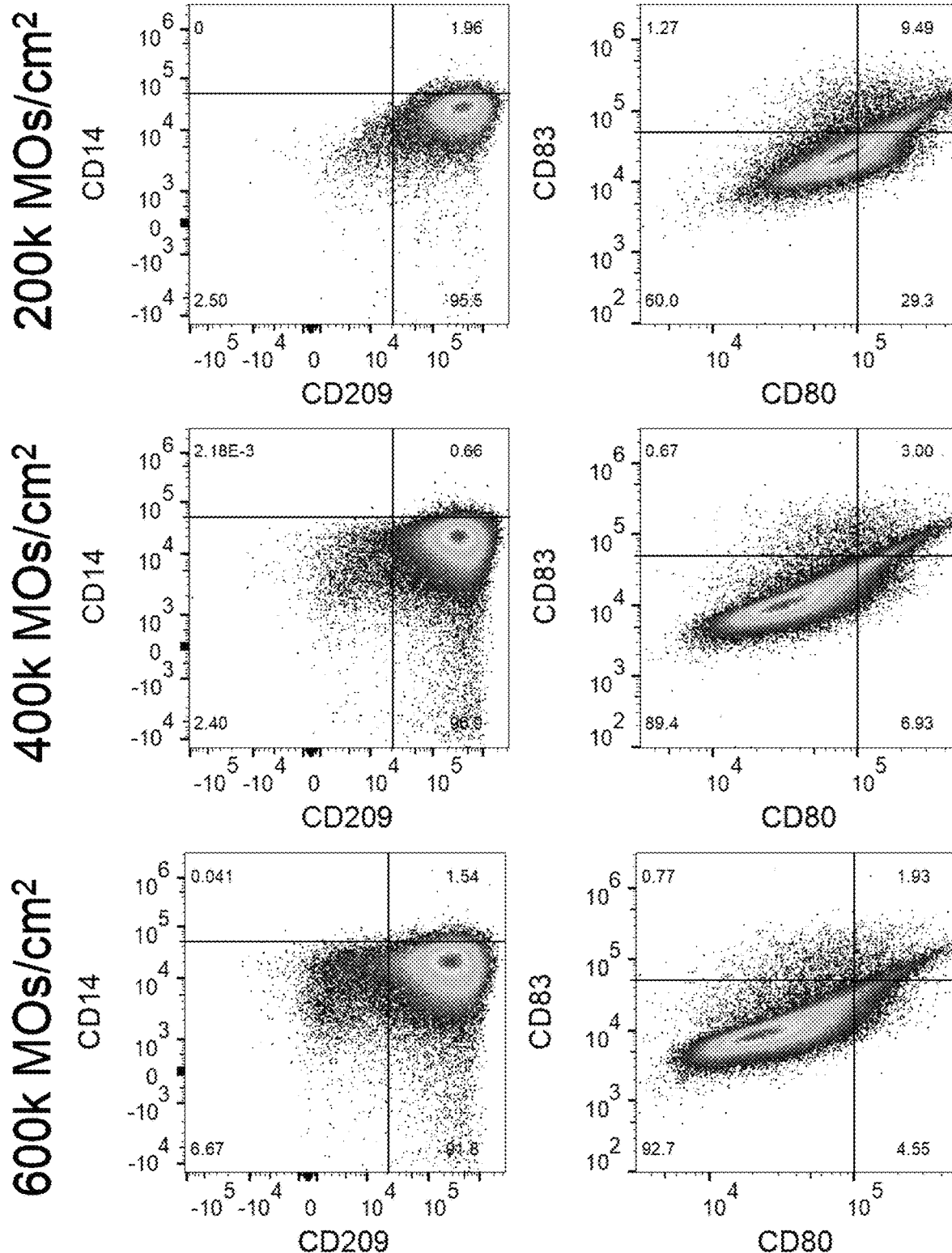
Figure 30:
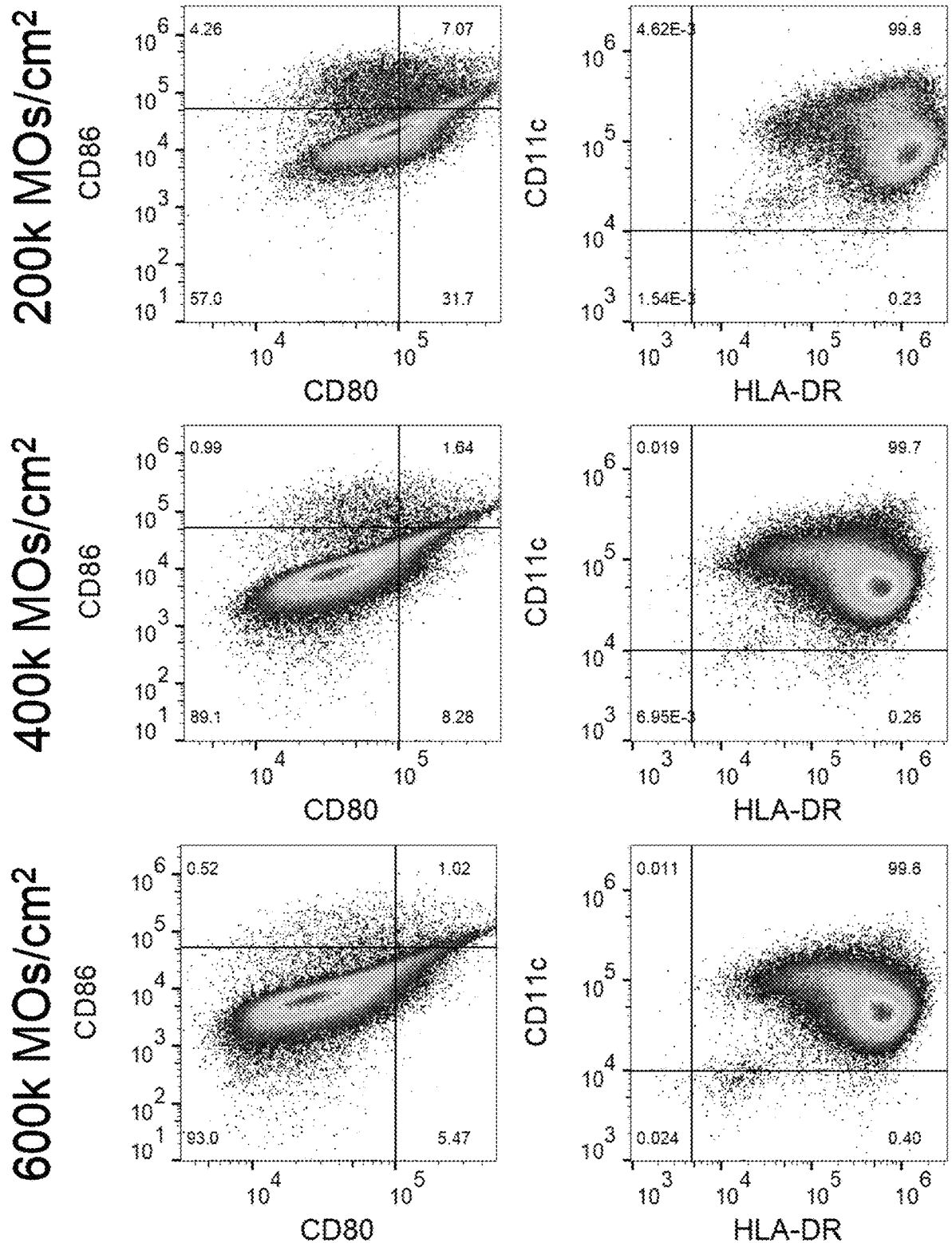
Figure 31:
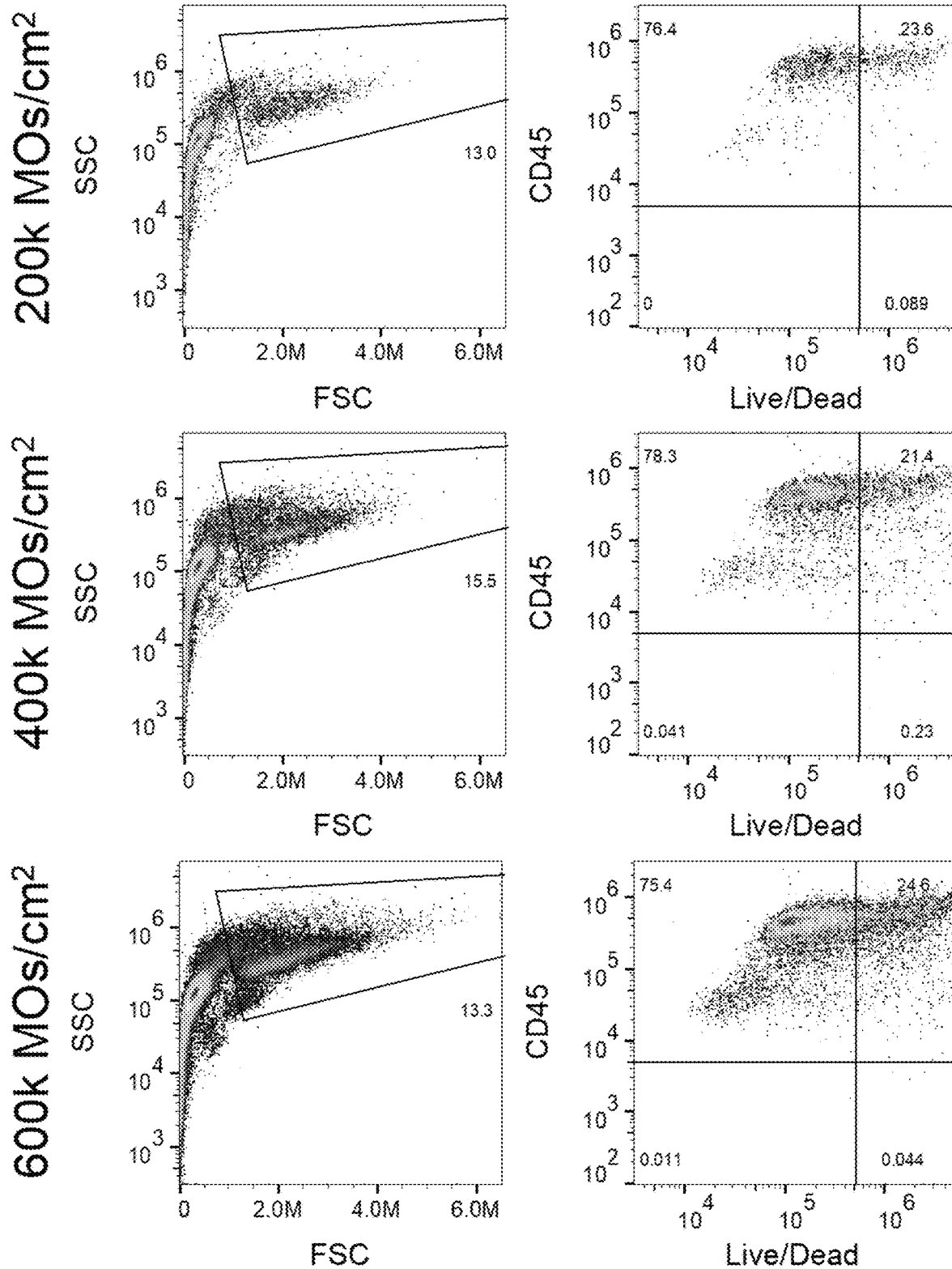
FIG. 31 shows 6-well plate N2 iDC phenotype.
Figure 31:
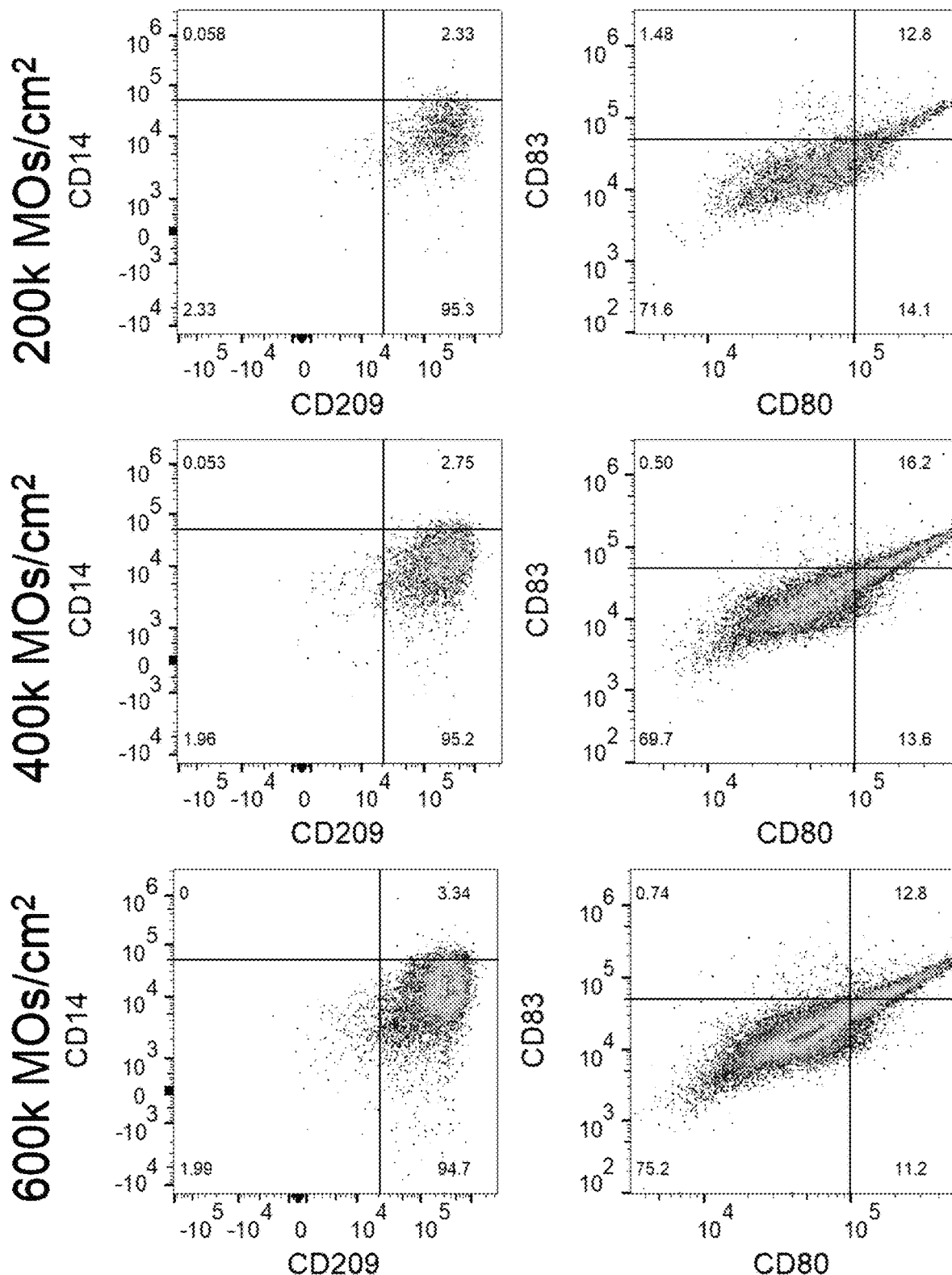
Figure 31:
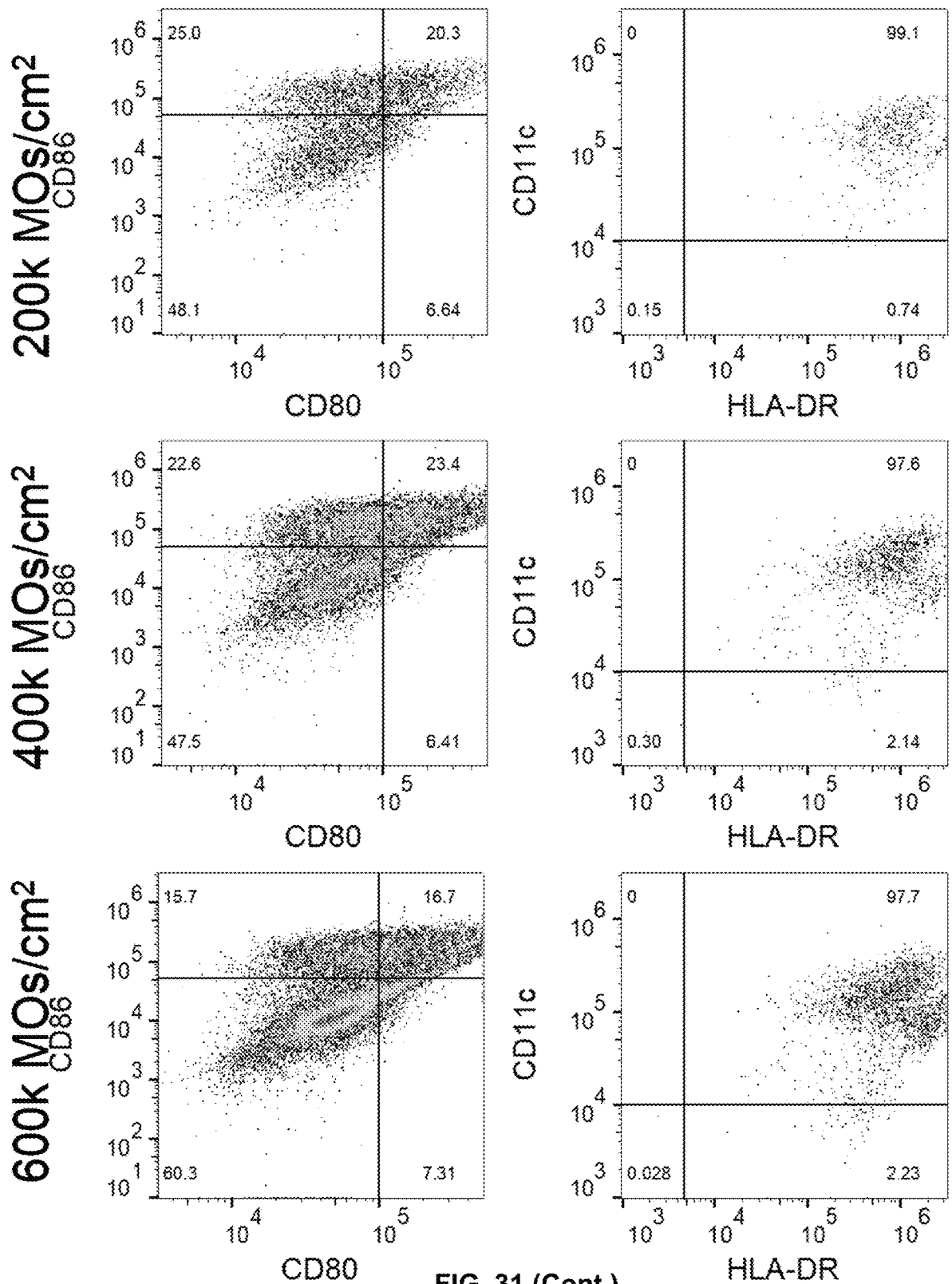

To ascertain why cell culture systems of the invention iDCs have greater ability to induce T cell proliferation, phenotype data was compared, shown in FIGS. 20, 28, and 30 (cell culture systems of the invention) and FIGS. 21, 29, and 31 (6-well plate). Two important trends were observed: (1) phenotype differences of cell culture systems of the invention iDCs strongly correlate to T cell proliferation and (2) there is a very weak to nonexistent correlation between phenotype of 6-well plate iDCs and T cell proliferation.

(1) Phenotype of cell culture systems of the invention iDCs is dependent on MO seeding density. Cell culture systems of the invention generated substantially more CD80$^+$/83$^+$/86$^+$ at lower MO seeding densities compared to 600k MO seeding density. These CD80$^+$/83$^+$/86$^+$ iDCs are more differentiated and exhibit a phenotype more similar to mature DCs (mDCs) compared to the CD80$^-$783$^-$786$^-$ iDCs. This is possibly a consequence of the lower MO-per-cytokine activity ratio at lower MO seeding densities and these iDCs consequentially have greater ability to induce T cell proliferation. See Table 1 for values of MOs per cytokine activity. These results are consistent with previous studies implicating CD80$^+$/83$^+$/86$^+$ iDCs with greater functionality, even when the majority of cells in a sample are negative for these markers. Thus, the presence of CD80$^+$/83$^+$/86$^+$ iDCs generated in cell culture systems of the invention indicate greater functional ability.

(2) Phenotype of 6-well plate iDCs is not dependent on MO seeding density. The well plates generated primarily CD83$^-$786$^-$ iDCs with a sizable CD80$^+$ population at all three MO seeding densities. Furthermore, there were no discernable phenotype differences in well plate iDCs generated from different MO seeding densities. This suggests that MO-per-cytokine activity ratio does not affect well plate iDC generation within the scope of this study. This is possibly because the MO-per-cytokine activity ratio is sufficient for any reasonable MO seeding density in static culture. Since the cytokines available to the MOs was sufficient for differentiation and no phenotypic differences were observed, T cell proliferation induced by well plate iDCs was similar at all conditions studied.

within the wells that is different from cell culture systems of the invention. A detailed analysis of cytokine kinetics (e.g., consumption during MO differentiation and cytokine degradation) along with kinetics of lactic acid and $CO_2$ production is required to better understand the specific causes of these results.

Another factor that could explain the functional difference between cell culture systems of the invention and well plate iDCs is the exact nature of the polystyrene surface in contact with the cells. Cell culture systems of the invention used polystyrene that was $O_2$ plasma treated; whereas, the 6-well plates were tissue culture treated. The type of surface treatment and the exact nature of the polystyrene may affect iDC generation. Despite these differences, cell culture systems of the invention generated iDCs that are phenotypically similar to standard well plate culture and are functionally competent in proliferating allogeneic T cells.

iDC Yield

TABLE 2

| | | | iDCs harvested per cm² for Experiments N1-N3 | | |
|---|---|---|---|---|---|
| | MO Seeding Density | | iDCs Harvested | Average iDCs Harvested per cm² | |
| | MOs/cm² | Experiment | per cm² | All Data | N1 & N3, omitting N2 |
| Cell culture systems of the invention | 200k | N1 | 37,028 | 43,409 ± 6,537 | — |
| | | N2 | 40,806 | | |
| | | N3 | 52,393 | | |
| | 400k | N1 | 123,426 | 103,442 ± 15,588 | — |
| | | N2 | 101,511 | | |
| | | N3 | 85,390 | | |
| | 600k | N1 | 151,385 | 164,064 ± 43,607 | — |
| | | N2 | 222,670 | | |
| | | N3 | 118,136 | | |
| Well Plate | 200k | N1 | 85,614 | 94,854 ± 26,599 | 76,754 ± 8,860 |
| | | N2 | 131,053 | | |
| | | N3 | 67,895 | | |
| | 400k | N1 | 161,404 | 171,520 ± 17,632 | 159,123 ± 2,281 |
| | | N2 | 196,316 | | |
| | | N3 | 156,842 | | |
| | 600k | N1 | 222,105 | 177,544 ± 59,701 | 219,737 ± 2,368 |
| | | N2 | 93,158 | | |
| | | N3 | 217,368 | | |

T cell proliferation decreases when fewer iDCs are CD80$^+$/83$^+$/86$^+$, evidenced by cell culture systems of the invention data and lower T cell proliferation for well plate iDCs. CD80$^-$/83$^-$786$^-$ iDCs also induce T cell proliferation but to a lesser extent than if the iDCs were CD80$^+$/83$^+$/86$^+$. This indicates that CD209 itself is not sufficient for predicting ability of iDCs to induce T cell proliferation and the extent of CD80/83/86 expression is a better indicator.

Cell culture systems of the invention iDCs generated from 600k MO seeding density generally induces greater T cell proliferation compared to well plate iDCs generated under the same conditions (FIG. 26). This difference is likely a consequence of perfusion in cell culture systems of the invention since all other conditions remained equivalent. Perfusion may affect MO-to-iDC kinetics. Perfusion in cell culture systems of the invention also removes medium from the cartridge which concurrently removes toxic byproducts ($CO_2$ and lactic acid) dissolved in the medium due to cellular respiration. The continuous removal of medium may maintain a lower pH within cell culture systems of the invention compared to well plates where the toxic byproducts are not removed. Additionally, 1 mL/well of differentiation medium is added to the well plates on Day 3 to replenish cytokines. This likely has an effect on overall cytokine concentration Table 2 shows experiments N1-N3, specifically iDCs harvested per cm² for cell culture systems of the present invention (39.7 cm²) or 6-well plates (9.5 cm²/well). Average iDCs harvested per cm² with well plate N2 data omitted; average±standard deviation.

TABLE 3

| Average (± standard deviation) iDC yield for Experiments N1-N3 | | | |
|---|---|---|---|
| MO Seeding | N1, N2, N3 | | N1 & N3, |
| Density MOs/cm² | Cell culture systems of the invention | 6-Well Plate | omitting N2 |
| 200k | 21.7% ± 3.3% | 47.4% ± 13.3% | 38.4% ± 4.4% |
| 400k | 25.8% ± 3.9% | 42.8% ± 4.4% | 39.8% ± 0.6% |
| 600k | 27.4% ± 7.3% | 29.6% ± 10.0% | 36.6% ± 0.4% |

Allogeneic Functional Assay

Figure 34:
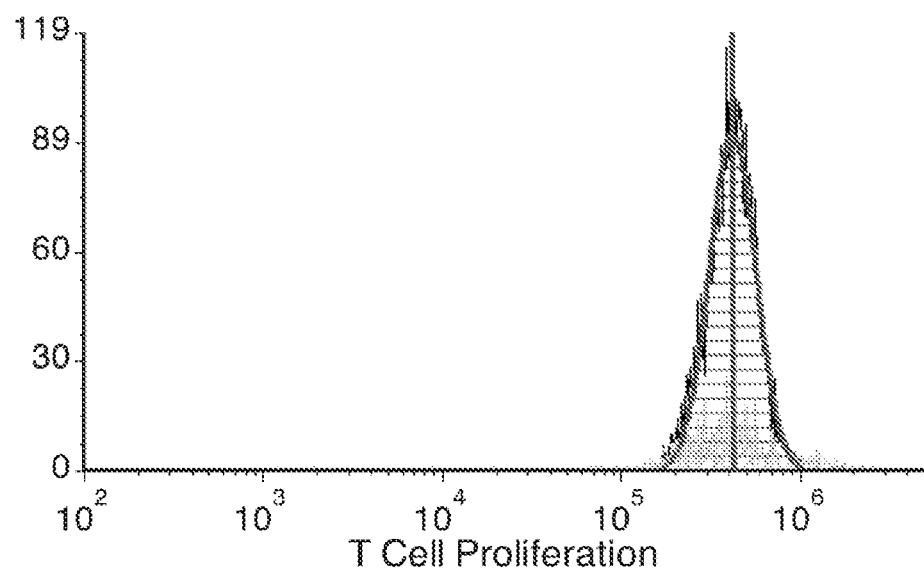
FIG. 34 shows allogeneic functional assay T cell control for N1. 1 million T cells (same donor for N1-N3) were cultured without iDCs for 5 days.
Figure 35:
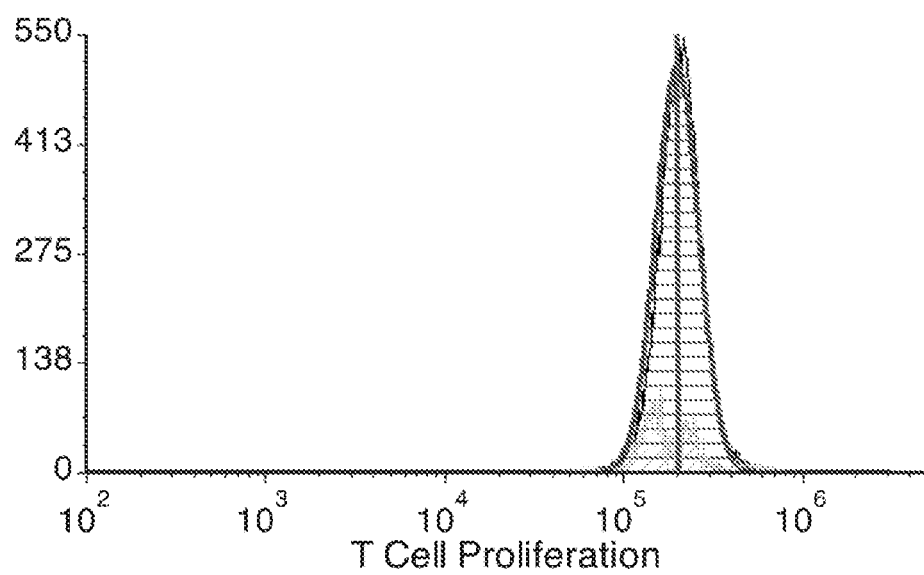
FIG. 35 shows allogeneic functional assay T cell control for N2. 1 million T cells (same donor for N1-N3) were cultured without iDCs for 5 days.
Figure 36:
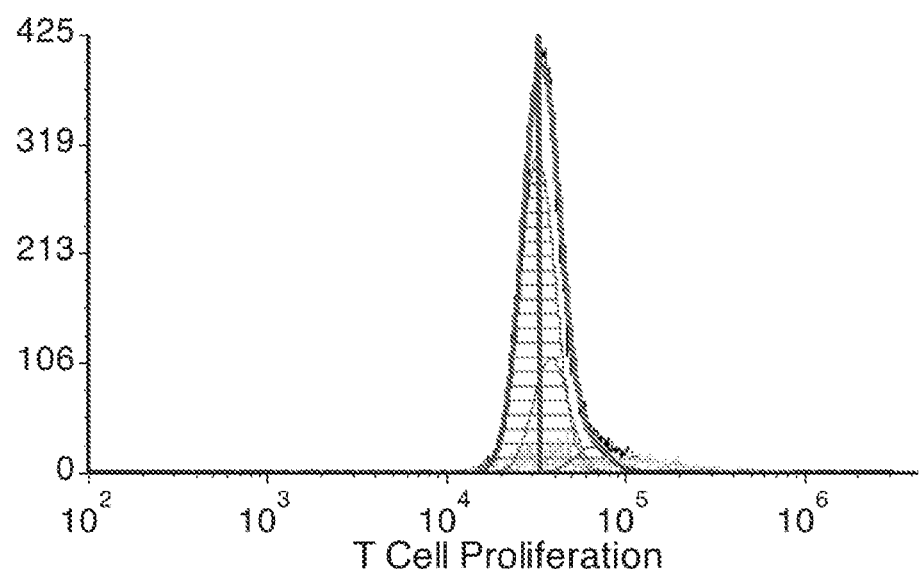
FIG. 36 shows allogeneic functional assay T cell control for N3. 1 million T cells (same donor for N1-N3) were cultured without iDCs for 5 days.

Tables 4-6 show allogeneic functional assay proliferation statistics for data in FIG. 26. iDCs were co-cultured with 1 million allogeneic T cells for 5 days. Proliferation histograms are shown in FIG. 27 (Experiment N1), FIG. 32 (Experiment N2), and FIG. 33 (Experiment N3). FIGS. 34-36 show the allogeneic functional assay T cell control.

TABLE 4

Allogeneic functional assay proliferation statistics for Experiment N1

| MO Seeding Density MOs/cm² | iDC Source | iDCs Seeded in Assay | Division Index | Proliferation Index | % Divided |
|---|---|---|---|---|---|
| 200,00 | Cell culture systems of the invention | 0k | 0.00 | 1.00 | 0.00 |
|  |  | 200k | 13.04 | 6.81 | 48.28 |
|  |  | 500k | 16.05 | 9.16 | 54.22 |
|  | 6-well plate | 0k | 0.00 | 1.00 | 0.00 |
|  |  | 200k | 8.17 | 3.12 | 29.61 |
|  |  | 500k | 9.55 | 3.41 | 28.22 |
| 400,000 | Cell culture systems of the invention | 0k | 2.00 | 1.02 | 1.99 |
|  |  | 200k | 10.09 | 4.19 | 35.09 |
|  |  | 500k | 15.94 | 7.14 | 41.08 |
|  | 6-well plate | 0k | 0.00 | 1.00 | 0.00 |
|  |  | 200k | 8.04 | 3.59 | 36.73 |
|  |  | 500k | 9.91 | 3.64 | 29.58 |
| 600,000 | Cell culture systems of the invention | 0k | 0.00 | 1.00 | 0.00 |
|  |  | 200k | 7.36 | 3.00 | 31.53 |
|  |  | 500k | 9.99 | 4.05 | 33.95 |
|  | 6-well plate | 0k | 0.00 | 1.00 | 0.00 |
|  |  | 200k | 8.55 | 4.00 | 39.71 |
|  |  | 500k | 9.08 | 4.18 | 39.33 |

TABLE 5

Allogeneic functional assay proliferation statistics for Experiment N2

| MO Seeding Density MOs/cm² | iDC Source | iDCs Seeded in Assay | Division Index | Proliferation Index | % Divided |
|---|---|---|---|---|---|
| 200,00 | Cell culture systems of the invention | 0k | 0.00 | 1.00 | 0.00 |
|  |  | 200k | 10.78 | 2.48 | 15.11 |
|  |  | 500k | 7.86 | 2.90 | 27.64 |
|  | 6-well plate | 0k | 0.00 | 1.00 | 0.00 |
|  |  | 200k | 4.47 | 1.27 | 7.64 |
|  |  | 500k | 5.40 | 1.77 | 17.49 |
| 400,000 | Cell culture systems of the invention | 0k | 0.00 | 1.00 | 0.00 |
|  |  | 200k | 6.56 | 2.06 | 19.10 |
|  |  | 500k | 6.83 | 2.21 | 20.77 |
|  | 6-well plate | 0k | 0.00 | 1.00 | 0.00 |
|  |  | 200k | 5.05 | 1.34 | 8.38 |
|  |  | 500k | 5.12 | 1.63 | 15.17 |
| 600,000 | Cell culture systems of the invention | 0k | 0.00 | 1.00 | 0.00 |
|  |  | 200k | 5.91 | 1.57 | 11.66 |
|  |  | 500k | 7.36 | 2.22 | 19.25 |
|  | 6-well plate | 0k | 0.00 | 1.00 | 0.00 |
|  |  | 200k | 4.15 | 1.26 | 8.10 |
|  |  | 500k | 5.40 | 1.60 | 13.60 |

TABLE 6

Allogeneic functional assay proliferation statistics for Experiment N3

| MO Seeding Density MOs/cm² | iDC Source | iDCs Seeded in Assay | Division Index | Proliferation Index | % Divided |
|---|---|---|---|---|---|
| 200,00 | Cell culture systems of the invention | 0k | 2.19 | 1.20 | 16.76 |
|  |  | 200k | 7.45 | 3.08 | 32.23 |
|  |  | 500k | 8.63 | 5.16 | 54.50 |
|  | 6-well plate | 0k | — | — | — |
|  |  | 200k | 3.70 | 1.34 | 12.65 |
|  |  | 500k | 4.87 | 1.87 | 22.36 |
| 400,000 | Cell culture systems of the invention | 0k | 0.00 | 1.00 | 0.00 |
|  |  | 200k | 7.34 | 3.35 | 37.05 |
|  |  | 500k | 8.34 | 4.50 | 47.74 |
|  | 6-well plate | 0k | — | — | — |
|  |  | 200k | 4.40 | 1.42 | 12.22 |
|  |  | 500k | 5.34 | 1.94 | 21.69 |
| 600,000 | Cell culture systems of the invention | 0k | — | — | — |
|  |  | 200k | 9.29 | 2.30 | 15.66 |
|  |  | 500k | 7.45 | 3.19 | 33.93 |
|  | 6-well plate | 0k | — | — | — |
|  |  | 200k | 3.80 | 1.35 | 12.65 |
|  |  | 500k | 6.55 | 2.64 | 29.63 |

Cell culture systems of the invention were developed as an enclosed, sterile cell culture system for improving the process of generating dendritic cells from precursor PBMCs or monocytes. This study indicated that cell culture systems of the invention generate iDCs that are comparable phenotypically and functionally to standard well plate generated iDCs. The optimum MO seeding density for cell culture systems of the invention and the effect of seeding density on the ability of the iDCs to induce T cell proliferation was systematically determined. The data indicates a strong correlation between iDC phenotype, specifically the extent of CD80/83/86 iDC expression, and their ability to induce T cell proliferation. Cell culture systems of the invention iDCs generated from a low MO seeding density (200k MOs/cm²) exhibited the greatest ability to induce T cell proliferation due to greater CD80/83/86 expression of the iDCs. Cell culture systems of the invention iDCs also performed better in the allogeneic T cell assay compared to 6-well plate iDCs within the 200k-600k MO seeding density range studied. Furthermore, cell culture systems of the invention generated similar numbers of iDCs as the 6-well plates at higher MO seeding densities though cell culture systems of the invention produce fewer iDCs than the 6-well plates at lower MO seeding densities on a normalized basis. The decision to generate iDCs at a low or high seeding density should be considered carefully and will depend on downstream application of the iDCs considering whether it is more important to generate a larger number of iDCs or to generate iDCs with greater functional competency. These tradeoffs are common in standard static culture and naturally extend to cell culture systems of the invention.

EXAMPLES

EDEN Cell Culture Cartridge and Fluidic System

EDEN was developed to generate therapeutically relevant numbers of iDCs in a single cell culture cartridge that is fully enclosed and unopen to the outside environment. Fresh differentiation medium was perfused into the cartridge and depleted medium was removed. EDEN generated iDCs exhibited phenotype expression and iDC yields similar to 6-well plate generated iDCs. iDCs matured in a cartridge according to the invention exhibited standard upregulation of CD80/83/86 and downregulation of CD209. Computational fluid dynamics simulations aided the design of the EDEN cartridge to ensure that perfused medium flowed properly throughout the cartridge and cytokines were sufficiently replenished. These results show that EDEN successfully generates ca. 25 million iDCs with a 20-35% iDC yield at the conditions tested.

The EDEN system is shown in FIG. 10. The EDEN cell culture cartridge was fabricated from commercially available polystyrene and acrylate cut using an Epilog Zing 16 laser system and assembled using 3M Adhesive Transfer tape. The polystyrene base was plasma treated. The cartridge has an internal surface area of 383.6 cm$^2$, volume of 122 mL, and measures 21.0 cm×21.0 cm×0.317 mm (length×width×height). Eight inlet ports around the perimeter allow fresh differentiation medium to perfuse into the cartridge and a single outlet port at the center allows depleted medium to be removed from the cartridge.

The fluidic system consisted of an inlet bottle for fresh differentiation medium, peristaltic pump, and outlet bottle for collecting effluent from the cartridge. An Ismatec IPC-N peristaltic pump was used with PharMED BPT tubing to maintain continuous perfusion of fresh differentiation medium at 8.0 µL/min/inlet. Silicone tubing was connected between the peristaltic tubing and cartridge inlet to facilitate gas exchange between the medium and ambient environment maintained at 37° C. and 5% $CO_2$ inside a Thermo Forma incubator. Silicone tubing was also used at the outlet port where perfusion flow rate was estimated to be 64 µL/min. Effluent collected in the waste reservoir was centrifuged to determine if cells were washed out of the cartridge due to perfusion; no cells were observed in the effluent indicating that generated iDCs remain inside the cartridge and perfusion flow rate is not high enough to resuspend cells residing at the polystyrene base. 285 mL of fresh differentiation medium was added to the inlet reservoir at startup (Day 0) and Day 3 to maintain perfusion throughout the 6 day differentiation. Cells were harvested by collecting the cell solution and washing each well 2× with cold DPBS. Adherent cells after the two DPBS washes were not collected.

Differentiation Medium

RPMI 1640 (Gibco 11875119) was supplemented with 10% fetal bovine serum (FBS; heat inactivated; MilliporeSigma F2442), 1% penicillin-streptomycin (P/S; Gibco 15140122), 500 U/mL IL-4 (R&D Systems 2041L), and 500 U/mL GM-CSF (R&D Systems 215GM).

PBMC Isolation and Monocyte Enrichment

Peripheral blood mononuclear cells (PBMCs) were isolated using Ficoll-Paque (GE Healthcare) from whole blood StemExpress. The whole blood was drawn and processed on the same day. Isolated PBMCs were cryopreserved at 50-60 million PBMCs/mL in CryoStor CS10 and remained in cryopreservation for at least 7 days prior to resuscitation. Monocytes (MOs) were enriched from resuscitated PBMCs using Miltenyi CD14 MicroBeads and two LS column passes to obtain a MO purity >95%. Enriched MOs from a single donor were suspended in 122 mL differentiation medium and seeded into the EDEN cartridge. Each experiment used MOs from a different donor.

6-Well Plate Control

A Corning Costar 6-well plate (3516) was used as a static control for iDC generation. Each well contained 2.5 mL differentiation medium and empty wells were filled with 3.0 mL DPBS. 1 mL fresh differentiation medium was added to each well on Day 3. Cells were harvested by collecting the cell solution and washing each well 2× with cold DPBS. Adherent cells after the two DPBS washes were not collected.

IDC Maturation

Maturation was conducted on a system according to the invention at 3.5 µL/min perfusion using a small version cartridge that was 17.4 cm$^2$ and held 5.5 mL maturation medium. Maturation medium consisted of RPMI 1640 supplemented with 10% HI-FBS, 1% P/S, 2 ng/mL IL-1β (BD Biosciences 554602), 1000 U/mL IL-6 (BD Biosciences 550071), 10 ng/mL TNF-α (MilliporeSigma 11088939001), and 1 µg/mL PGE2 (MilliporeSigma P6532). IDCs from the EDEN 1 experiment were seeded at 422,200 iDCs/cm$^2$ and allowed to mature for either 1 day or 3 days in an incubator at 37° C. and 5% $CO_2$. The cells were harvested using 2 cold PBS washes as described in Kozbial, 2018, Automated generation of immature dendritic cells in a single-use system, Journal of Immunological Methods, 457:53-65, which is incorporated herein by reference in its entirety.

Immunophenotyping

An ACEA Biosciences NovoCyte flow cytometer was used for immunophenotyping of harvested iDCs. Panel A tested viability (LIVE/DEAD Fixable Green Dead Cell Stain; Invitrogen L34970), CD209 (R&D Systems FAB 161P100), CD14 (Abcam ab157312), and CD45 (R&D Systems FAB1430A). Panel B tested CD80 (BD Biosciences 557226), CD83 (BD Biosciences 556855), CD86 (BD Biosciences 561128), and CD45; viability was not included due to limited detection channels. Panel C tested CD80, CD83, CD86, and CD209 (R&D Systems FAB161A). Gates were set using a CD209 isotype control (R&D Systems IC0041P) for Panel A and fluorescence-minus-one (FMO) controls.

Flow Cytometry Gating Strategy

Large cells were gated in the SSC-A/FSC-A plot followed by single cells in a FSC-A/FSC-H plot. Panel A: Viable/CD45+ cells were gated then CD14/CD209 was plotted to determine MO or iDC percentage. Panel B: Lymphocytes were gated on a CD45 histogram. Then CD80/83 and CD80/86 was plotted to determine iDC phenotype. Panel C: DCs were gated on a CD209/80 plot followed by a CD83/86 plot on the CD209+/80+ or CD209+/80− cells.

IDC Generation

Two iDC generation experiments were conducted in which 114.3 million and 78.3 million MOs were seeded into the EDEN cartridge. After 6 days differentiation, 25.5 million and 24.8 million iDCs were harvested from each cartridge. Viable iDCs harvested was calculated by multiplying total cells harvested by viable/CD45+ cells by iDCs (CD209+/14−). IDC yield (normalized to the number of MOs seeded) was calculated as the number of iDCs harvested divided by the MOs seeded and was 22.3% and 31.7% for the two EDEN experiments. 6-well plate controls show that iDC yield was similar to EDEN, where the well plate had a higher yield in experiment 1 and a lower yield in experiment 2.

Tabulated data are shown in Table 7. Phenotype data is shown in FIG. 16.

TABLE 7

Differentiation data for iDC generation in EDEN and 6-well plates

| Experiment | MOs Seeded (×10⁶) | Seeding Density (MO sper cm²) | Cells Harvested (×10⁶) | Viable CD45⁺ Cells | iDCs CD209⁺ CD14⁻ | Viable IDCs Harvested (×10⁶) | IDC Yield |
|---|---|---|---|---|---|---|---|
| EDEN 1 | 114.3 | 300,200 | 26.7 | 98.3% | 97.1% | 25.5 | 22.3% |
| EDEN 2 | 78.3 | 205,700 | 25.8 | 96.5% | 99.8% | 24.8 | 31.7% |
| 6-well plate 1 | 3.48 | 366,000 | 1.17 | 95.4% | 97.2% | 1.08 | 31.2% |
| 6-well plate 1 | 1.74 | 183,000 | 0.47 | 94.1% | 98.7% | 0.44 | 25.1% |

IDC Phenotype

Immunophenotyping of generated iDCs are shown in FIG. 16. EDEN and 6-well plate generated iDCs are phenotypically similar after 6 days of differentiation. The iDCs are CD209 (DC-SIGN) positive, CD14 negative, and exhibit low expression of CD80/83 as expected for MO derived iDCs. CD86 expression on EDEN 2 iDCs was unexpectedly high as this level of expression is typically expected on mature DCs. Dissolved proteins in fetal bovine serum (FBS) supplemented into the base medium may be a possible explanation for this irregular expression since FBS is animal derived and its composition cannot be strictly controlled. Additionally, contaminating proteins in the cartridge, since it was hand built in the lab, could also explain this high expression. Greater than 99.7% of the cells were CD45+ in the Panel B histogram (not shown). This protein expression profile for EDEN generated iDCs demonstrates the efficacy of EDEN in generating clinically relevant numbers of DCs that are phenotypically similar to well plate static culture.

IDC Maturation iDCs generated in EDEN 1 were subsequently matured in a cartridge according to the invention for either 1 day or 3 days. 7.31 million iDCs were seeded into each cartridge (422,200 iDCs/cm2) and 6.0 million (1 day maturation) and 4.8 million (3 day maturation) mature DCs (mDCs) were harvested, for a yield of 81.9% and 66.2%, respectively. Yield was calculated as the number of seeded iDCs divided by the number of harvested mDCs. MDC count was determined strictly by calculating viable CD45+/209+ cells, so yield values less than 100% indicate the extent of cell death in each experiment which was 18.1% (1 day maturation) and 33.8% (3 day maturation) for the two sub-experiments.

Maturation results are tabulated in Table 8. Maturation was performed in a small version cartridge. Phenotype data is shown in FIG. 17. In particular, immunophenotyping of EDEN 1 mDCs is shown in FIG. 17. CD209 expression was lower for mDCs and decreased with maturation length. CD80 expression increased from ca. 11% for iDCs to 48% and 55% for 1 and 3 day matured DCs, respectively. CD80 expression is generally low on iDCs and upregulated on mDCs, indicating that maturation was successful. CD83/86 expression is clearly dependent upon CD80 expression, shown in the last two columns of FIG. 17. CD80+ mDCs exhibited greater expression of CD86 compared to CD80− mDCs; whereas CD83 expression remained unchanged.

TABLE 8

Maturation data for EDEN 1 generated iDCs

| Experiment | IDCs Seeded (×10⁶) | Seeding Density (iDCs per cm²) | Cells Harvested (×10⁶) | Viable CD45⁺ Cells | MDCs CD209⁺ CD14⁻ | Viable MDCs Harvested (×10⁶) | MDC Yield |
|---|---|---|---|---|---|---|---|
| 1 Day Maturation | 7.31 | 422,200 | 6.24 | 96.3% | 99.6% | 6.0 | 81.9% |
| 3 Day Maturation | 7.31 | 422,200 | 5.30 | 92.1% | 99.1% | 4.8 | 66.2% |

Computational Fluid Dynamics (CFD) Simulations

CFD simulations in COMSOL Multiphysics were utilized in designing EDEN to understand how medium flows within the cartridge. Water at 37° C. was used to simulate differentiation medium. The cartridge was initially filled with plain water without cytokines. In practice, the cartridge is filled with differentiation medium containing cytokines. However, initially filling the cartridge with plain medium (water) allows cytokine convection to be visualized since cytokine diffusion is extremely low (9216 μm²/day) and convection is the driving force behind the cytokine gradient. Water containing 1.16 mol/m³ (500 U/mL) R&D Systems IL-4 was perfused into the cartridge at 8 μL/min/inlet and exited through the outlet at the cartridge center. Cytokine consumption/depletion was not factored into this analysis since we were interested in determining optimum medium flow of fresh differentiation medium. FIG. 11 shows the cartridge flow channel which describes the volume within the cartridge that medium flows. IL-4 cytokine concentration was modeled on the lower polystyrene surface of the flow channel where the cells reside on the cartridge base, as depicted by the purple surface in FIG. 12. Streamlines and gauge pressure due to perfusion are shown in FIGS. 13 and 14, respectively. IL-4 concentration gradient is shown in FIG. 15 for each 24 hour period of perfusion.

These CFD data were critical in designing a cartridge which sufficiently allowed perfused medium to spread throughout the cartridge. Cytokine concentration and streamline data shows that at 8 μL/min/inlet laminar flow, the cartridge is split between eight regions. Each region is replenished with fresh differentiation medium after ca. 4 days. Initial CFD simulations indicated that dead areas, or dead spots in flow, formed at the location of the v-shaped notches, thus these notches were added to eliminate the dead areas, or dead spots in flow, and facilitate desired fluid flow. The 8 cylindrical pillars within the cartridge support the upper acrylic surface. Before these were added, slight sagging of the acrylic was observed and the acrylic was supported by medium within the cartridge which would cause unnecessary pressure within the cartridge that may affect the cells. Thus, these features, i.e., the notches and pillars, were added to alleviate the dead areas, or dead spots in flow, and pressure concerns resulting in the final EDEN cartridge design that sufficiently aided perfused medium to flow within the cartridge without causing undesired pressure gradients.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

While the present invention has been described in conjunction with certain embodiments, one of ordinary skill, after reading the foregoing specification, will be able to effect various changes, substitutions of equivalents, and other alterations to the compositions and methods set forth herein.

What is claimed is:

1. A cell culture system comprising:
a cell culture cartridge comprising a top surface and an opposing bottom surface coupled to one another and defining a cell culture chamber therebetween, wherein the cell culture chamber comprises a plurality of zones geometrically configured to provide symmetrical fluid flow channels in the cell culture chamber and to avoid dead areas of flow within the cell culture chamber during flow of a fluid therein.

2. The cell culture system of claim 1, further comprising:
a computer system having a central processing unit for carrying out instructions;
one or more control systems; and
one or more computer programs tangibly embodied in a non-transitory computer-readable medium for execution by the computer system.

3. The cell culture system of claim 2, further comprising one or more pumps operably connected to the central processing unit.

4. The cell culture system of claim 3, wherein the computer system is operable to execute instructions controlling the one or more pumps to provide unidirectional flow or counter-current flow of a fluid or an entity within the system.

5. The cell culture system of claim 2, wherein the one or more control systems are operable to execute instructions for controlling movement of a fluid through the system, monitoring and controlling one or more parameters within the system, and detecting a characteristic of a product.

6. The cell culture chamber of claim 5, wherein the characteristic of the product is one or more of a presence of a cell-based immunotherapy product, a quantity of a product, and a conversion rate of a product.

7. The cell culture system of claim 5, further comprising one or more sensors operably coupled to the cell culture chamber and the computer system for carrying out instructions for automatic monitoring and adjustment of the one or more parameters.

8. The cell culture system of claim 7, wherein the one or more parameters are perfusion parameters.

9. The cell culture system of claim 8, wherein the perfusion parameters comprise one or more of a medium flow rate, a cytokine concentration, a phenotypic measurement, and a duration of a culture cycle.

10. The cell culture system of claim 9, wherein the computer system is operable to execute instructions to vary the perfusion parameters during the culture cycle.

11. The cell culture system of claim 2, wherein the instructions cause the system to:
receive as a first input data comprising a size of the cell culture chamber,
receive as a second input data comprising a first concentration of a first cell type and a second concentration of a second cell type in one or more fluids that will be introduced into the cell culture chamber, and
calculate, based on the first and second inputs, a perfusion rate of a perfusion fluid that will be introduced into the cell culture chamber that maximizes a probability of the first cell type and the second cell type contacting each other within the cell culture chamber.

12. The cell culture system of claim 2, further comprising instructions executable for an optimization using an objective function to optimize operational constraints for one or more process decision variables.

13. The cell culture system of claim 12, wherein the process decision variables are one or more of temperature, pressure, flow-rate, and channel dimensions.

14. The cell culture system of claim 1, wherein the cell culture chamber comprises a bottom surface with a modification to facilitate cell adhesion.

15. The cell culture system of claim 14, wherein the bottom surface comprises polystyrene which has undergone treatment with an air or $O_2$ plasma.

16. The cell culture system of claim 14, wherein the modification is the addition of one or more proteins or poly-amino acids chosen from the group consisting of fibronectin, laminin, and collagen.

17. The cell culture system of claim 1, further comprising a sample tracking component.

18. The cell culture system of claim 1, further comprising an outlet and a plurality of inlets positioned around a periphery of the cell culture cartridge.

19. The cell culture system of claim 18, further comprising a medium reservoir connected to the inlets and a waste reservoir connected to the outlet.

20. The cell culture system of claim 18, further comprising Luer Activated Valves enabling sterile bidirectional flow.

* * * * *